(12) United States Patent
Hedrich et al.

(10) Patent No.: US 11,874,242 B2
(45) Date of Patent: Jan. 16, 2024

(54) EVALUATION ARRANGEMENT FOR A THERMAL GAS SENSOR, METHODS AND COMPUTER PROGRAMS

(71) Applicants: Hahn-Schickard-Gesellschaft für angewandte Forschung e.V., Villingen-Schwenningen (DE); GS Elektromedizinische Geräte G. Stemple GmbH, Kaufering (DE)

(72) Inventors: Frank Hedrich, Villingen-Schwenningen (DE); Bernd Ehrbrecht, Unterkirnach (DE); Gerhard Kattinger, St. Georgen (DE); Kurt Kliche, Wendlingen (DE)

(73) Assignees: Habn-Schickard-Gesellschaft für angewandte Forschung e.V., Villingen-Schwenningen (DE); GS Elektromedizinische Geräte G. Stemple GmbH, Kaufering (DE)

( * ) Notice: Subject to any disclaimer, the term of this patent is extended or adjusted under 35 U.S.C. 154(b) by 0 days.

(21) Appl. No.: 17/820,164

(22) Filed: Aug. 16, 2022

(65) Prior Publication Data
US 2022/0390397 A1    Dec. 8, 2022

Related U.S. Application Data

(60) Division of application No. 16/921,407, filed on Jul. 6, 2020, now Pat. No. 11,686,695, which is a
(Continued)

(30) Foreign Application Priority Data

Jan. 5, 2018    (EP) .................................... 18150496

(51) Int. Cl.
G01N 25/18    (2006.01)
G01F 1/688    (2006.01)
G01N 33/497    (2006.01)

(52) U.S. Cl.
CPC ........... *G01N 25/18* (2013.01); *G01F 1/6888* (2013.01); *G01N 33/497* (2013.01)

(58) Field of Classification Search
None
See application file for complete search history.

(56) References Cited

U.S. PATENT DOCUMENTS 5,693,875 A    12/1997 Cremer
6,550,324 B1    4/2003 Mayer et al.
(Continued)

FOREIGN PATENT DOCUMENTS

CN    1538934 A    10/2004
CN    102169097 A    8/2011
(Continued)

OTHER PUBLICATIONS

"Universal Semiconductor", Universal Semiconductor, 4 pages.
(Continued)

*Primary Examiner* — Raul J Rios Russo
*Assistant Examiner* — Carl F. R. Tchatchouang
(74) *Attorney, Agent, or Firm* — Perkins Coie LLP; Michael A. Glenn

(57) ABSTRACT

Evaluation arrangement for a thermal gas sensor with at least one heater and at least one detector. The evaluation arrangement is configured to obtain information about an amplitude of a detector signal of a first detector, and information about a first phase difference between a heater signal and the detector signal of the first detector. In addition, the evaluation arrangement is configured to form as an intermediate quantity, dependent on the information about the
(Continued)

amplitudes of the detector signal and dependent on the information about the first phase difference, a combination signal, and to determine information about a gas concentration or information about a thermal diffusivity of a fluid on the basis of the combination signal.

15 Claims, 38 Drawing Sheets

Related U.S. Application Data continuation of application No. PCT/EP2019/050261, filed on Jan. 7, 2019.

(56) References Cited

U.S. PATENT DOCUMENTS

| | | | |
|---|---|---|---|
| 6,688,159 | B1 | 2/2004 | Grunewald |
| 7,780,343 | B2 | 8/2010 | Chen et al. |
| 2002/0179443 | A1* | 12/2002 | Hada .................. G01N 27/4067 204/408 |
| 2004/0195096 | A1 | 10/2004 | Tsamis et al. |
| 2007/0241093 | A1 | 10/2007 | Von et al. |
| 2010/0184397 | A1 | 7/2010 | Kadous et al. |
| 2010/0201551 | A1 | 8/2010 | Sebastiano et al. |
| 2011/0154885 | A1 | 6/2011 | Nakano et al. |
| 2012/0118060 | A1 | 5/2012 | Kimura |
| 2013/0174646 | A1* | 7/2013 | Martin .................... F24F 11/62 73/31.02 |
| 2013/0234330 | A1 | 9/2013 | Theuss |
| 2014/0373621 | A1* | 12/2014 | Schirm .............. G01N 33/0031 73/204.11 |
| 2015/0053019 | A1 | 2/2015 | Sulzer et al. |
| 2015/0285750 | A1 | 10/2015 | Humbert et al. |
| 2016/0025660 | A1 | 1/2016 | Hepp et al. |
| 2016/0067443 | A1* | 3/2016 | Hunt .................. A61M 16/109 128/203.14 |
| 2016/0258986 | A1 | 9/2016 | Terricciano et al. |
| 2016/0290849 | A1 | 10/2016 | Badarlis et al. |
| 2016/0363551 | A1 | 12/2016 | Morishita |
| 2020/0232971 | A1 | 7/2020 | Hedrich et al. |

FOREIGN PATENT DOCUMENTS

| | | |
|---|---|---|
| CN | 102197293 A | 9/2011 |
| CN | 104246451 A | 12/2014 |
| CN | 104977327 A | 10/2015 |
| DE | 102006054505 A1 | 5/2008 |
| DE | 102008047511 A1 | 3/2009 |
| DE | 102011075519 A1 | 11/2012 |
| DE | 102013102230 A1 | 9/2013 |
| DE | 102013102398 A1 | 9/2014 |
| DE | 102015107584 A1 | 11/2016 |
| EP | 1144958 B1 | 3/2004 |
| EP | 1688784 A1 | 8/2006 |
| EP | 2175246 A1 | 4/2010 |
| EP | 2348292 A1 | 7/2011 |
| EP | 2645089 A1 | 10/2013 |
| EP | 2869041 A1 | 5/2015 |
| EP | 2887057 A1 | 6/2015 |
| EP | 3502687 A1 | 6/2019 |
| JP | 493648 | 7/1994 |
| JP | H08136490 A | 5/1996 |
| JP | 2000028558 A | 1/2000 |
| JP | 2022075661 A | 5/2002 |
| JP | 2006208257 A | 8/2006 |
| JP | 2009288082 A | 12/2009 |
| JP | 2011137679 A | 7/2011 |
| JP | 2013257273 A | 12/2013 |
| JP | 2015064305 A | 4/2015 |
| JP | 2016138797 A | 8/2016 |
| JP | 2017003493 A | 1/2017 |
| JP | 2021515882 A | 6/2021 |
| WO | 2011018592 A1 | 2/2011 |
| WO | 2013030198 A1 | 3/2013 |
| WO | 2015027210 A1 | 2/2015 |
| WO | 2015172974 A1 | 11/2015 |
| WO | 2016180760 A1 | 11/2016 |
| WO | 2017103577 A1 | 6/2017 |
| WO | 2019034570 A1 | 2/2019 |

OTHER PUBLICATIONS

Al-Salaymeh, A., "Development of a two-wire thermal flow sensor for industrial applications", Journal of Quality in Maintenance Engineering, vol. 9 Issue: 2 (https://doi.org/10.1108/13552510310482370), 2003, pp. 113-131.

Badarlis, Anastasios, et al., "Measurement of Gas Thermal Properties Using the Parametric Reduced-Order Modeling Approach", IEEE Sensors Journal, IEEE Service Center, New York, NY, US, vol. 16, No. 12, Jun. 1, 2016 (Jun. 1, 2016), XP011610625, ISSN: 1530-437X, DOI: 10.1109/ JSEN.2016.2558820, Jun. 15, 2016, pp. 4704-4714.

Baehr, Hans Dieter, et al., "Wärme—und Stoffübertragung", CIP-Eintrag beantragt—PeriodischeTemperaturänderungen, 1994, 7 Pages.

Baehr, H. D., et al., "Wärme—und Stoffübertragung", 6. neu bearbeitete Auflage ed Springer-Verlag, 2008 (no English translation available), 2008.

Baehr, Hans Dieter, et al., "WärmeUndStoffübertragung", Inhaltsverzeichnis, 1994, 21 Pages.

Baehr, Hans Dieter, et al., "WärmeUndStoffübertragung", Inhaltsverzeichnis, 1998, 21 Pages.

Billat, S, et al., "Convection-based micromachined inclinometer using SOI technology", Proceedings of the IEEE 14th. Annual International Conference on Micro Electro Mechanical Systems. MEMS 2001. Interlaken, Switzerland, Jan. 21-25, 2001; XP032403321, DOI: 10.1109/MEMSYS.2001.906504, ISBN: 978-0-7803-5998-7, Jan. 2001, pp. 159-161.

Grienauer, Heinrich S, "Temperature Modulated Thermal Conductivity Gas Analysis Sensor Properties and Applications", 16. GMA/ITG-Fachtagung Sensoren und Messsysteme 2012; May 22-23, 2012; Nürnberg, Germany; Chapter 1.2 Chemische Sensoren; DOI: 10.5162/sensoren2012/1.2.2; ISBN: 978-3-9813484-0-8, 2012, pp. 54-61.

Kliche, K, et al., "Sensor for gas analysis based on thermal conductivity, specific heat capacity and thermal diffusivity", 2011 IEEE 24th International Conference on Micro Electro Mechanical Systems (MEMS), 2011.

Kliche, K, et al., "Sensor for Thermal Gas Analysis Based on Micromachined Silicon-Microwires", IEEE Sensors Journal, IEEE Service Center, New York, NY, US, vol. 13, No. 7, XP011513069, ISSN: 1530-437X, DOI: 10.1109/JSEN. 2013.2252008, Jul. 1, 2013, pp. 2626-2635.

Kliche, Kurt, et al., "Sensorsystem zur thermischen Gasanalyse von Gasgemischen", Konferenzbeitrag in Proc. of Mikrosystemtechnik Kongress 2011, Darmstadt, Deutschland; Oct. 10, 2011, Seite 875-878, ISBN: 978-3-8007-3367-5 (2011) (contains English language abstract), Oct. 2011.

MFHS, "MFHS 2012 1st International Conference on Microfluidic Handling Systems", Proceedings, Oct. 2012, 20 Pages.

Santucci, A., et al., "Data-acquisition system for measurement of thermal diffusivity and propagation properties of thermal waves by a non-steady-state method", Review of Scientific Instruments, AIP, Melville, NY, US, vol. 57, No. 8, Aug. 1, 1986 (Aug. 1, 1986),XP001327224, ISSN: 0034-6748, Mar. 10, 1986, pp. 1627-1632.

Sensirion the Sensor Company, "Sensirion", CMOSens Technology (no English translation available), 7 Pages.

Simon, Isolde, et al., "Thermal and gas-sensing properties of a micromachined thermal conductivity sensor for the detection of hydrogen in automotive applications", Sensors and Actuators A: Physical, 97-98, doi: 10.1016/S0924-4247(01)00825-1, Apr. 2002, pp. 104-108.

Van Baar, J. J., et al., "Micromachined structures for thermal measurements of fluid and flow parameters", Journal of Micromechanics and Microengineering, 11(4). doi: 10.1088/0960-1317/11/4/304, Jul. 2001, pp. 311-318.

(56) References Cited

OTHER PUBLICATIONS

Ali Sukru Cubukcu et al., A dynamic thermal flow sensors for simultaneous measurement of thermal conductivity and flow velocity of gases; Sensors and Actuators A 208; Dec. 12, 2013 (15 pages).

* cited by examiner

EVALUATION ARRANGEMENT FOR A THERMAL GAS SENSOR, METHODS AND COMPUTER PROGRAMS

CROSS-REFERENCES TO RELATED APPLICATIONS

This application is a divisional of copending U.S. patent application Ser. No. 16/921,407, filed Jul. 6, 2020, which is a continuation of International Application No. PCT/EP2019/050261, filed Jan. 7, 2019, and additionally claims priority from European Application Nos. EP 18 150 496.0, filed Jan. 5, 2018, all of which applications are incorporated herein by reference in their entirety.

BACKGROUND OF THE INVENTION

Embodiments according to the invention relate to evaluation arrangements for a thermal gas sensor, methods and computer programs.

Currently, gases may be analyzed with respect to their properties using different sensors. Today, there are different systems for patient ventilation on the market. They are distinguished according to their utilization in the clinical area and in the home care area (e.g. systems of the companies Heinen+Löwenstein, Dräger and Stephan Medizintechnik). The systems of these providers contain only in their top variations all measuring means for determining pressure, expiratory/inspiratory flow, and breathing gas analysis. To this end, several devices that overwhelmingly measure remotely from the patient have to be combined.

In light of the aforementioned, there is a need for a concept that enables a better compromise between a reduction of an installation space and a reduction of a system weight of a gas measuring system, and provides an exact flow measurement as well as a quick gas analysis.

SUMMARY

An embodiment may have an evaluation arrangement for a thermal gas sensor with at least one heater and at least one detector, wherein the evaluation arrangement is configured to acquire information about an amplitude of a detector signal of a first detector, and information about a first phase difference between a heater signal and the detector signal of the first detector; and wherein the evaluation arrangement is configured to form as an intermediate quantity, dependent on the information about the amplitudes of the detector signal and dependent on the information about the first phase difference, a combination signal, and wherein the evaluation arrangement is configured to determine information about a gas concentration or information about a thermal diffusivity of a fluid on the basis of the combination signal.

Another embodiment may have an evaluation arrangement for a thermal gas sensor with at least one heater and two detectors arranged in different distances to the heater, wherein the evaluation arrangement is configured to acquire information about an amplitude of a detector signal of a first detector, information about an amplitude of a detector signal of a second detector, information about a first phase difference between a heater signal and the detector signal of the first detector, and information about a second phase difference between the heater signal and the detector signal of the second detector; and wherein the evaluation arrangement is configured to form as an intermediate quantity, dependent on the information about the amplitudes of the detector signals and dependent on the information about the first phase difference and dependent on the information about the second phase difference, a combination signal, and wherein the evaluation arrangement is configured to determine information about a gas concentration or information about a thermal diffusivity of a fluid on the basis of the combination signal.

Another embodiment may have a method for evaluating signals of a thermal gas sensor with at least one heater and at least one detector, wherein the method includes acquiring information about an amplitude of a detector signal of the first detector, and information about a first phase difference between a heater signal and the detector signal of the first detector; and wherein a combination signal is formed as an intermediate quantity, dependent on the information about the amplitudes of the detector signal and dependent on the information about the first phase difference, and wherein information about a gas concentration or information about a thermal diffusivity of a fluid is determined on the basis of the combination signal.

Another embodiment may have a method for evaluating signals of a thermal gas sensor with at least one heater and two detectors arranged in different distances to the heater, wherein the method includes acquiring information about an amplitude of a detector signal of a first detector, information about an amplitude of a detector signal of a second detector, information about a first phase difference between a heater signal and the detector signal of the first detector, and information about a second phase difference between the heater signal and the detector signal of the second detector; and wherein a combination signal is formed as an intermediate quantity, dependent on the information about the amplitudes of the detector signals and dependent on the information about the first phase difference and dependent on the information about the second phase difference, and wherein information about a gas concentration or information about a thermal diffusivity of a fluid is determined on the basis of the combination signal.

Another embodiment may have a non-transitory digital storage medium having a computer program stored thereon to perform the method for evaluating signals of a thermal gas sensor with at least one heater and at least one detector, wherein the method includes acquiring information about an amplitude of a detector signal of the first detector, and information about a first phase difference between a heater signal and the detector signal of the first detector; and wherein a combination signal is formed as an intermediate quantity, dependent on the information about the amplitudes of the detector signal and dependent on the information about the first phase difference, and wherein information about a gas concentration or information about a thermal diffusivity of a fluid is determined on the basis of the combination signal, when said computer program is run by a computer.

Another embodiment may have a non-transitory digital storage medium having a computer program stored thereon to perform the method evaluating signals of a thermal gas sensor with at least one heater and two detectors arranged in different distances to the heater, wherein the method includes acquiring information about an amplitude of a detector signal of a first detector, information about an amplitude of a detector signal of a second detector, information about a first phase difference between a heater signal and the detector signal of the first detector, and information about a second phase difference between the heater signal and the detector signal of the second detector; and wherein a combination signal is formed as an intermediate quantity, dependent on the information about the amplitudes of the detector signals and dependent on the information about the first phase difference and dependent on the information about the second phase difference, and wherein information about a gas concentration or information about a thermal diffusivity of a fluid is determined on the basis of the combination signal, when said computer program is run by a computer.

Another embodiment may have an evaluation arrangement for a thermal gas sensor with at least one heater and at least one detector, wherein the evaluation arrangement is configured to control a heating power applied to the heater dependent on at least one sensor signal from at least one detector in order to bring the at least one sensor signal into a predetermined value range; and wherein the evaluation arrangement is configured to consider information about the heating power when deriving information about a gas concentration from the at least one sensor signal.

Another embodiment may have a method for operating an evaluation arrangement for a thermal gas sensor with at least one heater and at least one detector, wherein the method includes controlling a heating power applied to the heater dependent on at least one sensor signal from at least one detector in order to bring a sensor signal into a predetermined value range; and wherein the method includes considering information about the heating power when deriving information about a gas concentration from the at least one sensor signal.

Another embodiment may have a non-transitory digital storage medium having a computer program stored thereon to perform the method for operating an evaluation arrangement for a thermal gas sensor with at least one heater and at least one detector, wherein the method includes controlling a heating power applied to the heater dependent on at least one sensor signal from at least one detector in order to bring a sensor signal into a predetermined value range; and wherein the method includes considering information about the heating power when deriving information about a gas concentration from the at least one sensor signal, when said computer program is run by a computer.

Another embodiment may have an evaluation arrangement for a thermal gas sensor with at least one heater and one detector, wherein the evaluation arrangement is configured to apply to the heater a periodic signal with a specified period duration, and wherein the evaluation arrangement is configured to sample at least one sensor signal from a detector at three points in time, wherein a second sampling time is time-shifted by 90°, with respect to the period duration, compared to a first sampling time, and wherein a third sampling time is time-shifted by 180°, with respect to the period duration, compared to a first sampling time, and wherein the evaluation arrangement is configured to identify, on the basis of three sample values that are based on a sampling of the sensor signal at the first sampling time, the second sampling time, and the third sampling time, whether a first sample value and a third sample value constitute a maximum value and a minimum value of the sensor signal.

Another embodiment may have a method for operating a thermal gas sensor with at least one heater and at least one detector, wherein the method includes applying a periodic signal with a specified period duration to the heater, and wherein at least one sensor signal is sampled by a detector at three points in time, wherein a second sampling time is time-shifted by 90°, with respect to the period duration, compared to a first sampling time, and wherein a third sampling time is time-shifted by 180°, with respect to the period duration, compared to a first sampling time, and wherein, on the basis of three sample values that are based on a sampling of the sensor signal at the first sampling time, the second sampling time, and the third sampling time, it is identified whether a first sample value and a third sample value constitute a maximum value and a minimum value of the sensor signal.

Another embodiment may have a non-transitory digital storage medium having a computer program stored thereon to perform the method for operating a thermal gas sensor with at least one heater and at least one detector, wherein the method includes applying a periodic signal with a specified period duration to the heater, and wherein at least one sensor signal is sampled by a detector at three points in time, wherein a second sampling time is time-shifted by 90°, with respect to the period duration, compared to a first sampling time, and wherein a third sampling time is time-shifted by 180°, with respect to the period duration, compared to a first sampling time, and wherein, on the basis of three sample values that are based on a sampling of the sensor signal at the first sampling time, the second sampling time, and the third sampling time, it is identified whether a first sample value and a third sample value constitute a maximum value and a minimum value of the sensor signal, when said computer program is run by a computer.

Another embodiment may have an evaluation arrangement for a thermal gas sensor with at least one heater and at least one detector, wherein the evaluation arrangement is configured to control, dependent on at least one sensor signal from at least one detector, a heating power applied to the heater in order to bring the at least one sensor signal into a predetermined value range; and wherein the evaluation arrangement is configured to consider information about the heating power when deriving information about a gas concentration from the at least one sensor signal, wherein the evaluation arrangement is configured to use a phase difference and/or an amplitude difference and/or an offset difference between the at least one sensor signal and a signal of the heater for deriving the information about the gas concentration.

Another embodiment may have a method for operating an evaluation arrangement for a thermal gas sensor with at least one heater and at least one detector, wherein the method includes controlling, dependent on at least one sensor signal from at least one detector, a heating power applied to the heater in order to bring the at least one sensor signal into a predetermined value range; and wherein the method includes considering information about the heating power when deriving information about a gas concentration from the at least one sensor signal, wherein the method includes using a phase difference and/or an amplitude difference and/or an offset difference between the at least one sensor signal and a signal of the heater for deriving the information about the gas concentration.

An embodiment concerns an evaluation arrangement for a thermal gas sensor with at least one heater (e.g. a heating element) and at least one detector (e.g. a "thermopile structure", temperature-variable resistors or thermistors). For example, the evaluation arrangement is configured to obtain information about an amplitude of a detector signal of a first detector (e.g. D1.Uss) and information about a first phase difference between a heater signal and the detector signal of the first detector (e.g. (D1-Hz).phi). In addition, the evaluation arrangement may be configured to form as an intermediate quantity, dependent on the information about the amplitude of the detector signal (e.g. D1.Uss and/or D2.Uss) and dependent on the information about the first phase difference, a combination signal that may combine amplitude information and phase information. In addition, the evaluation arrangement is configured to determine, e.g., information about a gas concentration or information about a thermal diffusivity of a fluid (e.g. a gas or gas mixture) on the basis of the combination signal (e.g., without separately considering individual information incorporated into the combination signal in the further process of the calculations).

According to an embodiment, the heater and the at least one detector may be cyclically swapped in order to minimize possibly occurring (synchronization) errors. In other words, at a first point in time, the detector may act as a heater and the heater may act as a detector, and, at a second point in time, the detector may be used as a detector and the heater may be used as a heater.

According to an embodiment, the evaluation arrangement includes two detectors, wherein these two detector comprise a same distance to the heater. In this case, for example, a sum of the information about the amplitudes of the two detector signals (e.g. D1.Uss and D2.Uss) from the two detectors as well as a sum of the information about the two phase differences ((D1-Hz).phi and (D2-Hz).phi) of the two detectors may be incorporated into the combination signal.

An embodiment concerns an evaluation arrangement for a thermal gas sensor with at least one heater (e.g. a heating element) and two detectors (e.g. a first thermal element structure and a second thermal element structure, or temperature-variable resistors, or thermistors) arranged in different distances to the heater, wherein the evaluation arrangement is configured to obtain information about an amplitude of a detector signal of a first detector (e.g. D1.Uss), information about an amplitude of a detector signal of a second detector (e.g. D2.Uss), information about a first phase difference between a heater signal and the detector signal of the first detector (e.g. (D1-Hz).phi), and information about a second phase difference between the heater signal and the detector signal of the second detector (e.g. (D2-Hz).phi). The evaluation arrangement may be configured to form as an intermediate quantity, dependent on the information about the amplitudes of the detector signals (e.g. D1.Uss of the first detector and D2.Uss of the second detector) and dependent on the information about the first phase difference and dependent on the information about the second phase difference, a combination signal that may combine amplitude information and phase information. In addition, the evaluation arrangement is configured to determine information about a gas concentration or information about a thermal diffusivity of a fluid (e.g. a gas or a gas mixture) on the basis of the combination signal (e.g. without separately considering the individual information incorporated into the combination signal in the further process of the calculations).

According to an embodiment, a gas may be arranged in the thermal gas sensor between the at least one heater and the detectors arranged in different distances or in the same distance (e.g. symmetrical) to the heater, wherein said gas may be analyzed with the evaluation arrangement in conjunction with the thermal gas sensor. To this end, for example, heat is transported from the at least one heater to the first detector and the second detector via the gas and/or gas mixture located therebetween. In this case a detector signal detected by the first detector and/or a detector signal detected by the second detector may indicate the heat transported from the heater to the respective detector. If a heating signal amplitude (e.g. a heater amplitude) of the at least one heater varies (e.g. periodic excitation of the heater), the two detectors may detect a varying amplitude that corresponds to the heater. The detector signal of the first detector and/or the second detector may be transmitted to the evaluation arrangement. Thus, the evaluation arrangement may obtain from the detector signal of the first detector and from the detector signal of the second detector the respective information about the amplitude as well as information about the first phase difference between the heater signal and the detector signal of the first detector and the information about the second phase difference between the heater signal and the detector signal of the second detector. To this end, for example, the evaluation arrangement may obtain from the thermal gas sensor the heater signal in addition to the detector signals of the first detector and/or the second detector. Alternatively, for example, the evaluation arrangement may directly obtain from the thermal gas sensor the information about the amplitude of the detector signal of the first detector, the information about the amplitude of the detector signal of the second detector, the information about the first phase difference, and the information about the second phase difference.

This embodiment of the evaluation arrangement is based on the finding that the combination signal, based on the information about the amplitudes of the detector signals and dependent on the information about the first phase difference and the information about the second phase difference, constitutes a very stable signal that may be very quickly processed by the evaluation arrangement in order to determine, for example, a gas concentration or information about a thermal diffusivity of the fluid. Thus, the evaluation arrangement enables a quick gas analysis.

According to an embodiment, the evaluation arrangement may be configured to obtain information about a heater amplitude. In addition, the evaluation arrangement may be configured to form a linear combination of the information about the heater amplitude, the information about amplitudes of the detector signals, the information about the first phase difference, and the information about the second phase difference, in order to determine the combination signal (sigX). For example, the information about the heater amplitude may be information about a heating power. Here, the information about a heater amplitude may also be referred to as Hz.Uss. For example, the evaluation arrangement may obtain the information about the heater amplitude directly from the thermal gas sensor, or obtain the same from a heater signal transmitted from the thermal gas sensor to the evaluation arrangement, for example. For example, the linear combination may comprise a first term having a first linear combination of the information about the heater amplitude and the information about amplitudes of the detector signals, and a second term having a second linear combination of the information about the first phase difference and the information about the second phase difference. In this case, for example, the first term and the second term may be weighted with different constants in the linear combination in order to determine the combination signal. Due to the fact that the evaluation arrangement considers the heater amplitude when determining the combination signal, the heater signal (e.g. a signal of periodic temperature waves emitted by the heater) may be compared with the detector signal of the first detector and/or the second detector (a received signal of periodic temperature waves), as a result of which a heat transfer from the heater to the two detectors via the gas to be analyzed may be determined very precisely. This enables a very precise and quick gas analysis with the evaluation arrangement.

According to an embodiment, the evaluation arrangement may be configured to obtain the combination signal sigX according to:

$$sigX = sigUss*Ka + sigPhi*Kp$$

Here, sigUss may be amplitude information or an amplitude signal that may depend on the information about the amplitude of the detector signal of the first detector and on the information about the amplitude of the detector signal of the second detector. The term sigPhi may be phase information or an added phase signal that may depend on the information about the first phase difference and on the information about the second phase difference, and the factors Ka and Kp may be constants. In this case, the constants Ka and Kp may separately weigh the amplitude information and the phase information, respectively, so that the evaluation arrangement may obtain the combination signal sigX. The amplitude information sigUss may be a linear combination of the information about the amplitude of the detector signal of the first detector and the information about the amplitude of the detector signal of the second detector. The phase information sigPhi may be a linear information of the information about the first phase difference and the information about the second phase difference. For example, the constants Ka and Kp may be conversion factors. According to an embodiment, Ka and Kp are weighting factors for an optimized combination signal, wherein the factors Ka and Kp may be unitless quantities (e.g., this is not necessary for an embedded system as is used herein, e.g., providing a CO2 concentration). According to an embodiment, for example, the embedded system provides AD digits for the amplitude, and phase information is determined, e.g., from the timing unit of the embedded system, e.g. which measures the times until the comparator tilts. Thus, for example, a conversion to an amplitude and a time/angle is specified by the technical data of a circuit and the embedded system (microcontroller) of the evaluation arrangement. For example, the factors are selected such that both signal components (amplitude and phase) are introduced into the combination signal sigX approximately with the same proportion across the measuring range of the CO2 calibration so that, e.g., the largest measuring resolution may be obtained in sigX. For example, the factors Ka and Kp are empirically determined in order to obtain, e.g., the best signal for sigX. For example, the constants Ka and Kp may depend on a concentration, a temperature, or a pressure of a gas to be analyzed. Thus, the amplitude information sigUss may be matched to the phase information SigPhi. It is possible that the evaluation arrangement may further process amplitude information and phase information together with the combination signal, for example, as a result of which the evaluation arrangement may very quickly, efficiently, and very precisely analyze the gas detected by the gas sensor.

According to an embodiment, the evaluation arrangement is configured to obtain the amplitude information sigUss according to sigUss=2*Hz.Uss−(D1.Uss+D2.Uss). The term Hz.Uss may be information about a heater amplitude, the term D1.Uss may be the information about the amplitude of the detector signal of the first detector, and D2.Uss may be the information about the amplitude of the detector signal of the second detector. Thus, the amplitude information sigUss may constitute a relative amplitude signal. In other words, the amplitude information may be a difference of twice the heater amplitude and of a sum of the information about the amplitude of the detector signal of the first detector and the information about the amplitude of the detector signal of the second detector. This particular calculation of the amplitude information sigUss may achieve that the amplitude information sigUss essentially depends on a heat transfer by the fluid, and that unknown heat transfers, e.g., from the at least one heater into the gas to be analyzed and from the gas to be analyzed into the first and/or second detector are not, or only slightly, considered. Thus, the combination signal sigX, which may depend on the amplitude information sigUss, is not, or only slightly, affected by unknown heat transfers, as a result of which the evaluation arrangement may very precisely determine properties of the gas to be analyzed such as the information about the gas concentration or the information about the thermal diffusivity of the fluid.

According to an embodiment, the evaluation arrangement may be configured to calculate a polynomial (e.g. of a first degree, e.g. A.y(sigX)) of the combination signal in order to obtain the information about the gas concentration or the information about the thermal diffusivity of the fluid. Through the polynomial formation of the combination signal by the evaluation arrangement, a drift correction of the combination signal may be performed. Thus, for example, a concentration drift, a pressure drift, and a temperature drift may be corrected by the polynomial formation. Thus, for example, the evaluation arrangement may calculated three polynomials of the combination signal, wherein a first polynomial may represent a relationship between the gas concentration and the combination signal, a second polynomial may represent a relationship between a pressure and a signal shift (pressure drift of the combination signal), and a third polynomial may represent a relationship between a temperature and a pressure drift. Thus, through this feature, possible inaccuracies may be corrected, and the evaluation arrangement may therefore be configured to analyze the fluid very precisely with a reduction of possible errors.

According to an embodiment, the evaluation arrangement may be configured to multiply a polynomial of the combination signal with a correction term in order to obtain the information about the gas concentration or the information about the thermal diffusivity. The correction term may depend on the combination signal, on information about a pressure (p), and on information about a temperature (T). Thus, for example, the correction term may compensate for a pressure/temperature dependence of the combination signal. Thus, for example, a polynomial representing a relationship between a gas concentration and the combination signal may be corrected with the correction term with respect to a pressure and temperature drift. Thus, by multiplying the correction term with the polynomial of the combination signal, a reduction of possible influences of errors may be performed by the evaluation arrangement, as a result of which the evaluation arrangement may be configured to very precisely obtain information about the gas concentration or information about the thermal diffusivity. For example, this may minimize pressure-dependent and temperature-dependent errors created in the detection of a detector signal by the first detector and/or the second detector of the gas sensor, for example.

According to an embodiment, the evaluation arrangement may be configured to perform a calculation according to $$C = pol(sigX) \cdot \left(1 - \left[\frac{f(p)}{sigX - const1}\right] \cdot \left(1 - \left[\frac{f(T)}{p - const2}\right]\right)\right)$$

in order to obtain information C about the gas concentration. The term sigX may be the combination signal, the term pol(sigX) may be a polynomial of the combination signal sigX, f(p) may be a function of the pressure p (or of a pressure p measured in a surrounding area of the thermal gas sensor), const1 may be a first constant, f(T) may be a function of the temperature (or a temperature T measured in a surrounding area of the thermal gas sensor), and const2 may be a second constant. For example, the function f(p) may be a polynomial that may represent a relationship between a pressure and a signal shift, and f(T) may be a polynomial that may represent a relationship between a temperature and a signal shift. With this feature, the polynomial of the combination signal may be corrected with respect to pressure-dependent and/or temperature-dependent errors caused by the gas sensor, or these may be reduced, as a result of which a very precise gas analysis by the evaluation arrangement is made possible.

According to an embodiment, the evaluation arrangement may be configured to perform a calculation according to in $$C[vol\ \%] = A.y(sigX) \cdot \left(1 - \left[\frac{B.y(p) - B.ref}{sigX - B.ref}\right] \cdot \left(1 - \left[\frac{C.y(T) - C.ref}{p - C.ref}\right]\right)\right)$$

order to obtain the information C about the gas concentration. The term sigX may be the combination signal, A.y (sigX) may be a polynomial (e.g. of the first order) of the combination signal sigX, B.y(p) may be a function of the pressure p (or of a pressure p measured in a surrounding area of the thermal gas sensor), B.ref may be a constant, C.y(T) may be a function of the temperature T (or of a temperature T measured in a surrounding area of the thermal gas sensor), and C.ref may be a second constant. Here, for example, B.y(p) may be a polynomial function (e.g. of the second order) that may represent a relationship between the pressure p and a signal shift (e.g. of the combination signal sigX). For example, the function C.y(T) is a polynomial function (e.g. of the second order) that may represent a relationship between the temperature T and a pressure shift, for example. Thus, the evaluation arrangement is configured to, e.g., very precise determine information about the gas concentration of a fluid to be analyzed, since the function B.y(p) of the pressure p and the function C.y(T) of the temperature T may form a correction term that may correct the combination signal sigX.

According to an embodiment, the evaluation arrangement may be configured to consider a pressure and/or a temperature in a surrounding area of the thermal gas sensor when determining the information about the gas concentration. To this end, for example, the evaluation arrangement may obtain information about the pressure and/or the temperature in the surrounding area of the gas sensor. For example, the pressure in the surrounding area of the thermal gas sensor is determined by a pressure sensor and the temperature in the surrounding area of the thermal gas sensor is determined by a temperature sensor, and they are transmitted to the evaluation arrangement, for example. The pressure sensor and/or the temperature sensor may be arranged in the surrounding area of the thermal gas sensor. Thus, it is possible that the evaluation arrangement performs corrections dependent on the pressure and/or the temperature, and may therefore very precisely analyze the fluid, and may therefore very precisely obtain information about the gas concentration and/or a thermal conductivity of the fluid, for example.

According to an embodiment, the evaluation arrangement may be configured, when determining the information about the gas concentration, to use as input quantities of a drift correction the combination signal, information about the temperature in a surrounding area of the thermal gas sensor, and information about a pressure in a surrounding area of the thermal gas sensor, and to obtain the information about the gas concentration as a result of the drift correction. Apart from the three mentioned input variables, for example, the drift correction does not obtain further variables, but only uses constants, for example, (e.g. additionally) obtained previously—for example in the context of a calibration. Thus, the evaluation arrangement may be configured to calculate out possible errors in the calculation of the gas concentration, caused by a drift, and to therefore perform a drift correction. The drift may be created at different temperatures and pressures and may therefore falsify a determination of the gas concentration, which may be avoided or suppressed with this feature. Thus, it is possible to very precisely determine information about the gas concentration with the evaluation arrangement.

According to an embodiment, the evaluation arrangement is configured to obtain the combination signal, or a further combination signal, on the basis of a quotient between amplitude information that depends on the information about the amplitude of the detector signal at least of the first detector and optionally also on the information about the amplitude of the detector signal of the second detector, and phase information that depends on the information about the first phase difference and optionally also on the information about the second phase difference. In addition, the evaluation arrangement may be configured to determine, dependent on the combination signal, information about a concentration of a gas, e.g. a third gas of a gas mixture. In other words, the quotient is a ratio between the information about the amplitude and the phase information. According to an embodiment, the third gas shifts this ratio, as a result of which the evaluation arrangement may be configured to infer the concentration of the third gas component on the basis of this ratio.

According to an embodiment, the evaluation arrangement is configured to obtain the combination signal sigV according to $$sigV = sigUss*Kav/(sigPhi*Kpv)$$

In the equation, sigUss may be amplitude information that depends on the information about the amplitude of the detector signal of the first detector and optionally on the information about the amplitude of the detector signal of the second detector. In addition, sigPhi may be phase information that depends on the information about the first phase difference and optionally on the information about the second phase difference. In addition, Kav and Kpv represent constants. For example, the combination signal sigV represents the ratio between the information about the amplitude and the phase information. In other words, the evaluation arrangement is configured to determine, by means of the ratio sigV, from an amplitude signal and a phase signal a further physical gas parameter that may be used to infer, by means of the evaluation arrangement, e.g. by correlation, the unknown concentration of a known third gas in the gas mixture to be analyzed. Kav and Kpv are new weighting factors that amplify changes in the ratio of the amplitudes and phases.

According to an embodiment, the evaluation arrangement is configured to obtain information as to how much heat is dissipated by the heater during a heating period, and to determine, dependent on the information as to how much energy is dissipated by the heater during the heating period, information about a concentration of a gas, e.g. a third gas of a gas mixture. A heating period may be understood to be a duration from a first zero crossing of a heating voltage to a second zero crossing of the heating voltage. Alternatively, the heating period may also be understood to be a duration starting from a first point in time at which the heating voltage changes from zero volts to more than or less than zero volts, up to a second point in time at which the heating voltage changes from more than or less than zero volts to zero volts. For example, the heating signal may be a sinusoidal signal, a cosine signal, a square-wave signal, a triangular wave signal or a sawtooth signal. The heat is dissipated to the gas mixture surrounding the heater during the heating period. The amount of heat that is dissipated by the heater to the surrounding gas depends on, e.g., a thermal conductivity of the surrounding gas, or a thermal conductivity of gas components of the surrounding gas. Thus, the evaluation arrangement may be configured to determine, by means of the heat dissipated by the heater, a thermal conductivity of the unknown gas or gas mixture.

According to an embodiment, the evaluation arrangement is configured to obtain the information as to how much heat is dissipated by the heater during a heating period on the basis of a measurement of a current flow through the heater at a specified heating voltage. In other words, the heating voltage applied at the heater is specified during the heating period, and the current flow changes according to how much heat is dissipated to the gas or gas mixture. The larger the amount of heat that is dissipated, the weaker the increase of the temperature of the heater and therefore, assuming a positive TCR (temperature coefficient of resistance), the value of the heater resistance, as a result of which the current flow decreases less. Thus, by determining the current flow through the heater by means of the evaluation arrangement, a composition of the gas mixture to be analyzed may be inferred, or the current flow may be used as additional information by the evaluation arrangement to further improve an accuracy in the gas analysis.

According to an embodiment, the evaluation arrangement is configured to obtain the current flow shortly after switching on the specified heating voltage and shortly before switching off the specified heating voltage. The evaluation arrangement may determine a change of the current flow during the heating period from a difference of both of these current flow data pieces. The larger the difference, the lower the thermal conductivity of the gas or gas mixture to be analyzed. Thus, the evaluation arrangement is configured to use the thermal conductivity of the gas or gas mixture, e.g., as an additional parameter in an analysis of the gas or gas mixture. In other words, the evaluation arrangement may be configured to use the measurement of the thermal conductivity as a further physical parameter of the unknown gas mixture, through the evaluation arrangement being configured to, for example, evaluate (per period) the difference of the heater current at a starting maximum shortly after switching on the heating voltage and shortly before switching off the heating voltage. Shortly after switching on the heating voltage may signify a point in time in a time span from 10 μs to 1 ms, 100 μs to 800 μs, or 300 μs to 500 μs, such as 400 μs after the switch-on.

An embodiment provides a method for evaluating signals of a thermal gas sensor with at least one heater and at least one detector. For example, heat may be transferred from the heater to the detector via a gas to be analyzed. The method may include obtaining information about an amplitude of a detector signal of a first detector (e.g. D1.Uss) and information about a first phase difference between a heater signal and the detector signal of the first detector (e.g. (D1-Hz).phi). A combination signal may be formed as an intermediate quantity, dependent on the information about the amplitude of the detector signal and dependent on the information about the first phase difference. For example, the combination signal may combine amplitude information and phase information. Information about a gas concentration or information about a thermal diffusivity of a fluid (e.g. a gas or gas mixture) may be determined on the basis of the combination signal. For example, this determination may be carried out without separately considering the individual information incorporated into the combination signal in the further process of the calculations.

An embodiment provides a method for evaluating signals of a thermal gas sensor with at least one heater and two detectors arranged in different distances or the same distance to the heater. For example, heat may be transferred from the heater to the two detectors via a gas to be analyzed. The method may include obtaining information about an amplitude of a detector signal of a first detector (e.g. D1.Uss), information about an amplitude of a detector signal of a second detector (e.g. D2.Uss), information about a first phase difference between a heater signal and the detector signal of the first detector (e.g. (D1-Hz).phi), and information about a second phase difference between the heater signal and the detector signal of a second detector (e.g. (D2-Hz).phi). A combination signal may be formed as an intermediate quantity, dependent on the information about the amplitude of the detector signals and dependent on the information about the first phase difference and dependent on the information about the second phase difference. For example, the combination signal may combine amplitude information and phase information. Information about a gas concentration or information about a thermal diffusivity of a fluid (e.g. a gas or gas mixture) may be determined on the basis of the combination signal. For example, this determination may be carried out without separately considering individual information incorporated into the combination signal in the further process of the calculations.

An embodiment concerns an evaluation arrangement for a thermal gas sensor with at least one heater and at least one detector. For example, but not necessarily, the two detectors may be arranged in different distances to the heater. The evaluation arrangement may be configured to control, dependent on at least one sensor signal from at least one of the detectors, a heating power applied to the heater in order to bring the at least one sensor signal into a predetermined value range. In addition, the evaluation arrangement may be configured to consider information about the heating power (e.g. Hz.Uss) when deriving information about a gas concentration from the sensor signals.

This embodiment of the evaluation arrangement is based on the finding that the evaluation arrangement may vary the heating power in order to maintain the at least one sensor signal in the predetermined value range for different gases or gas mixtures. Due to the fact that the at least one sensor signal is maintained in the predetermined value range, it may analyze in an ideal manner, without having to accept large information losses. For example, if the evaluation arrangement obtains information as to the fact that an amplitude of the sensor signal is lower than the predetermined value range, the evaluation arrangement may apply a heating power to the heater so as to increase the heating power of the heater and to therefore lift the amplitude of the sensor signal into the predetermined value range. However, if the evaluation arrangement obtains information as to the fact that the sensor signal comprises an amplitude that is larger than the predetermined value range, the evaluation arrangement may apply a heating power to the heater so as to reduce the heating power of the heater and to therefore lower the amplitude of the sensor signal into the predetermined value range. Thus, for example, the evaluation arrangement may constantly maintain the at least one sensor signal in the predetermined value range by the fact that the evaluation arrangement applies heating power to the heater, or readjusts the same, dependent on the at least one sensor signal. Thus, the evaluation arrangement may derive information about a gas concentration and/or a thermal diffusivity of a gas using a combination of the information about the heating power and the information about the sensor signals. In addition, the evaluation arrangement may therefore enable a precise flow measurement and a quick gas analysis.

According to an embodiment, the evaluation arrangement may be configured to apply a periodic signal to the heater. For example, the periodic signals defines a square-wave signal, or an impulse with a defined power, or a sinusoidal signal. Optionally, the evaluation arrangement comprises a processor that may generate the periodic signal. Here, it is to be noted that, due to the timer structures evaluable in the processor, a square-wave signal may be generated temporally much more precisely than a synthetic sinusoidal signal that would be output by the processor on its digital/analog (DA) port. By applying the periodic signal to the heater, the two detectors each also detect a periodic sensor signal. However, the periodic sensor signals achieved in such a way may also differ in amplitude, offset, and phase position with respect to the periodic signal of the heater. From the information achieved by the evaluation arrangement, the evaluation arrangement may determine a thermal conductivity, thermal diffusivity, and—if the density of a gas (a gas to be analyzed by the thermal gas sensor) is known—also a specific thermal capacity. Thus, for example, information about a gas concentration and/or thermal conductivity/thermal diffusivity may be derived from the variation of the heating power, which may represent information about the heating power. Currently, if the heater of the thermal gas sensor comprises a low thermal mass, the periodic signal applied to the heater may be modulated by the evaluation arrangement with frequencies up to 300 Hz, since heat may be provided and dissipated quickly. Thus, a periodic signal enables a precise, quick, and efficient gas analysis.

For example, if the periodic signal is an impulse with a defined power, the electric crosstalk of the steep edges of the heater signal with respect to the detectors would be clearly temporally distinguishable from the thermal wave that occurs later in time. With a duty cycle of 50%, it is possible that the switch-off edge at the heater may electrically crosstalk into the sensor signal if the same simultaneously obtains the heat wave and the at least one detector performs a measurement. By configuring the electronic system (R-C components), the heater edges may be slightly rounded off, and the detector signals may be pushed outside of the crosstalk interferences. On a powerful embedded platform, a heater operation with a shorter duty cycle could become more important since the electric interference and the signal may be clearly temporally distinguished. Obviously, the pulse should be wide enough for the heater to dissipate enough power/heat so that the at least one detector may perform a measurement, which may be a lower limit of the duty cycle of 5%.

According to an embodiment, the evaluation arrangement may be configured to switch the heating power applied to the heater between two values. Thus, for example, heating power in the form of a periodic square-wave signal may be applied to the heater. For example, a DA converter may specify the two values (e.g. in the form of heater voltages). One of two voltages may alternately be applied to a heater amplifier with an analog switch. This feature makes it possible that the heating power and phase position present at the heater may be precisely determined at each point in time, as a result of which the at least one sensor signal may be compared very precisely to the heater signal, and the evaluation means may therefore perform a very precise gas analysis.

According to an embodiment, the evaluation arrangement may be configured to adjust an amplitude of the heating power such that a minimum value of the at least one sensor signal and a maximum value of the at least one sensor signal are in the predetermined value range. For example, this ensures that an amplitude of the at least one sensor signal is in the predetermined value range for the entire at least one sensor signal (e.g. for the entire time in which the thermal gas sensor has detected the at least one sensor signal via at least one of the two detectors). For example, the minimum value may represent a minimum amplitude of the at least one sensor signal, and the maximum value may represent a maximum amplitude. Thus, the amplitude of the heating power may be controlled at least twice, e.g. when verifying whether the minimum value of the at least one sensor signal is in the predetermined value range, and when verifying whether the maximum value of the at least one sensor signal is in the predetermined value range. Thus, the accuracy of the evaluation arrangement may be improved, since, with this feature, at least two values (a minimum value and the maximum value) of the at least one sensor signal may be determined, and the amplitude of the heating power may be adjusted based thereon. Accordingly, the evaluation arrangement may be configured to carry out a very precise gas analysis.

Optionally, the predetermined value range may comprise a minimum value range and a maximum value range. In this case, for example, the evaluation arrangement may be configured to control the amplitude of the heating power such that the minimum value of at least one sensor signal is in the minimum value range of the predetermined value range, and the maximum value of the at least one sensor signal is in the maximum value range of the predetermined value range. Thus, it is possible that the at least one sensor signal almost fully covers the entire value range and that only few, or no, information is lost, for example.

According to an embodiment, the minimum value and/or the maximum value of the at least one sensor signal may define a phase position or an offset of the at least one sensor signal.

For example, the predetermined value range may constitute an operating range of an analog-digital converter. If the minimum value of the at least one sensor signal and/or a maximum value of the at least one sensor signal is outside of the predetermined value range, the analog-digital converter may not correctly convert the at least one sensor signal, as a result of which the evaluation arrangement, under certain circumstances, derives incorrect information about the gas concentration or thermal diffusivity. This may be prevented or reduced through the feature described herein.

According to an embodiment, the evaluation arrangement may be configured to set or adjust an amplitude of the heating power such that an amplitude of the at least one sensor signal is in a specified amplitude range. For example, the specified amplitude range (e.g. which may be determined/defined by the predetermined value range) may constitute an operating range of an analog-digital converter. The amplitude of the at least one sensor signal should utilize at least 50%, or at least 65%, or at least 75% of the specified amplitude range so that a meaningful analysis of the at least one sensor signal may be carried out by the evaluation arrangement. Optionally, the specified amplitude range may also define that the amplitude of the at least one sensor signal utilizes at least 50%, at least 65%, or at least 75% of the value range of the analog-digital converter. If the amplitude of the at least one sensor signal is outside of the specified amplitude range, information may be lost, and an incorrect derivation of information about the gas concentration or thermal diffusivity may be obtained from the sensor signal, for example.

Similarly, there may be problems if the amplitude of the at least one sensor signal utilizes only a very small range of the specified amplitude range, e.g., since the analog-digital converter may not be fully utilized in this case and the quality of the analysis by the evaluation arrangement is reduced. A very high accuracy in an analysis of the at least one sensor signal by means of the evaluation arrangement may be ensured through the feature described. Thus, it is possible that the analog-digital converter may operate in optimized conditions, and a very precise gas analysis by the evaluation arrangement is ensured.

According to an embodiment, the evaluation arrangement may be configured to set or adjust sampling times at which a sensor signal is sampled. For example, the sensor signal may be a sensor signal that is pre-processed and/or applied with a DC offset. Through this, for example, the evaluation arrangement may set sampling times at which the evaluation arrangement expects the sensor signal to be in the predetermined value range. If the sensor signal is not in the predetermined value range, the evaluation arrangement may apply a heating power to the heater in order to bring the sensor signal into the predetermined value range at the sampling time. Thus, the evaluation arrangement is configured to set or adjust optimized sampling times at which the evaluation arrangement may perform a very quick and precise gas analysis of the gas detected by the thermal gas sensor.

According to an embodiment, the evaluation arrangement is configured to set the sampling times such that sampling is carried out at a point in time (e.g. a first sampling time) at which the sensor signal reaches a maximum value, and such that sampling takes place at a point in time (e.g. a second sampling time) at which the sensor signal reaches a minimum value. For example, sampling may be carried out with a phase difference of up to +/−0.5%, +/−1%, +/−2%, or +/−5%. According to an embodiment, sampling may be carried out at the point in time with a deviation of +/−15 µs, +/−100 µs, +/−2.1 ms, +/−4.2 ms, +/−6.3 ms or +/−10 ms. Due to the fact that the evaluation means may set the sampling times with such an accuracy, it is possible that the evaluation means may verify whether the minimum value and/or the maximum value captured in such a way is/are within the predetermined value range. In addition, the maximum value and the minimum value of the sensor signal may be compared very precisely to maximum values and minimum values, respectively, of the sensor signals of other gas types, as a result of which the evaluation arrangement is configured to perform a very precise and efficient gas analysis through the sampling times set in such a way.

According to an embodiment, the evaluation means may be configured to combine a sensor signal from at least one of the detectors with an offset signal generated by a digital-analog converter in order to obtain an input signal for the analog-digital converter. In addition, the evaluation means may be configured to adjust the offset signal in order to achieve that the input signal of the analog-digital converter remains within a specified range (e.g. the predetermined value range) during an entire period of the sensor signal. For example, the offset signal may be adjusted as a reaction to identifying that an input value of the analog-digital converter exceeds a specified upper threshold value (e.g. 95%, 90%, or 85% of a maximum processable input value of the analog-digital converter), or as a reaction to identifying that an input value of the analog-digital converter falls below a specified lower threshold value (e.g. 5%, 10%, or 15% of a maximum processable input value of the analog-digital converter).

Thus, for example, the offset signal may change an offset of the sensor signal to bring the sensor signal into the specified range. For example, it is to be noted that the offset signal may be used by the evaluation means to generate the input signal that may constitute an offset-shifted sensor signal. Thus, the evaluation arrangement may shift the sensor signal into the specified range during the entire period by means of a combination of the at least one sensor signal and the offset signal. For example, if the input signal still exceeds the specified range, the evaluation means may apply a heating power to the heater to bring the at least one sensor signal within the specified range during the entire period. For example, the specified range may constitute an operating range of an analog-digital converter. Thus, through the feature described herein, it is possible that very precise information about the gas concentration and/or the thermal diffusivity may be derived from the at least one sensor signal by means of the evaluation means, which may include the analog-digital converter.

According to an embodiment, the evaluation means may be configured to control the heating power only if the sampling times are set or adjusted in a steady state and if the offset signal is adjusted in a steady state. For example, a steady state is understood to mean that the evaluation means has determined the sampling times within possible tolerances and that the sampling times do not have to be further set or adjusted. For example, in the steady state, the sampling times are adjusted such that a maximum value (within tolerances) and a minimum value (within tolerances) of the at least one sensor signal are sampled. In addition, a steady state may define that the offset signal adjusted by the evaluation means generates in combination with the at least one sensor signal an input signal that remains within a specified range during the entire period of the sensor signal. Thus, the steady state may signify that the evaluation means has precisely determined all output parameters (e.g. the sampling times (and the maximum value and the minimum value of the sensor signals therefrom, for example) or the offset signal) in order to very precisely analyze the at least one sensor signal and derive information about the gas concentration and/or thermal diffusivity. From information about the heating power adjusted by the evaluation means and the information derived from the at least one sensor signal by means of the evaluation means, the evaluation means may very precisely determine information about the gas concentration and/or thermal diffusivity of the gas detected by the gas sensor.

According to an embodiment, the evaluation means may be configured to stop controlling the heating power while the sampling times are being set or adjusted and/or while the offset signal is being adjusted. Through this feature, errors when setting or adjusting the sampling times and/or when adjusting the offset signal may be reduced, and a very quick and efficient adjustment is possible, as a result of which the evaluation means may be configured to very quickly and very precisely determine information about the gas concentration and the thermal diffusivity.

According to an embodiment, the evaluation arrangement may be configured to control a mean heating power or a maximum heating power and an amplitude of the heating power. For example, since a periodic excitation signal may be applied to the heater, the mean heating power may be a power averaged over a time in which the excitation signal is applied to the heater, for example. In a periodically excited heater, the amplitude of the heating power may vary. Thus, for example, the maximum heating power may correspond to a maximum amplitude of the heating power of the heater within a time span. Alternatively, the amplitude of the heating power may also be approximately constant. Accordingly, for example, an amplitude of the heating power may be controlled to vary over time.

An embodiment provides a method for operating an evaluation arrangement for a thermal gas sensor with at least one heater and at least one detector or two detectors arranged in different distances to the heater or two detectors arranged in the same distance to the heater. The method may include controlling a heating power applied to the heater dependent on at least one sensor signal from at least one of the detectors in order to bring the at least one sensor signal into a predetermined value range. In addition, the method may include considering information about the heating power (e.g. Hz.Uss) when deriving information about a gas concentration from the sensor signals.

An embodiment concerns a computer program with a program code for performing a method when the program runs on the computer.

An embodiment concerns an evaluation arrangement for a thermal gas sensor with at least one heater and at least one detector or two detectors arranged in different distances to the heater or two detectors arranged in the same distance to the heater. The evaluation arrangement may be configured to apply to the heater a periodic signal with a specified period duration. In addition, the evaluation arrangement may be configured to sample at least one sensor signal from one of the detectors at three sampling times, wherein a second sampling time is time shifted by 90°, with respect to the period duration, compared to a first sampling time, and wherein a third sampling time is time shifted by 180°, with respect to the period duration, compared to the first sampling time. In addition, the evaluation arrangement may be configured to identify, on the basis of three sample values that are based on a sampling of the sensor signal at the first sampling time, the second sampling time, and the third sampling time, whether a first sample value or a third sample value constitute a maximum value and a minimum value of the sensor signal. The sampling times (e.g. the first sampling time, the second sampling time, and/or the third sampling time) may comprise a deviation of +/−0.5°, +/−1°, +/−2°, or +/−5° from the sampling time specified by the evaluation arrangement. Thus, the second sampling time may be time shifted compared to the first sampling time by a ¼ period duration, a 5/4 period duration, or a 9/4 period duration, and the third sampling time may be time shifted compared to the first sampling time by a ½ period duration, by a 3/2 period duration, or by a 5/2 period duration, for example.

This embodiment of the evaluation arrangement is based on the finding that an amplitude of the at least one sensor signal, detected by one of the at least two detectors of the thermal gas sensor that are arranged in different distances to the heater, may be measured very precisely if an analog-digital conversion of the at least one sensor signal is carried out at the right point in time. For example, this is the point in time at which the at least one sensor signal comprises the maximum value or the minimum value. The evaluation arrangement may be configured to identify that the first sampling time and the third sampling time are selected incorrectly, by the evaluation arrangement sampling the at least one sensor signal at the second sampling time at which a "zero crossing" of the at least one sensor signal is expected. If the first sampling time, the second sampling time, and the third sampling time are correct, the evaluation arrangement may identify whether the first sample value and the third sample value constitute a maximum value and a minimum value of the sensor signal. Thus, the second sampling time may ensure this verification for the evaluation arrangement.

In addition, it is possible to determine a value range (e.g. from the minimum value to the maximum value) of the sensor signals and to verify whether the same is in an operating range of the analog-digital converter so that the sensor signals may be analyzed in an optimized manner and there is only little, or no, loss of information. If the evaluation means asserts that the determined minimum value and maximum value are not within the value range, the evaluation arrangement may be configured to adapt the periodic signal applied to the heater in order to bring the sensor signals detected by the detectors into the value range.

In addition, the sampling times, in the form of the minimum value and/or the maximum value, constitute very precisely defined positions of the sensor signals, as a result of which phase differences and/or amplitude differences between the periodic signal of the heater and the at least one sensor signal from at least one of the detectors may be determined very precisely, easily and efficiently by the evaluation means. For example, the evaluation means may perform a very precise gas analysis from the phase differences and amplitude differences determined in such a way.

Thus, it is to be noted that the evaluation arrangement may perform a very precise, quick and efficient gas analysis of the gas detected by the thermal gas sensor, due to the fact that, for example, amplitudes (e.g. a minimum value, a maximum value) of the sensor signal (a signal detected by at least one of the two detectors, transferred from the heater via the gas) may be determined very precisely through the precise determination of the first sampling time, the second sampling time, and the third sampling time.

According to an embodiment, the evaluation arrangement may be configured to change sampling times dependent on identifying whether the first sample value and the third sample value constitute a maximum value and a minimum value of the sensor signal. To this end, the evaluation arrangement may identify whether the sampling times are selected incorrectly. In this case, the first sample value and the third sample value constitute a maximum value or a minimum value of the sensor signal, and if there is a deviation of the sampling time of less than ±0.5°, ±0.7°, or ±1° and/or less than ±10 μs, ±15 μs, or ±20 μs, for example, the evaluation means decides that a change of the sample values is not carried out. Thus, it is possible to correct the sampling times and to set them by means of the evaluation arrangement precisely enough that the evaluation arrangement may perform a very precise, quick and efficient analysis.

According to an embodiment, the evaluation arrangement may be configured to set or adjust the sampling times such that the first sample value constitutes an extreme value of the sensor signal, e.g. a maximum value or a minimum value, and the third sample value constitutes a second extreme value, e.g. the minimum value or the maximum value, of the sensor signal. For example, the second sample value may constitutes a mean value or DC component of the sensor signal (e.g. a zero crossing of the sensor signal). Thus, the evaluation arrangement may be configured to sample the at least one sensor signal and to verify whether the first sample value and the third sample value constitutes a maximum value or a minimum value of the sensor signal until the first sample value constitutes the first extreme value of the sensor signal and the third sample value constitutes the second extreme value of the sensor signal. Thus, this may ensure that the evaluation arrangement is adjusted such that an amplitude of the sensor signal may be determined very precisely. Thus, for example, the evaluation arrangement performs a very precise gas analysis of the gas detected by the thermal gas sensor.

According to an embodiment, the evaluation arrangement may be configured to, when setting or adjusting the sampling times, consider information about a point in time of a crossing of the sensor signal through a specified threshold value. For example, the specified threshold value may correspond to a DC component or a mean value of the sensor signal. For example, the time of the crossing of the sensor signal through the specified threshold value may correspond to the second sampling time. For example, the specified threshold value may define a "zero crossing" of the sensor signal, wherein the "zero crossing" may be provided with an offset. For example, if the evaluation arrangement combines the information about the point in time of the crossing of the sensor signal through the specified threshold value with the remaining two sampling times (e.g. the first sampling time and the third sampling time), the evaluation arrangement may quickly and easily verify, or identify, whether the first sample value and the third sample value correspond to the maximum value and the minimum value of the sensor signal. Thus, the sampling times may be determined very precisely and exactly by the evaluation arrangement, as a result of which a very precise gas analysis by the evaluation arrangement is possible.

According to an embodiment, the evaluation arrangement may be configured to verify whether a second sample value at the second sampling time is equal to a mean value of the first sample value at the first sampling time and the third sample value at the third sampling time, and to identify, dependent on the verification, whether the first sample value and the third sample value constitute a maximum value and/or a minimum value of the sample signal. According to an embodiment, the second sample value may deviate from the mean value with a tolerance of up to ±0.5%, ±1%, or ±5% of a difference between the first sample value and the third sample value. This feature enables that the evaluation arrangement identifies, with the help of the second sampling time, whether the first sample value and the third sample value correspond to the maximum value or the minimum value of the sensor signal. Thus, possible errors of the evaluation arrangement may be reduced when determining the first sample value, the second sample value, and the third sample value, and a very precise gas analysis may be performed.

According to an embodiment, the evaluation arrangement may be configured to apply to the heater a periodic square-wave signal or an impulse with a defined power with a duty cycle of 50%. Alternatively, the duty cycle may be in a range from 5 to 50%. Here, for example, a tolerance of the duty cycle of ±1%, ±2%, or ±5% is possible. According to an embodiment, the evaluation arrangement may be configured to change the duty cycle at a fixed operating voltage of the heater in order to adapt a heating power of the heater. This makes it possible that the evaluation arrangement may determine a very precise heater signal via the duty cycle, and that a gas may be very precisely measured by determining the sampling times of the at least one sensor signal that corresponds to the heater signal (hence, the heater signal is transported to the detectors via the gas and is detected by the detector as a sensor signal, for example).

According to an embodiment, the evaluation arrangement may be configured to combine a sensor signal from at least one of the detectors with an offset signal generated by a digital-analog converter in order to obtain an input signal for an analog-digital converter and to adjust the offset signal in order to achieve that the input signal of the analog-digital converter remains within a specified range (e.g. a value range) during an entire period of the sensor signal. In addition, the evaluation arrangement may be configured to adjust the sampling times after adjusting the offset signal and, after a change of the sampling times, to again perform a verification as to whether sample values obtained with the changed setting of the sampling times are still within the specified range. For example, the analog-digital converter digitizes signal values present at the sampling times and therefore samples the sensor signal. For example, the evaluation means may adjust the offset signal as a reaction to detecting that an input value of the analog-digital converter exceeds a specified upper threshold value (e.g. 95%, 90%, or 85%) of a maximum processable input value of the analog-digital converter), or as a reaction to detecting that an input value of the analog-digital converter falls below a specified lower threshold value (e.g. 5%, 10%, or 15% of a maximum processable input value of the analog-digital converter). For example, the sampling times may be adjusted in the context of tracking the sampling times after adjusting the offset signal. For example, using the offset signal may achieve that the input signal combined of the sensor signal and the offset signal remains within the specified range, for example, wherein the specified range may be defined as a limit of the analog-digital converter that may be captured (e.g. an operating range of the analog-digital converter).

For example, the offset signal may amplify or reduce the sensor signal and therefore continuously keep the same (e.g. during the entire period) in an optimum operating range or operating window (e.g. in the specified range) of the analog-digital converter.

The specified range in which the input signal of the analog-digital converter is to remain during the entire period of the sensor signal may define a specified range for an amplitude of the sensor signal and for an offset of the sensor signal. Thus, for example, the offset signal may not only bring an offset of the sensor signal into the specified range of the analog-digital converter, but it may also control an amplitude of the sensor signal such that the input signal comprises an amplitude adopting a large part of the specified range with respect to the amplitude. If the evaluation arrangement has changed the sampling times, the sampling times are again verified with the obtained sample values (or input values of the analog/digital converter). For example, the specified range in which the obtained sample values are to be located may be between the specified lower threshold value and the specified upper threshold value. Optionally, the evaluation arrangement may be configured to readjust, as needed, the offset signal and/or the heating power of the heater after again verifying the obtained sample values. Thus, the evaluation arrangement makes it possible that the sensor signal may be very precisely analyzed by an analog-digital converter since the sensor signal is converted with an offset signal into an input signal, for example, that may adopt an optimum operating range of the analog-digital converter (the specified range). This makes it possible to perform a very precise gas analysis with the evaluation arrangement.

According to an embodiment, the evaluation arrangement may be configured to control a heating power applied to the heater dependent on the at least one sensor signal from at least one of the detectors in order to bring the at least one sensor signal into a predetermined value range. In addition, the evaluation arrangement may be configured to consider information about the heating power (e.g. Hz.Uss) when deriving information about a gas concentration from the sensor signals. For example, the evaluation arrangement may be configured to control a heating power so that an amplitude of the sensor signal may be brought into the predetermined value range. Here, the amplitude may be the minimum value and/or the maximum value of the sensor signal, or a difference of the maximum value and the minimum value. For example, if the sensor signal has a very low amplitude, a heating power may be applied to the heater by the evaluation arrangement so that the sensor signal detected by a detector comprises an amplitude approximately covering at least the entire predetermined value range. For example, the predetermined value range may constitute an operating range of an analog-digital converter with which the sensor signal may be processed by the evaluation arrangement. Accordingly, for example, the evaluation arrangement may apply a heating power to the heater so that the at least one sensor signal adopts at least 70%, 75%, or 80% of the operating range of the analog-digital converter. The evaluation arrangement may be configured to determine, dependent on information about the heating power and dependent on information about the sensor signal, information about the gas concentration and/or the thermal diffusivity of the sensor signal. For example, the information about the heating power may define an amplitude of the heating power, a phase of the heating power, and/or an offset of the heating power. For example, the information about the sensor signal may define an amplitude of the sensor signal, a phase of the sensor signal, and/or an offset of the sensor signal. Thus, a gas may be very precisely analyzed with the evaluation arrangement.

An embodiment provides a method for operating a thermal gas sensor with at least one heater and two detectors arranged in different distances to the heater. The method may include applying to the heater a periodic signal with a specified period duration. At least one sensor signal may be sampled by one of the detectors at three points in time, wherein a second sampling time may be time-shifted by 90°, with respect to the period duration (e.g. +/−2% or +/−2°), compared to a first sampling time (i.e. by a ¼ period duration, a 5/4 period duration, or by a 9/4 period duration), and wherein a third sampling time may be time-shifted by 180°, with respect to the period duration (e.g. +/−2% or +/−2°), compared to the first sampling time (i.e. by a ½ period duration, a 3/2 period duration, or by a 5/2 period duration). On the basis of three sample values that are based on sampling the sensor signal at the first sampling time, at the second sampling time, and at the third sampling time, it may be identified (e.g. by an evaluation arrangement) whether a first sample value and a third sample value constitute a maximum value or a minimum value of the sensor signal (e.g. except for a DC offset). The first sample value and the third sample value constituting a maximum value and a minimum value of the sensor signal may signify that the first sample value constitutes a maximum value and the third sample value constitutes a minimum value, for example, or that the first sample value constitutes a minimum value and the third sample value constitutes a maximum value (this applies to all embodiments described herein).

An embodiment concerns a computer program with a program code for performing a method when the program runs on a computer.

BRIEF DESCRIPTION OF THE DRAWINGS

Embodiments of the present invention will be detailed subsequently referring to the appended drawings, in which.

DETAILED DESCRIPTION OF THE INVENTION

Figure 1A:
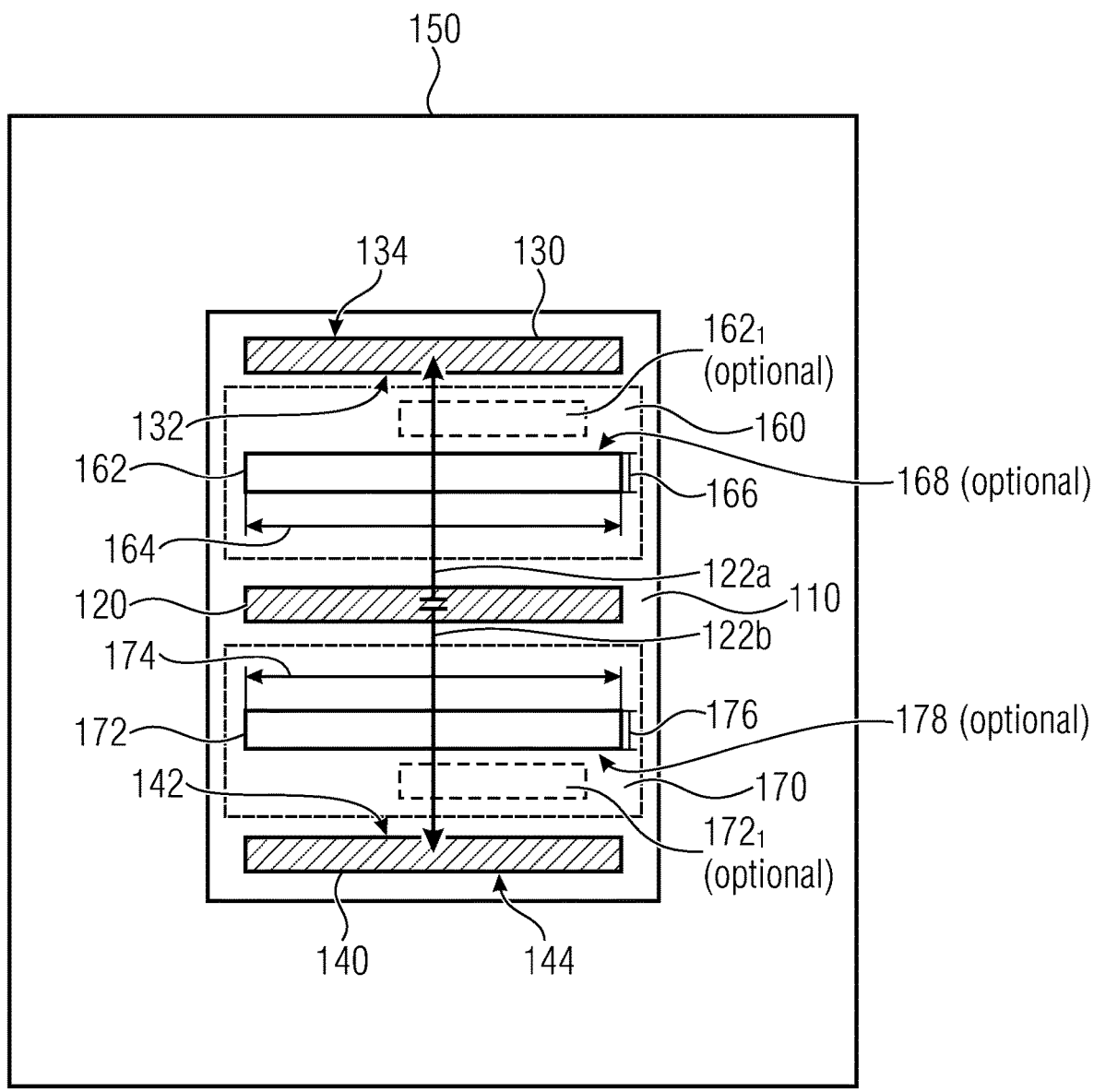
FIG. 1a shows a schematic illustration of a gas sensor according to an embodiment of the present invention.

Before embodiments of the present invention are subsequently described in more detail based on the drawings, it is to be noted that elements, objects, and/or structures that are identical, functionally identical or have the same effect are provided in the different drawings with the same or similar reference numerals so that the description of these elements illustrated in different embodiments may be interchangeable or applicable to each other.

FIG. 1 shows a schematic illustration of a gas sensor 100 according to an embodiment of the present invention. The gas sensor 100 may comprise a membrane 110 (e.g. a thin-layer membrane), a heating element 120, a first thermal element structure 130, and a second thermal element structure 140. Optionally, the gas sensor may only comprise the first thermal element structure 130 or the second thermal element structure 140. The membrane 110 may be spread out by a frame 150 and may comprise a first discontinuation area 160 and a second discontinuation area 170. The first discontinuation area 160 of the membrane 110 may comprise at least one discontinuation 162, and the second discontinuation area 170 of the membrane 110 may also comprise at least one discontinuation 172. For example, the heating element 120 may be arranged as a self-supporting bridge structure on the membrane 110 between the first discontinuation area 160 and the second discontinuation area 170 of the membrane 110. The first thermal element structure 130 may comprise a hot end 132 and a cold end 134. The hot end 132 of the first thermal element structure 130 may be arranged on the membrane 110 on a side of the first discontinuation area 160 opposite to the heating element 120. The second thermal element structure 140 may also comprise a hot end 142 and a cold end 144. The hot end 142 may be arranged on the membrane 110 on a side of the second discontinuation area 170 opposite to the heating element 120.

The membrane 110 may be a thin-layer membrane with a thickness between 200 nm and 4000 nm, 300 nm and 3000 nm, 400 nm and 2000 nm, or 1 μm and 10 μm. According to an embodiment, the thickness of the overall membrane is approximately 2 μm (e.g., it consists of several membrane layers, sensor layers, and passivation layers). For example, the membrane layer may comprise Si oxide and/or Si nitride. For example, an expansion of the membrane 110 into the sheet plane, i.e. perpendicular to a surface of the membrane 110 on which the heating element 120, the first thermal element structure 130, and the second thermal element structure 140 are arranged, may be defined as the thickness. The membrane 110 may comprise a conducting material, an insulating material, or a semiconductor material, wherein the material may comprise a very low thermal conductivity of below 5 W/(m*K), below 100 mW/(m*K), or below 50 mW/(m*K), for example. For example, a semiconductor with adapted basic doping may serve as a cost-efficient substrate for manufacturing the membrane 110 in a simple five mask MEMS process.

According to an embodiment, the heating element 120 (in the following, the heating element 120 may also be referred to as a heater) may form a self-supporting bridge structure and/or may include a wire. According to an embodiment, the heating element 120 may be spread out from one side of the frame 150 to an opposite side of the frame 150. For example, a voltage may be applied to the heating element 120, as a result of which the heating element 120 may transmit a heating power to a gas to be analyzed, e.g., that is located in the first discontinuation area 162 and/or in the second discontinuation area 172. For example, the voltage applied to the heating element 120 may be a periodic voltage signal such as a sinusoidal signal or a periodic square-wave signal. Thus, for example, the heating element 120 may provide a periodic heater signal (e.g. the heating power). For example, the heater signal may be transmitted to the first thermal element structure 130 and/or the second thermal element structure 140 via the membrane 110 and/or via a gas located in the first discontinuation 162 or the second discontinuation 172, for example.

For example, the first thermal element structure 130 and/or the second thermal element structure 140 are configured to be meander-shaped, which may correspond to thermal elements connected in series and forming a thermopile, for example. Thus, the first thermal element structure 130 and/or the second thermal element structure 140 may serve as a detector, wherein the first thermal element structure 130 and/or the second thermal element structure 140 may detect the heater signal, for example.

According to an embodiment, the first thermal element structure 130 and/or the second thermal element structure 140 may be arranged entirely on the membrane 110, or may be arranged at least partially on the membrane 110 and at least partially on the frame 150. Thus, for example, a temperature of the frame 150 may be used as a comparison temperature (e.g. the cold ends 134 of the first thermal element structure 130 may be arranged here and/or the cold ends 144 of the second thermal element structure 140 may be arranged here), and the part of the thermal element structure arranged on the membrane 110 (e.g. the hot ends 132, 142) may detect a measurement temperature (e.g. the heater signal). For example, the hot ends 132, 142 and the cold ends 134, 144 are connected via conductor. Thus, for example, a conductor including a first material may connect a first cold end to a first hot end, and a second conductor including a second material may connect the first hot end to a second cold end. This connection of a first conductor and a second conductor may constitute a thermal element, e.g., which may be connected in series to form a thermopile and which therefore may constitute the first thermal element structure 130 or the second thermal element structure 140, for example. Thus, for example, a temperature difference (e.g. between the comparison temperature and the measurement temperature) may occur along these conductors, as a result of which, e.g., an electric voltage may be induced at the ends (e.g. the hot ends and/or the cold ends) of the metal conductors. Thus, for example, the first thermal element structure 130 and/or the second thermal element structure 140 may be configured to convert heat into electrical energy. According to an embodiment, the first thermal element structure 130 and/or the second thermal element structure 140 may be a wire or a self-supporting bridge structure.

According to an embodiment, the membrane 110 may be spread out by the frame 150 made of a carrier material that is implemented such that the coefficient of temperature expansion and/or a thermal conductivity of a membrane material deviates from the coefficient of thermal expansion and/or the thermal conductivity of the carrier material. The frame 150 may comprise a carrier material or a substrate material with which the membrane 110 may be carried, for example, Thus, for example, a comparison temperature may be set at the frame 150. According to an embodiment, the frame 150 and the membrane 110 may also comprise the same coefficient of thermal expansion.

According to an embodiment, the membrane 110 may comprise a lower thermal conductivity than the frame 150. In this case, for example, the membrane 110 should in particular comprise a very low thermal conductivity so that the heater signal is transmitted from the heating element 120 to the first thermal element structure 130 and/or to the second thermal element structure 140 mainly via the gas to be analyzed (e.g. arranged in the first discontinuation 162 and/or in the second discontinuation 172) instead of via the membrane 110. Thus, for example, a heat transport via the membrane 110 may be suppressed, reduced, or slowed down.

Thus, the membrane 110 may be configured to suppress parasitic thermal conduction from the heating element 120 to the first thermal element structure 130 and/or to the second thermal element structure 140. Thus, for example, the thermal conductivity of the membrane 110 may be selected such that little to no heat is conducted from the heating element 120 to the first thermal element structure 130 and/or the second thermal element structure 140 via the membrane 110 and such that a majority of the heat, or the entire heat, is conducted via the gas to be analyzed.

On the other hand, the thermal conductivity of the carrier material of the frame 150 holding the membrane 110 may be very high. Thus, for example, silicon having a thermal conductivity of 150 W/(m*K) may be used as the carrier material. Thus, the carrier material may be used as a heat sink. Thus, for example, the first thermal element structure 130 and/or the second thermal element structure 140 is arranged partially, e.g. with the hot ends 132, 142, on the membrane and at least partially, e.g. with the cold ends 134, 144, on the carrier material, as a result of which a temperature difference may occur within the first thermal element structure 130 and/or the second thermal element structure 140, with the help of which the heat transport from the heating element 120 to the respective thermal element structure 130, 140 may be detected.

Thus, according to an embodiment, the cold ends of the first thermal element structure 130 and the cold ends of the second thermal element structure 140 may be arranged on the carrier material of the frame 150. For example, they are located where the membrane 110 is carried by the carrier material.

According to an embodiment, the first discontinuation area 160 of the membrane 110 may comprise a continuous discontinuation 162 whose longitudinal expansion 164 is large enough to fully cover the area between the first thermal element structure 130 and the heating element 120. The second discontinuation area 170 of the membrane 110 may comprise a continuous discontinuation 172 whose longitudinal expansion 174 is large enough to fully cover the area between the second thermal element structure 140 and the heating element 120. Thus, for example, the longitudinal expansion 164, 174 is as large as the entire length of the heating element 120 and/or at least as large as the entire length of the first thermal element structure 130 and/or the second thermal element structure 140. Thus, this makes it possible to transmit as little heat as possible from the heating element 120 to the first thermal element structure 130 or the second thermal element structure 140 via the membrane 110, but a majority is transmitted via a gas in the first discontinuation 162 in the first discontinuation area 160 and/or in the second discontinuation 172 in the second discontinuation area 170.

According to an embodiment, the lateral expansion 166 of the at least one discontinuation 162 of the first discontinuation area 160 may differ from the lateral expansion 176 of the at least one discontinuation 172 of the second discontinuation area 170. For example, the lateral expansion 166, 176 of the first discontinuation 162 and the second discontinuation 172, respectively, may be directed in a direction perpendicular to the a direction of a maximum expansion of the heating element 120, or in a direction from the heating element 120 to the respective thermal element structure (e.g. the first thermal element structure 130 and/or the second thermal element structure 140). For example, according to FIG. 1a, the first discontinuation 162 and the second discontinuation 172 comprise the same lateral expansion 166, 176.

According to an embodiment, the first discontinuation 162 may comprise a longitudinal expansion 164 and a lateral expansion 166 so that the first discontinuation 162 corresponds to the expansions of the first discontinuation area 160. Similarly, for example, the second discontinuation 172 may comprise a longitudinal expansion 174 and a lateral expansion 176 so that the second discontinuation 172 corresponds to the expansions of the second discontinuation area 170. Thus, for example, the entire first discontinuation area 160 may constitute the first discontinuation 162, and the entire discontinuation area 170 may constitute the discontinuation 172.

Optionally, on the side of the cold ends 134, 144 of the first thermal element structure 130 and/or the second thermal element structure 140, the membrane 110 may comprise a third and/or a fourth discontinuation area. Thus, for example, the first thermal element structure 130 may be arranged in the form of a wire or as a self-supporting bridge structure between the first discontinuation area 160 and a third discontinuation area, and/or the second thermal element structure 140 may be arranged as a wire or as a self-supporting bridge structure between the second discontinuation area 170 and the fourth discontinuation area, for example. Thus, for example, the first thermal element structure 130 and/or the second thermal element structure 140 may be surrounded from two sides by the gas to be analyzed.

According to an embodiment, the first thermal element structure 130 may comprise a different distance to the heating element 120 than the second thermal element structure 140. For example, in FIG. 1a, the first thermal element structure 130 comprises the same distance to the heating element 120 as the second thermal element structure 140. When transmitting the heater signal from the heating element 120 to the first thermal element structure 130 via the first discontinuation 162 and/or from the heating element 120 to the second thermal element structure 140 via the second discontinuation 172, unknown heat transfers may occur from the heating element into the gas to be analyzed that is arranged in the first discontinuation 162 and/or in the second discontinuation 172, and from the gas to the first thermal element structure 130 and/or the second thermal element structure 140. For example, the heater signal from the heating element 120 that is detected by the first thermal element structure 130 may be referred to as first sensor signal, and the heater signal from the heating element 120 that is detected by the second thermal element structure 140 may be referred as second sensor signal, for example.

For example, the first sensor signal and/or the second sensor signal may comprise the two unknown heat transitions (e.g. heating element→gas, gas→thermal element structure) and a heat transfer via the gas to be analyzed. If the first thermal element structure 130 is spaced apart from the heating element 120 differently than the second thermal element structure 140, for example, the gas sensor may create a difference signal from the first sensor signal and the second sensor signal, e.g., in which the unknown heat transitions (the first sensor signal and the second sensor signal may comprise the same heat transitions) may be subtracted out, and the difference signal therefore only, or to a large part, comprises the heat transfer from the heating element 120 to the respective thermal element structure 130, 140 via the gas to be analyzed, but does not, or only to a very small part, comprise the unknown heat transfers.

According to an embodiment, the first discontinuation area 160 and the second discontinuation area 170 may comprise several discontinuations (e.g. the discontinuation 162 and the discontinuation $162_1$, or the discontinuation 172 and the discontinuation $172_1$) that may be arranged such that (e.g. by the remaining membrane material 110) a grid structure is created (e.g. in the first discontinuation area 160 or the second discontinuation area 170) in which the discontinuations are arranged in rows in parallel to the heating element 120, and the rows are arranged to be offset to each other. In this case, the discontinuations in a discontinuation area 160, 170 may differ from each other with respect to the longitudinal expansion 164, 174 and the lateral expansion 166, 176. For example, according to FIG. 1a, the discontinuation $162_1$ of the first discontinuation area 160 comprises a smaller longitudinal expansion than the longitudinal expansion 164 of the discontinuation 162. Similarly, the discontinuation $172_1$ of the second discontinuation area 170 may comprise a smaller longitudinal expansion than the longitudinal expansion 174 of the discontinuation 172.

According to an embodiment, the first discontinuation area 160 and the second discontinuation area 170 may comprise several discontinuations that may be arranged such that a grid structure is created in which a path of a heat conduction by the membrane 110 is longer than a direct path 122a, 122b. For example, the direct path 122a, 122b may be a straight path perpendicular to the heating element 120, from the heating element 120 to the thermal element structure 130, 140. In this case, the direct path 122a, 122b may pass through the discontinuations 162 and $162_1$ and the discontinuations 172 and $172_1$, respectively, as a result of which a heat conduction by the gas to be analyzed may be sensed by the first thermal element structure 130 and/or the second thermal element structure 140. If the direct path 122a, 122b were to take place only via the membrane 110 and not via the gas to be analyzed, the gas sensor 100 could not ensure a meaningful analysis of the gas.

According to an embodiment, the at least one discontinuation 162, 172 may form rectangular cutouts with optionally rounded corners in the first discontinuation area 160 and the second discontinuation area 170. In this case, for example, it is a longitudinal hole. For example, it may also be an oval hole. Even though the discontinuation 162 of the first discontinuation area 160 and the discontinuation 172 of the second discontinuation area 170 are illustrated as rectangular discontinuations (holes) in FIG. 1a, the discontinuations may comprise any shapes (such as triangular, circular, square, polygon-shaped, etc.). The shaping of the discontinuations 162, 172 may be adapted such that a heat path from the heating element to the first thermal element structure 130 and/or to the second thermal element structure 140 via the membrane 110 is as long as possible, and a path via the gas to be analyzed constitutes a very long route. Thus, this makes it possible to transport as much heat as possible via the gas to be analyzed and not via the membrane 110, as a result of which the gas sensor 100 may very precisely analyze the gas.

According to an embodiment, the at least one discontinuation 162, 172 may be at least three times longer than it is wide. Thus, for example, the longitudinal expansion 164 of the discontinuation 162 may be three times longer than the lateral expansion 166, or the longitudinal expansion 174 of the discontinuation 172 may be three times longer than the lateral expansion 176. Thus, for example, the length constitutes the longitudinal expansion 164, 174, and the width constitutes the lateral expansion 166, 176, for example. For example, the length may be defined as a direction in parallel to the heating element 120 (or to a direction of maximum expansion of the heating element 120), and the width may be defined as a direction perpendicular to the heating element 120 (or to a direction of maximum expansion of the heating element 120).

According to an embodiment, a distance 168 between several discontinuations 162, $162_1$ in the first discontinuation area 160, and a distance 178 between several discontinuations 172, $172_1$ in the second discontinuation area 170 may correspond to the smallest realizable structural width that results in a mechanically durable grid structure. The distance 168, 178 may define a width of ridges between two discontinuations, and consisting of membrane material of the membrane 110. The smaller the distance 168, 178, the less heat is transferred via the membrane 110 from the heating element 120 to the first thermal element structure 130 and/or the second thermal element structure 140, and the more heat is transferred via the gas to be analyzed.

According to an embodiment, the first thermal element structure 130 and the second thermal element structure 140 may be passivated with a protective layer. The protective layer may protect the first thermal element structure 130 and the second thermal element structure 140 against damages by the gas to be analyzed, and may therefore avoid possible inaccuracies of the gas sensor in the gas analysis due to damages of the first thermal element structure 130 and/or the second thermal element structure 140.

According to an embodiment, the hot end 132 of the first thermal element structure may reach up to an edge of the first discontinuation area 160 of the membrane 110, and the hot end 142 of the second thermal element structure 140 may reach up to an edge of the second discontinuation area 170 of the membrane 110. For example, the distance between the hot end 132 and the first discontinuation area 160, or the distance between the hot end 142 and the second discontinuation area 170, should not be larger than 0.5 mm, 100 nm, or 10 μm. For example, if the discontinuation 162 or the discontinuation 172 reaches up to this edge, the membrane 110 has only a very small distance between the respective hot ends and the respective discontinuation. This makes it possible that the membrane material of the membrane 110 does not or only slightly impair a detection of the heater signal by the first thermal element structure 130 or the second thermal element structure 140, as a result of which the gas sensor 100 may very precisely analyze the gas.

Figure 1B:
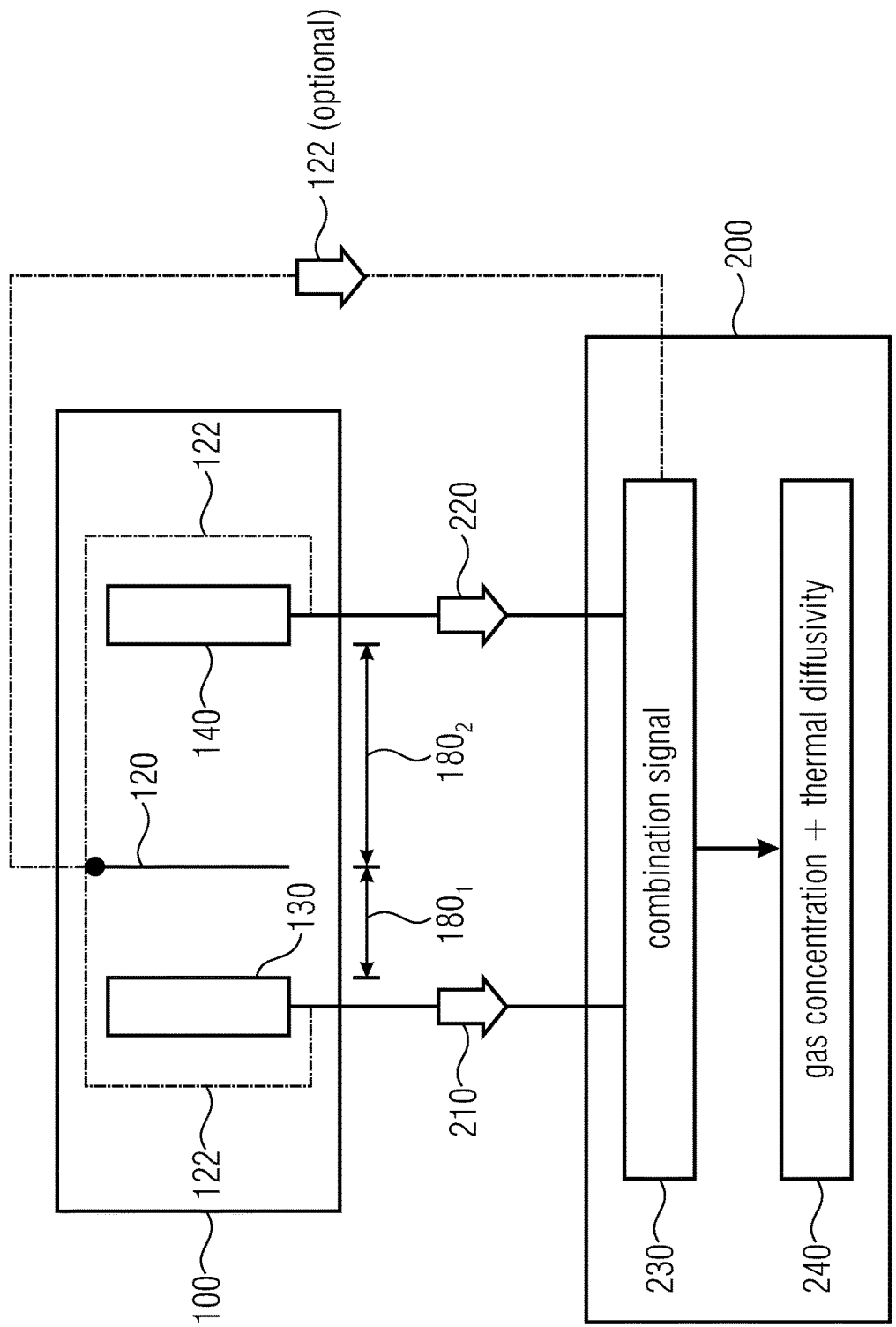
FIG. 1b shows a schematic illustration of an evaluation arrangement for a thermal gas sensor according to an embodiment of the present invention.

FIG. 1b shows a schematic illustration of an evaluation arrangement 200, which may also be referred to as evaluation means herein, for a thermal gas sensor 100 with at least one heater 120 and two detectors (a first detector 130 and a second detector 140) arranged in different distances $180_1$ and $180_2$ to the heater 120. The first detector 130 may be spaced apart from the heater 120 with a distance $180_1$, and the second detector 140 may be spaced apart from the heater 120 with a distance $180_2$. The evaluation arrangement 200 may be implemented to obtain information 210 about an amplitude of a detector signal of a first detector 130, information 220 about an amplitude of a detector signal of a second detector 140, information 210 about a first phase difference between a heater signal and the detector signal of the first detector 130, and information 220 about a second phase difference between the heater signal and the detector signal of the second detector 140.

According to an embodiment, the information 210 may include the amplitude of the detector signal of the first detector 130 as well as the first phase difference between the heater signal and the detector signal of the first detector 130, and the information 220 may include the amplitude of the detector signal of the second detector 140 as well as the second phase difference between the heater signal and the detector signal of the second detector 140. However, it is also possible that the amplitude of the detector signal of the respective detector (the first detector 130 and/or the second detector 140) is transmitted separately from the first phase difference and the second phase difference, respectively, from the thermal gas sensor to the evaluation arrangement. According to an embodiment, it is also possible that the information 210 and the information 220 are not transmitted via separate lines to the evaluation arrangement 200, but via a mutual line or wireless, for example.

According to an embodiment, the evaluation arrangement 200 may be implemented to form a combination signal 230 as an intermediate quantity dependent on the information 210, 220 about the amplitudes of the detector signals and dependent on the information 210, 220 about the first phase difference and the second phase difference. The combination signal 230 may combine amplitude information and phase information of the detector signal of the first detector 130 and of the detector signal of the second detector 140. The evaluation arrangement 200 may be implemented to determine information 240 about a gas concentration or a thermal diffusivity of a fluid, such as a gas or as a gas mixture, based on the combination signal 230. For example, the evaluation arrangement 200 may perform this determination without separately reconsidering the individual information 210, 220 incorporated into the combination signal 230 in the further process of the calculations.

For example, the amplitude of the detector signal may be directly provided as information 210, 220 by the respective detector 130, 140. The information 210, 220 about the first phase difference and the second phase difference between the heater signal 122 and the detector signal of the respective detector 130, 140 may be determined by the thermal gas sensor 100 and be transmitted to the evaluation arrangement 200, for example.

Alternatively, the detector signal of the first detector 130 and the detector signal of the second detector 140 may be transmitted to the evaluation arrangement 200 via the information 210 and the information 220, respectively, and the heater signal 122 may be additionally transmitted directly to the evaluation arrangement 200. In this case, the evaluation arrangement may be configured to determine the respective amplitude from the detector signal of the first detector 130 and from the detector signal of the second detector 140, and to determine the first phase difference and the second phase difference in order to form the combination signal 230 dependent on the information determined in such a way.

Due to the fact that the evaluation arrangement 200 forms the combination signal 230, the evaluation arrangement 200 may easily and much more quickly correct possible errors of the thermal gas sensor 100 to obtain the information 240 about the gas concentration and a thermal diffusivity, as would be the case if the evaluation arrangement 200 would separately correct the information 210 about the amplitude of the detector signal of the first detector 130 and the first phase difference as well as the information 220 about the amplitude of the detector signal of the second detector 140 and the second phase difference. Thus, the combination signal 230 may facilitate determining the information 240 about the gas concentration and the thermal diffusivity of the gas to be analyzed, and makes it possible to suppress or reduce errors generated by the thermal gas sensor 100.

According to an embodiment, the evaluation arrangement 200 may be configured to obtain information about a heater amplitude, such as information about a heating power, from the heater signal 122 and to form a linear combination of the information about the heater amplitude, the information 210 and the information 220 in order to obtain the combination signal 230.

Alternatively, the evaluation arrangement 200 may not only obtain the information about the heater amplitude from the heater signal 122 but may also, as described above, calculate information about the first phase difference and the second phase difference, e.g., if the information 210 includes the detector signal of the first detector 130 and the information 220 includes the detector signal of the second detector 140.

Thus, it is not only the phase of the heater signal that is incorporated into the combination signal 230 in the form of the first phase difference and the second phase difference, but also the heater amplitude, which makes it possible that the evaluation arrangement 200 may determine the information 240 about the gas concentration and the thermal diffusivity of the gas to be analyzed dependent on the first distance $180_1$ and the second distance $180_2$ of the two detectors from the heater 120. Thus, for example, the detector signal of the first detector 130 comprises a larger amplitude than the detector signal of the second detector 140 since the distance $180_2$ of the second detector 140 to the heater 120 is larger than the distance $180_1$ of the first detector 130 to the heater 120. With increasing distance to the heater 120, the heater amplitude detected by the respective detector 130, 140 may decrease. Due to the additional information about the heater amplitude, the evaluation arrangement 200 may therefore determine the information 240 about the gas concentration and the thermal diffusivity even more precisely since the heater amplitude of the heater signal 122 may be considered as a reference, and the combination signal 230 may therefore comprise a relative amplitude signal. For example, a relative amplitude signal is less error-prone than an absolute amplitude signal.

According to an embodiment, the evaluation arrangement 200 may be implemented to obtain the combination signal sigX 230 according to sigX=sigUss*Ka+sigPhi*Kp. The term sigUss may be amplitude information or an amplitude signal that may depend on the information 210 about the amplitude of the detector signal of the first detector 130 and on the information 220 about the amplitude of the detector signal of the second detector 140. For example, sigUss may be linear combination of the information 210 about the amplitude of the detector signal of the first detector 130 and the information 220 about the amplitude of the detector signal of the second detector 140. sigPhi may be phase information or an added phase signal that may depend on the information 210 about a first phase difference and on the information 220 about the second phase difference. Thus, for example, sigPhi may be an addition of the information 210 about the first phase difference and the information 220 about the second phase difference. Ka and Kp may be constants. The combination signal 230 determined in such a way may include amplitude information sigUss and phase information sigPhi, as a result of which four pieces of information (e.g. the information 210 about the amplitude of the detector signal of the first detector 130, the information 220 about the amplitude of the detector signal of the second detector 140, the information 210 about a first phase difference between the heater signal and the detector signal of the first detector 130, and the information 220 about the second phase difference between the heater signal and the detector signal of the second detector 140) may be combined in the combination signal 230, as a result of which the evaluation arrangement 200 may use less power for processing the information 210, 220. Thus, the evaluation arrangement 200 may be configured to determine information 240 about the gas concentration and thermal diffusivity very efficiently, quickly and precisely.

According to an embodiment, the evaluation arrangement 200 may be configured to obtain the amplitude information sigUss according to sigUss=2*Hz.Uss−(D1.Uss+D2.Uss). Hz.Uss may be information about the heater amplitude that may be obtained from the heater signal 122. D1.Uss may be information 210 about the amplitude of the detector signal of the first detector 130, and D2.Uss may be information 220 about the amplitude of the detector signal of the second detector 140. Thus, the amplitude information sigUss may constitute a relative amplitude signal since the information 210 about the amplitude of the detector signal of the first detector 130, the information 220 about the amplitude of the detector signal of the second detector 140, and the heater amplitude Hz.Uss are calculated with each other so that the information 210 about the amplitude of the detector signal of the first detector 130 and the information 220 about the amplitude of the detector signal of the second detector 140 may be considered relative to the heater amplitude. Due to the relative consideration of the amplitudes, possible errors of absolute amplitude values may be avoided, as a result of which the evaluation arrangement 200 may very precisely determine the information 240 about the gas concentration and thermal diffusivity.

According to an embodiment, the evaluation arrangement 200 may be implemented to calculate a polynomial, e.g. of the first degree, of the combination signal 230 in order to obtain the information 240 about the gas concentration or the thermal diffusivity. For example, the polynomial (e.g. polynomial y) may be obtained according to y=A0+A1*sigX+A2*sigX². Due to the polynomial formation of the combination signal 230 by the evaluation arrangement 200, the combination signal 230 may be corrected very easily and efficiently with respect to possible pressure drift errors or temperature drift errors.

According to an embodiment, the evaluation arrangement 200 may be implemented to multiply the polynomial of the combination signal 230 with a correction term in order to obtain the information 240 about the gas concentration and/or the thermal diffusivity. The correction term of the combination signal 230 may depend on information about a pressure and on information about a temperature and may compensate a pressure dependence and temperature dependence, for example. In other words, the correction term may compensate a pressure drift and/or a temperature drift from the combination signal 230. Thus, a possible incorrect interpretation by the evaluation arrangement 200 of the signals detected by the thermal gas sensor 100 may be reduced.

According to an embodiment, the evaluation arrangement 200 may be implemented to perform a calculation according to $$C = pol(sigX) \cdot \left(1 - \left[\frac{f(p)}{sigX - const1}\right] \cdot \left(1 - \left[\frac{f(T)}{p - const2}\right]\right)\right)$$

in order to obtain the information C 240 about the gas concentration. sigX may be the combination signal 230, pol(sigX) may be a polynomial of the combination signal sigX 230, f(p) may be a function of a pressure p, const1 may be a constant, f(T) may be a function of the temperature T, and const2 may be a second constant. f(p) may be a function of a pressure p measured in a surrounding area of the thermal gas sensor 100, and f(T) may be a function of a temperature T measured in a surrounding area of the thermal gas sensor 100. The second term of the multiplication $$\left(1 - \left[\frac{f(p)}{sigX - const1}\right] \cdot \left(1 - \left[\frac{f(T)}{p - const2}\right]\right)\right)$$

may also be understood as a correction term of the combination signal 230. The correction term may depend on measuring conditions of the gas sensor 100 (such as a surrounding pressure/measuring pressure, or a surrounding temperature/measuring temperature). Thus, the correction term may correct possible influences of a surrounding pressure or a surrounding temperature of the thermal gas sensor 100 on the determination of the information 240 about the gas concentration. Thus, a possible pressure drift or temperature drift may be suppressed.

According to an embodiment, the evaluation arrangement 200 may be implemented to perform a calculation according to $$C[vol \%] = A.y(sigX) \cdot \left(1 - \left[\frac{B.y(p) - B.ref}{sigX - B.ref}\right] \cdot \left(1 - \left[\frac{C.y(T) - C.ref}{p - C.ref}\right]\right)\right)$$

in order to obtain the information C 240 about the gas concentration. In the equation, sigX may be the combination signal 230, A.y(sigX) may be a polynomial of the combination signal sigX 230 (e.g. of the first order), B.y(p) may be a function of the pressure p (e.g. a polynomial function, such as of the second order), B.ref may be a constant, C.y(T) may be a function of the temperature T (e.g. a polynomial function, such as of the second order), and C.ref may be a second constant. For example, the function B.y(p) may be a function of a pressure p measured in a surrounding area of the thermal gas sensor 100, and the function C.y(T) may be a function of a temperature T measured in a surrounding area of the thermal gas sensor 100. The second term $$\left(1 - \left[\frac{B.y(p) - B.ref}{sigX - B.ref}\right] \cdot \left(1 - \left[\frac{C.y(T) - C.ref}{p - C.ref}\right]\right)\right)$$

of the multiplication for calculating the information C 240 about the gas concentration may define a correction term. In this case, for example, the correction term may depend on the pressure p and the temperature T. Thus, for example, B.y(p) may be a polynomial function dependent on the pressure p, for example, as a result if which a correction of possible pressure influences on the calculation of the information 240 about the gas concentration may be considered. Similarly, by forming the polynomial function C.y(T) as a function of the temperature T, a possible influence of the temperature T on the calculation of the information 240 about the gas concentration may be considered very precisely. By forming the polynomial function as a function of the pressure p and as a function of the temperature T, error corrections may be approximated very precisely, as a result of which the evaluation arrangement 200 may be implemented to determine the information 240 about the gas concentration very effectively and very precisely.

According to an embodiment, the evaluation arrangement 200 may be implemented to consider a pressure and/or a temperature in a surrounding area of the thermal gas sensor 100 when determining the information 240 about the gas concentration and/or the thermal diffusivity. To this end, for example, the thermal gas sensor 100 may comprise pressure sensors and temperature sensors with which it may detect the pressure and/or the temperature in the surrounding area and transmit the same to the evaluation arrangement 200. Thus, for example, the evaluation arrangement 200 may consider and correct possible incorrect calculations of the information 240 about the gas concentration and/or the thermal diffusivity due to different pressure conditions and/or temperature conditions in the surrounding area of the thermal gas sensor 100. Thus, the evaluation arrangement 200 may react to the pressure and/or the temperature in the surrounding area of the thermal gas sensor 100 and may accordingly very precisely determine the information 240 about the gas concentration and/or the thermal diffusivity.

According to an embodiment of the present invention, when determining the information 240 about the gas concentration and/or the thermal diffusivity, the evaluation arrangement 200 may be implemented to use as input quantities of a drift correction the combination signal 230, information about the temperature in a surrounding area of the thermal gas sensor 100, and information about a pressure in a surrounding area of the thermal gas sensor 100, in order to obtain the information about the gas concentration and/or the thermal diffusivity as a result of the drift correction. Thus, for example, the drift correction may be applied to the combination signal dependent on the information about the temperature and the pressure in order to obtain the information 240 about the gas concentration and/or thermal diffusivity. For example, apart from the three stated input variables (the combination signal, the information about the temperature, and the information about the pressure), the drift correction may obtain no further variables, but may only use previously obtained constants, such as those determined in the context of a calibration. In this case, the constants may be specific for the thermal gas sensor 100 that is used. Thus, the evaluation arrangement 200 may be implemented to consider small differences between thermal gas sensors 100 when calculating the information 240 about the gas concentration and/or thermal diffusivity in order to obtain a very precise result (information 240). For example, the drift correction may correct a temperature drift and/or a pressure drift.

Figure 1C:
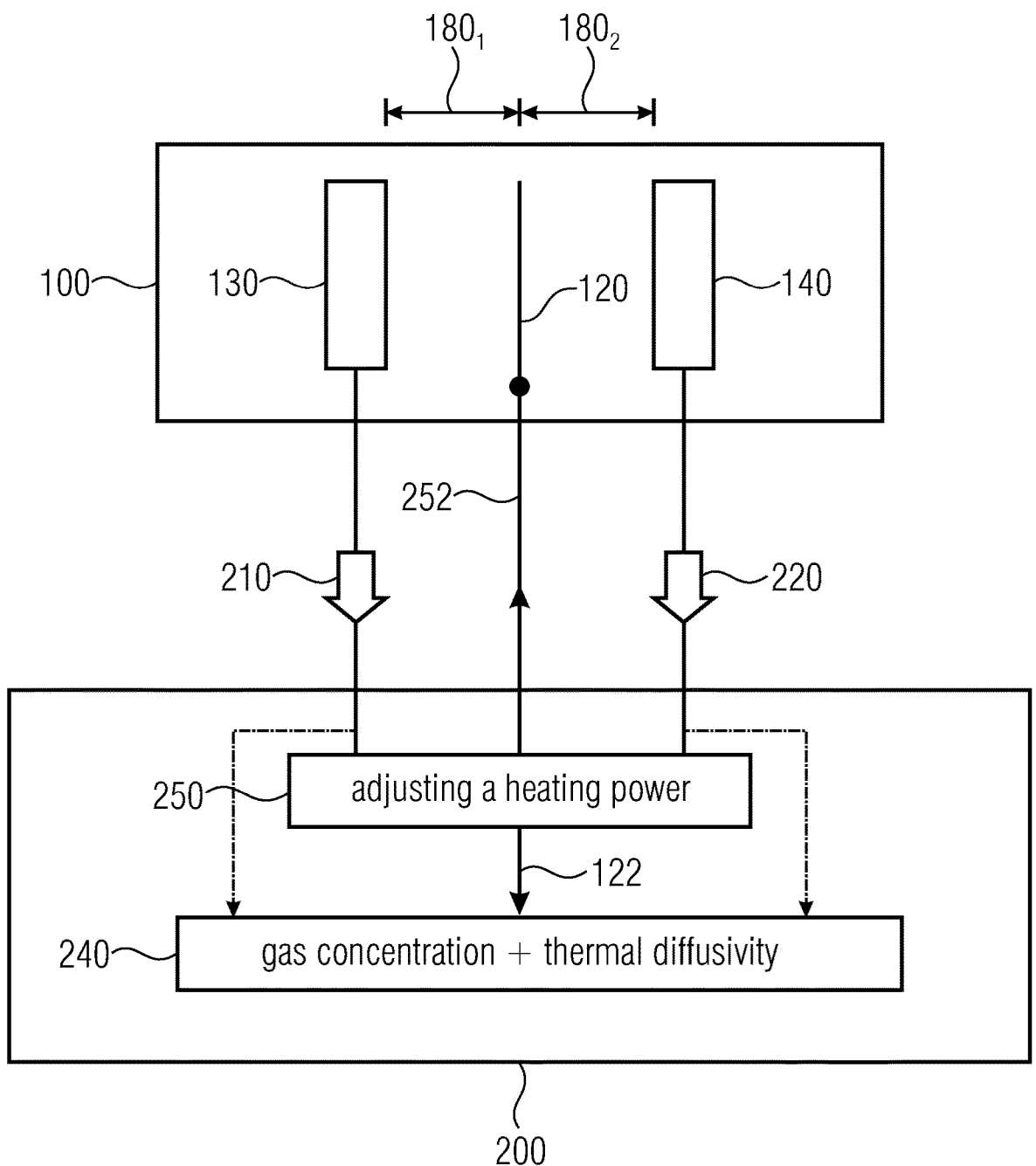
FIG. 1c shows a schematic illustration of an evaluation arrangement for a thermal gas sensor with a control of a heating power, according to an embodiment of the present invention.

FIG. 1c shows a schematic illustration of an evaluation arrangement 200 for a thermal gas sensor 100 with at least one heater 120 and two detectors (a first detector 130 and a second detector 140). The first detector 130 may comprise a first distance $180_1$ to the heater 120, and the second detector 140 may comprise a second distance $180_2$ to the heater 120. According to FIG. 1c, the first detector 130 and the second detector 140 comprise the same distance $180_1$, $180_2$ to the heater 120. However, it is also possible that the first distance 180₁ differs from the second distance 180₂. Thus, for example, the first detector 130 may be arranged in a different distance to the heater 120 than the second detector 140. The evaluation arrangement 200 may be configured to control (e.g. using a control unit 250 for controlling a heating power) a heating power, which may be applied to the heater 120, dependent on least one sensor signal (e.g. a first sensor signal 210 and/or a second sensor signal 220) from at least one of the detectors (e.g. the first detector 130 and/or the second detector 140) in order to bring the at least one sensor signal 210, 220 into a predetermined value range.

For example, in order to analyze and/or further progress the at least one sensor signal 210, 220 by the evaluation arrangement, it is advantageous if the at least one sensor signal 210, 220 is brought into the predetermined value range by the evaluation arrangement 200. For example, if the heating power is increased, an amplitude or a frequency of the at least one sensor signal 210, 220 may also be increased, for example. For example, this may be performed by the evaluation arrangement 200 if the at least one sensor signal 210, 220 is too small and the predetermined value range is too large. Thus, the new sensor signal 210, 220 may fill out, or be located in, the predetermined value range after the control of the heating power by the control unit 250. For example, the predetermined value range may depend on the components of the evaluation arrangement 200 that are used, e.g. an analog-digital converter (ADC). Thus, for example, the ADC may further process the at least one sensor signal 210, 220 very efficiently if the at least one sensor signal 210, 220 is adapted in the predetermined value range adapted to the ADC (e.g. the ADC operating range).

The evaluation arrangement 200 may also be implemented to control the heating power of the heater 120 with the control unit 250 such that the heating power of the heater 120 is reduced. Through this, the at least one sensor signal 210, 220 may also be reduced. For example, this may be advantageous if the at least one sensor signal 210, 220 exceeds the predetermined value range, i.e. is too large. Due to the fact that the evaluation arrangement 200 is implemented to control the heating power of the heater 120 with the control unit 250, it is possible that, when further processing the at least one sensor signal 210, 220 by exemplary components of the evaluation arrangement 200, such as the ADC, no or only little information of the at least one sensor signal 210, 220 is lost.

According to an embodiment, the control unit 250 of the evaluation arrangement 200 may transmit a control signal 252 to the heater 120 for controlling the heating power of the heater 120. Additionally, the control unit 250 may provide information 122 to the evaluation arrangement 200 about the controlled heating power of the heater 120.

The evaluation arrangement 200 may be configured to consider information 122 about the heating power when deriving information 240 about a gas concentration and/or thermal diffusivity from the at least one sensor signal 210, 220. Thus, it is possible that the control unit 250 brings the sensor signal 210, 220 into the predetermined value range and additionally considers the information 122 about the heating power in the analysis since the at least one sensor signal 210, 220 depends on the heating power. In addition, this evaluation arrangement 200 makes it possible that one sensor signal, e.g. the first sensor signal 210 or the second sensor signal 220, may be sufficient to derive the information 240 about the gas concentration and/or the thermal diffusivity of a gas or a fluid (e.g. of a gas or a gas mixture) with a certain accuracy. If the first sensor signal 210 and the second sensor signal 220 as well as the heating power 122 are used to derive the information 240, the determination of the information 240 is overdetermined, as a result of which the information 240 may be determined very precisely by the evaluation arrangement 200. For example, if the first distance 180₁ of the first detector 130 to the heater 120 differs from the second distance 180₂ of the second detector 140, the information 240 about the gas concentration and/or the thermal diffusivity of a gas may just be derived from the first sensor signal 210 and the second sensor signal 220, without using the information 122 about the heating power of the heater 120.

According to an embodiment, the evaluation arrangement 200 may also obtain the information 122 about the heating power from the thermal gas sensor 100 instead of from the control unit 250.

According to an embodiment, the evaluation arrangement 200 may be implemented to apply a periodic signal (e.g. the control signal 252) to the heater 120. For example, the periodic signal may be a periodic square-wave signal or a sinusoidal signal. If the control signal 252, and therefore the heat dissipated to the gas to be analyzed by the heater 120, is a periodic signal, the first sensor signal 210 detected by the first detector 130 and the second sensor signal 220 detected by the second detector 140 may also be periodic. However, due to the first distance 180₁ and the second distance 180₂, the first sensor signal 210 and/or the second sensor signal 220 may differ in phase with respect to the periodic signal of the heater 120, and may differ in amplitude with respect to the periodic signal of the heater 120. For example, the evaluation arrangement 200 may use these differences to very precisely determine the information 240 about the gas concentration and/or the thermal diffusivity.

According to an embodiment, the evaluation arrangement 200 may be configured to switch the heating power applied to the heater 120 (e.g. by means of the control signal 252) between two values. Thus, for example, a periodic square-wave signal may be applied to the heater 120. Thus, for example, the heater 120 may alternately transfer a first heating power and a second heating power to the gas to be analyzed.

According to an embodiment, the evaluation arrangement 200 may be implemented to control (e.g. with the control unit 250) an amplitude of the heating power such that a minimum value of the at least one sensor signal 210, 220 and a maximum value of the at least one sensor signal 210, 220 are in the predetermined value range. For example, if the amplitude of the heating power of the heater 120 is increased by the control signal 252, the minimum value of the at least one sensor signal 210, 220 may be decreased and the maximum value of the at least one sensor signal 210, 220 may be increased, for example. For example, if the amplitude of the heating power is decreased by the control signal 252, the minimum value of the at least one sensor signal 210, 220 may be increased and the maximum value of the at least one sensor signal 210, 220 may be decreased.

According to an embodiment, the predetermined value range may depend on a value range of a component, such as an ADC, of the evaluation arrangement 200. Thus, for example, the predetermined value range may be determined dependent on a component value range (e.g. of a component of the evaluation arrangement 200). Thus, for example, the predetermined value range may specify that the minimum value of the at least one sensor signal 210, 220 is to be in the range of 0% to 30%, 1% to 25%, or 2% to 20% of the component value range, for example, and that the maximum value of the at least one sensor signal 210, 220 is to be in a range of 70% to 100%, 75% to 99%, or 80% to 98% of the component value range. Thus, for example, the predetermined value range may comprise a lower value range in which the minimum value is to be located, and an upper value range in which the maximum value is to be located.

According to an embodiment, the evaluation arrangement 200 may be implemented to set or adjust (e.g. with the control unit 250) an amplitude of the heating power such that an amplitude of the at least one sensor signal 210, 220 is in a specified amplitude range. For example, if the at least one sensor signal 210, 220 comprises a periodic sinusoidal signal, the amplitude should be in the specified amplitude range at each point in time of the sensor signal. Here, the amplitude of the at least one sensor signal should utilize the full specified amplitude range. For example, the specified amplitude range may comprise/be divided into an upper, center, and lower amplitude range. For the specified amplitude range to be utilize by the amplitude of the at least one sensor signal, a maximum amplitude of the at least one sensor signal should be in the upper range, and a minimum amplitude should be in the lower range, for example. For example, the specified amplitude range may depend on the component range. Thus, for example, the specified amplitude range may be determined such that the amplitude of the at least one sensor signal utilizes at least 50%, or at least 65%, or at least 75% of a component value range of an analog-digital converter, for example.

According to an embodiment, the evaluation arrangement 200 may be configured to set or adjust sampling times at which a sensor signal 210, 220 may be sampled. For example, the sensor signal 210, 220 may be optionally preprocessed by the evaluation arrangement 200 or the thermal gas sensor 100, and/or may be applied with a DC offset. According to an embodiment, it may be advantageous if the sensor signal 210, 220 is sampled at a point in time of a maximum amplitude and at a point in time of a minimum amplitude. For example, these two sampling times may be set or readjusted by the evaluation arrangement 200 if the evaluation arrangement 200 determines that the sampling times have been incorrectly selected. By exactly setting the sampling times, it may be possible, e.g., that the evaluation arrangement may very easily determine a phase difference or an amplitude difference between the first sensor signal 210 and a heater signal (e.g. emitted by the heater 120 and controlled by the control signal 252) or between the second sensor 220 and the heater signal. By means of the very precise phase difference and/or amplitude differences, the evaluation arrangement 200 may very precisely determine, or derive, the information 240 about the gas concentration and/or thermal diffusivity of the gas to be analyzed.

According to an embodiment, the evaluation arrangement 200 may be implemented to set the sampling times such that a sampling, e.g., is carried out with a phase difference of up to +/−2° at a point in time at which the sensor signal 210, 220 reaches a maximum value, and such that the sampling, e.g., is carried out with a phase difference of up to +/−2° at a point in time at which the sensor signal 210, 220 reaches a minimum value. For example, the maximum value may define a maximum amplitude of the sensor signal 210, 220, and the minimum value may define a minimum amplitude of the sensor signal 210, 220, as described above.

According to an embodiment, the evaluation means 200 may be implemented to combine a sensor signal 210, 220 from at least one of the detectors 130, 140 with an offset signal generated by a digital-analog converter in order to obtain an input signal for the analog-digital converter. The evaluation means 200 may be implemented to adjust the offset signal in order to achieve that the input signal of the analog-digital converter remains within a specified range during a total period of the sensor signal 210, 220. Thus, for example, the offset signal may be implemented to adapt the sensor signal 210, 220 such that the input signal that is in a component value range of the analog-digital converter is created. Thus, for example, the offset signal may be adjusted/adapted in order to be able to react to different sensor signals 210, 220 from different gases to be analyzed. Thus, for example, the offset signal may be configured to decrease a sensor signal 210, 220 that is too large so that the resulting input signal is in the specified range. In addition, when the sensor signal 210, 220 is too small, the offset signal may be configured to increase the sensor signal 210, 220 so that an input signal that is in the specified range is created.

Thus, on the one hand, the evaluation arrangement 200 may be implemented to bring the amplitude of the sensor signal 210, 220 into the predetermined value range by controlling the heating power, and to change an offset of the sensor signal 210, 220 by combining the sensor signal 210, 220 with the offset signal such that the sensor signal 210, 220 is in a predetermined value range. This makes it possible that the sensor signal 210, 220 may be analyzed very precisely, and that very precise information 240 about the gas concentration and/or the thermal diffusivity of the gas to be analyzed may therefore be determined by the evaluation arrangement 200.

According to an embodiment, the evaluation means 200 may be implemented to control the heating power only when a setting or adjustment of the sampling times is in a steady state and when an adjustment of the offset signal is in a steady state. A steady state may be understood such that the sampling times have been determined by the evaluation means 200 such that the sensor signal 210, 220 may be sampled at predefined events (such as a maximum amplitude (maximum value), a zero crossing, or a minimum amplitude (minimum value)). Similarly, the steady state may signify that the offset signal has been adjusted such that the sensor signal 210, 220 generates, upon combining the offset signal with the sensor signal 210, 220, an input signal that is in the specified range, and to therefore very precisely analyze the sensor signal 210, 220 by means of the evaluation arrangement, without or with only little information losses. Thus, for example, pre-settings (such as the sampling times in the steady state, or the offset signal in the steady state) may be determined by the evaluation means 200 so that, when controlling the heating power by means of the control unit 250, the new sensor signal 210, 220 may be very precisely analyzed with the pre-settings and, under certain circumstances, a new control of the sampling times, or the offset signal, is not needed anymore to derive the information 240 about the gas concentration and/or the thermal diffusivity from the sensor signal 210, 220.

According to an embodiment, the evaluation arrangement 200 may be implemented to stop the control of the heating power (e.g. by means of the control unit 250), while the sampling times are set or adjusted and/or while the offset signal is adjusted. Thus, for example, it may be ensured that there are no changes made to the sensor signal 210, 220 while the sampling times and the offset signal are not yet in a steady state. Thus, this may be ensure that the sensor signal 210, 220 may be analyzed very precisely since the sampling times and the offset signal may be determined very precisely with only a very small susceptibility to errors or none at all.

According to an embodiment, the evaluation arrangement 200 may be implemented to control a mean heating power or a maximum heating power and also an amplitude of the heating power. Thus, for example, the control unit 250 may transmit as a control signal 252 a new heater signal for the heater 120 to the thermal gas sensor 100, wherein the control signal comprises a changed mean heating power, maximum heating power, or amplitude of the heating power, for example. However, it is also possible that the control signal 152 includes information stating how the mean heating power, the maximum heating power, or the amplitude of the heating power is to be changed by the thermal gas sensor for the heater 120.

Figure 1D:
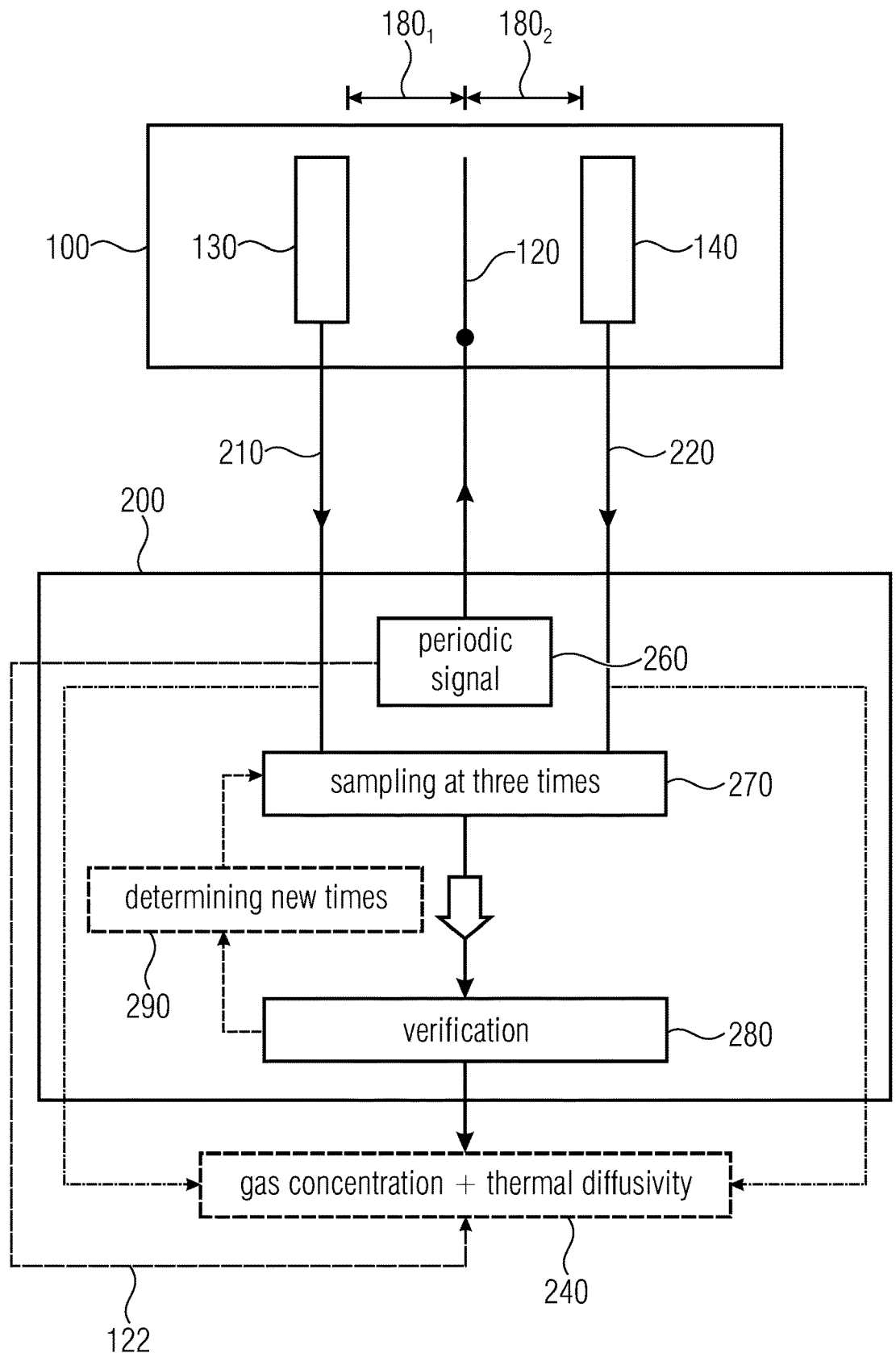
FIG. 1d shows a schematic illustration of an evaluation arrangement for a thermal gas sensor with sampling a sensor signal at three points in time, according to an embodiment of the present invention.

FIG. 1*d* shows a schematic illustration of an evaluation arrangement 200 for a thermal gas sensor 100 with at least one heater 120 and two detectors (e.g. a first detector 130 and a second detector 140) arranged in different distances (e.g. a first distance $180_1$ and a second distance $180_2$) to the heater 120. For example, the first detector 130 may comprise the first distance $180_1$ to the heater 120, and the second detector 140 may comprise the second distance $180_2$ to the heater 120. The evaluation arrangement 200 may be implemented to apply a periodic signal 260 with a specified period duration to the heater 120. In this case, for example, the periodic signal may a square-wave signal, an impulse signal with a known power, or a sinusoidal signal. Optionally, it may also be a sinusoidal signal with harmonics, or a triangular signal. The periodic signal may also be referred to as a heater signal, and may be transferred in the form of heat from the heater 120 to the first detector 130 and/or the second detector 140 via a gas to be analyzed. The transferred heat may be detected by the first detector 130 as a first sensor signal 210, and by the second detector 140 as a second sensor signal 220. The first sensor signal 210 and the second sensor signal 220 may comprise a first periodic signal and a second periodic signal, respectively, each comprising the specified period duration. This makes it possible that the gas to be analyzed may be analyzed very precisely with respect to its gas concentration and/or thermal diffusivity by the thermal gas sensor 100, or the evaluation arrangement 200. The evaluation arrangement 200 may be implemented to sample at least one sensor signal (e.g. the first sensor signal 210 and/or the second sensor signal 220) from one of the detectors 130, 140 at three points in time (e.g. by means of a sampling means 270). For example, a second sampling time may be time-shifted by 90° with respect to the period duration (e.g. with +/−2°) compared to a first sampling time. Thus, for example, the second sampling time may be time-shifted by ¼ period durations, 5/4 period durations, or by 9/4 period durations compared to the first sampling time. A third sampling time may be time-shifted with respect by 180° to the period duration compared to the first sampling time, or by 90° compared to the second sampling time. The first sampling time, the second sampling time, and the third sampling time may comprise a tolerance of +/−2%. That is, for example, the third sampling time may be time-shifted by ½ period durations, 3/2 period durations, or by 5/2 period durations compared to the first sampling time. Thus, the sensor signal 210, 220 may be sampled at precisely defined locations, enabling to very precisely determine information 240 about a gas concentration and/or thermal diffusivity from the sensor signal 210, 220. The evaluation arrangement 200 may be implemented to detect, based on three sampling values that are based on sampling the sensor signal at the first sampling time, the second sampling time, and third sampling time (e.g. performed by means of the sampling apparatus 270), whether a first sampling value and a third sampling value constitute a maximum value and a minimum value of the sensor signal 210, 220. For example, this may be carried out by the examination apparatus 280. For example, the examination apparatus 280 may ignore a DC offset and may therefore examine, apart from a DC offset, whether the first sampling value constitutes a maximum value, and the third sampling value constitutes a minimum value of the sensor signal 210, 220, for example. Thus, for example, the second sampling time may be a "zero crossing" of the sensor signal 210, 220 and may also be considered by the examination means 280.

The first sampling time, the second sampling time, and/or the third sampling time, as well as the first sensor signal 210 and the second sensor signal 220 may be used to determine the information 240 about the gas concentration and/or the thermal diffusivity of a gas detected by the thermal gas sensor 100. Optionally, the heater signal 122 may be additionally used in the determination of the information 240. Thus, for example, a phase difference between the first sensor signal 210 and the second sensor signal 220 as well as an amplitude difference between the first sensor signal 210 and the second sensor signal 220 may be determined based on the sampling time/sample values. Optionally, a phase difference and/or an amplitude difference between the first sensor signal 210 and the heater signal 122 and/or between the second sensor signal 220 and the heater signal 122 may be determined. The information 240 about the gas concentration and/or thermal diffusivity may be determined from the phase differences and amplitude differences determined in such a way.

According to an embodiment, the evaluation arrangement 200 may be implemented to change the sampling times dependent on identifying whether the first sample value and the third sample value constitute a maximum value and/or a minimum value of the sensor signal 210, 220. For example, this may be done by a sampling control means 290. Thus, for example, new sampling times may be determined if the first sample value and the third sample value do not correspond to a maximum value and/or a minimum value of the sensor signal 210, 220. Controlling the sampling times can ensure that the sample values correspond to predetermined values. For example, if the examination means 280 determines that there are deviations outside of a tolerance (e.g. +/−2°), the sampling times may be changed/readjusted by the sampling control means 290.

According to an embodiment, the evaluation arrangement 200 may be implemented to set or adjust the sampling times such that the first sample value constitutes a first extreme value of the sensor signal 210, 220, e.g. a maximum value or minimum value, and such that the third sample value constitutes a second extreme value, e.g. the minimum value or the maximum value of the sensor signal 210, 220. For example, the second sample value may constitute a mean value or DC component of the sensor signal 210, 220, e.g. a "zero crossing".

According to an embodiment, the evaluation arrangement 200 may be configured to, when setting or adjusting the sampling times, consider information about a point in time when the sensor signal 210, 220 passes through a specified threshold value. For example, this point in time may be the second point in time, e.g., that may constitute a DC component or mean value of the sensor signal 210, 220. Thus, for example, the examination means 280 may use the second sampling time for examining the first sampling time and/or the second sampling time. Thus, if the examination means 280 determines, based on the second sampling time, that the first sample value does not correspond to a maximum value or minimum value of the sensor signal 210, 220 and that the third sample value does not correspond to the minimum value or the maximum value of the sensor signal 210, 220, the sampling control apparatus 290 may set the sampling times anew or readjust them. For example, the specified threshold value may define a "zero crossing" (e.g. apart from a DC offset).

According to an embodiment, the evaluation arrangement 200 may be implemented to examine whether a second sample value at the second sampling time is identical to a mean value of the sample value at the first sampling time and the third sample value at the third sampling time, and to detect, dependent on the examination, whether the first sample value and the third sample value represent a maximum value and a minimum value of the sensor signal. For example, the second sample value should be identical, with a tolerance of at most ±1%, to a difference between the first sample value and the third sample value or identical to an mean value of the sample value and the second sample value. If this is not the case, the examination apparatus 280 may detect that the sampling times have been selected incorrectly. Since the first sample value constitutes a first extreme value, and the third sample value, time-shifted by 180° with respect to the period duration, constitutes a second extreme value of the sensor signal 210, 220, the second sample value may be located at exactly half the time between the first sampling time and the second sampling time. Thus, the second sampling value may correspond to the mean value of the other two sampling values. Thus, this may constitute an efficient and exact method to examine the sample values with the help of the examination apparatus 280.

According to an embodiment, the evaluation arrangement 200 may be implemented to apply a periodic square-wave signal 260 to the heater 120 with a duty factor of 50%. However, it is also possible that the periodic square-wave signal comprises a duty ratio in the range of 5% to 50%, 8% to 48%, or 10% to 45%. The periodic square-wave signal 260 applied to the heater 120 may comprise a tolerance of +/−2%. According to an embodiment, the duty ratio indicates for a periodic sequence of impulses a ratio of an impulse duration to a period duration.

According to an embodiment, the evaluation arrangement 200 may be implemented to combine a sensor signal 210, 220 with an offset signal generated by a digital-analog converter in order to obtain an input signal for an analog-digital converter. For example, the analog-digital converter may digitize the signal values (e.g. the first sample value, the second sample value, and/or the third sample value) present at the sampling times and uses this to sample the sensor signal 210, 220. For example, the sampling apparatus 270 may comprise the analog-digital converter.

According to an embodiment, the evaluation arrangement 200 may be configured to adjust the offset signals in order to achieve that the input signal of the analog-digital converter remains within a specified range during an entire period of the sensor signal 210, 220. Thus, for example, the offset signal may change an offset of the sensor signal 210, 220 such that an input signal that is in an operating range (e.g. the specified range) of the analog-digital converter is created, so that no information of the sensor signal 210, 220 is lost in the digitization, or so that an information loss is reduced. Thus, for example, the sampling apparatus 270 may examine whether an input value of the analog-digital converter exceeds a specified upper threshold value, e.g. of the specified range, or falls below a specified lower threshold value, e.g. of the specified range. Accordingly, the sampling apparatus 270 may generate the offset signal that may be combined with the sensor signal 210, 220 so that the input value, e.g. a value of the input signal, remains in the specified range. The evaluation arrangement 200 may be implemented to adjust the sampling times after adjusting the offset signal and to again perform, after a change of the sampling times, an examination as to whether sample values obtained with the changed setting of the sampling times are still within the specified range. Thus, for example, the offset signal may be initially generated for the sensor signal 210, 220 by the evaluation arrangement 200, and sampling times may subsequently be determined, examined, and possibly readjusted by the sampling apparatus 270 (e.g. this may constitute a tracking of the sampling times). After this tracking, new sample values that may involve a repeated adjustment of the offset signal by the evaluation arrangement 200 may be created. Thus, for example, the offset signal and the sampling times may be alternately adjusted, or tracked, until the analog-digital converter may process the sensor signal 210, 220, for example. Thus, at this point in time, the offset signal and the sampling times may be in a steady state.

For example, the settings of the sampling times changed by the sampling control means 290 generate new sample values that may be considered as input values of the analog-digital converter. For the input signal of the analog-digital converter to remain in the specified range, the offset signal and the heating power of the heater 120 may be readjusted. For example, the offset signal may adapt an offset of the sensor signal 210, 220, and the change of the heating power may adapt an amplitude of the sensor signal 210, 220, so that an input signal that is in the specified range is created.

According to an embodiment, the evaluation arrangement 200 may be implemented to control a heating power applied to the heater 120, dependent on at least one sensor signal 210, 220 from at least one of the detectors 130, 140 in order to bring the at least one sensor signal 210, 220 into a predetermined value range. The evaluation arrangement 200 may be implemented to consider information about the heating power (e.g. the heater signal 122) when deriving information 240 about a gas concentration and/or thermal diffusivity from the sensor signal 210, 220. Thus, for example, upon an increase of the heating power of the heater 120, the sensor signal 210, 220 may experience an increase of an amplitude of the sensor signal 210, 220, or, upon a reduction of the heating power, the at least one sensor signal 210, 220 may experience a decrease of an amplitude of the sensor signal 210, 220. Thus, for example, the sensor signal 210, 220 may be brought into the predetermined value range by controlling the heating power of the heater 120.

In the following, embodiments of the thermal gas sensor and the evaluation arrangement are described based on further drawings.

1.1 Technological Variations for a Thermal Gas Sensor

Figure 2A:
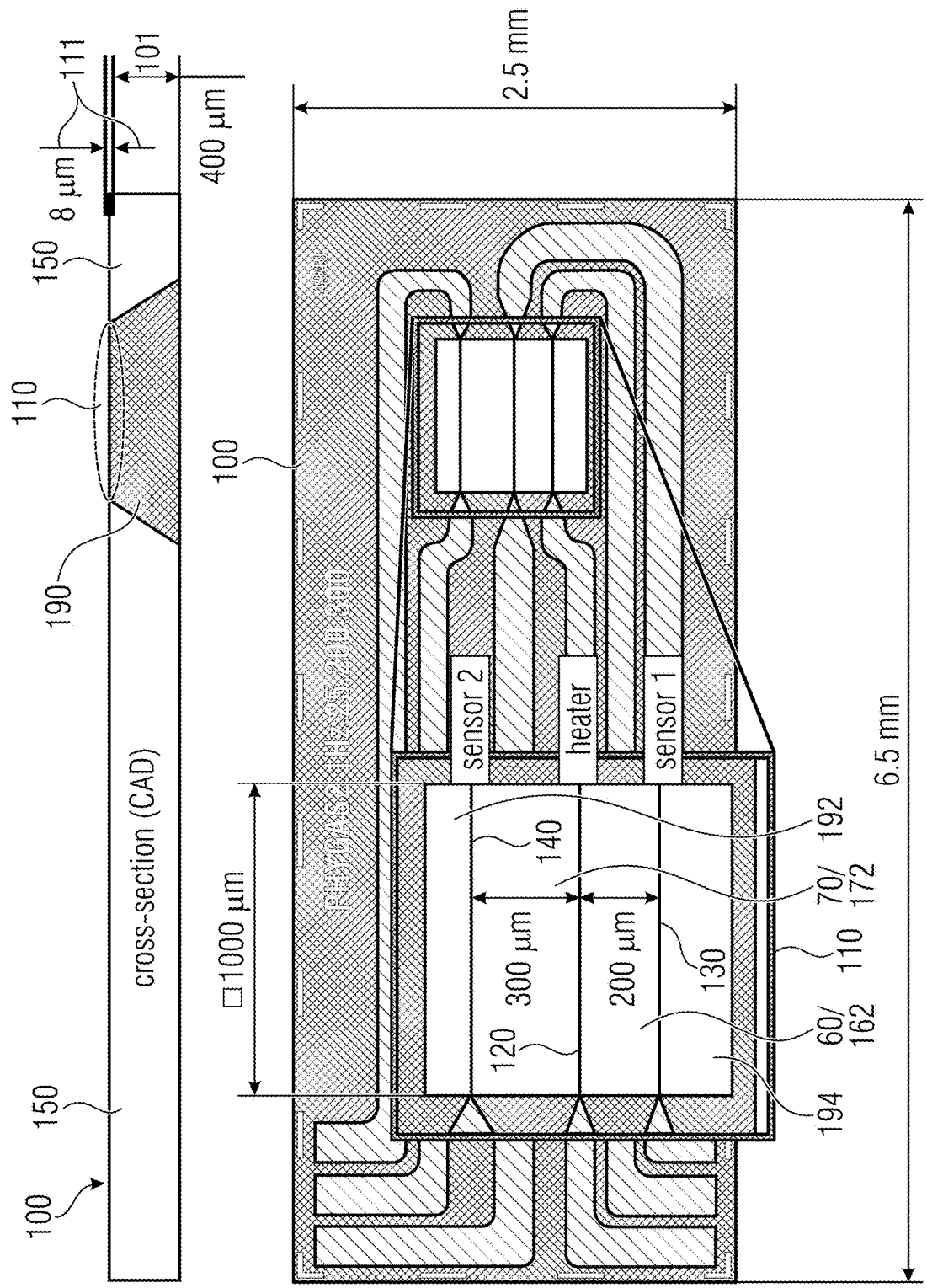
FIG. 2a shows a schematic illustration of a gas sensor in the light microscope, according to an embodiment of the present invention.
Figure 2B:
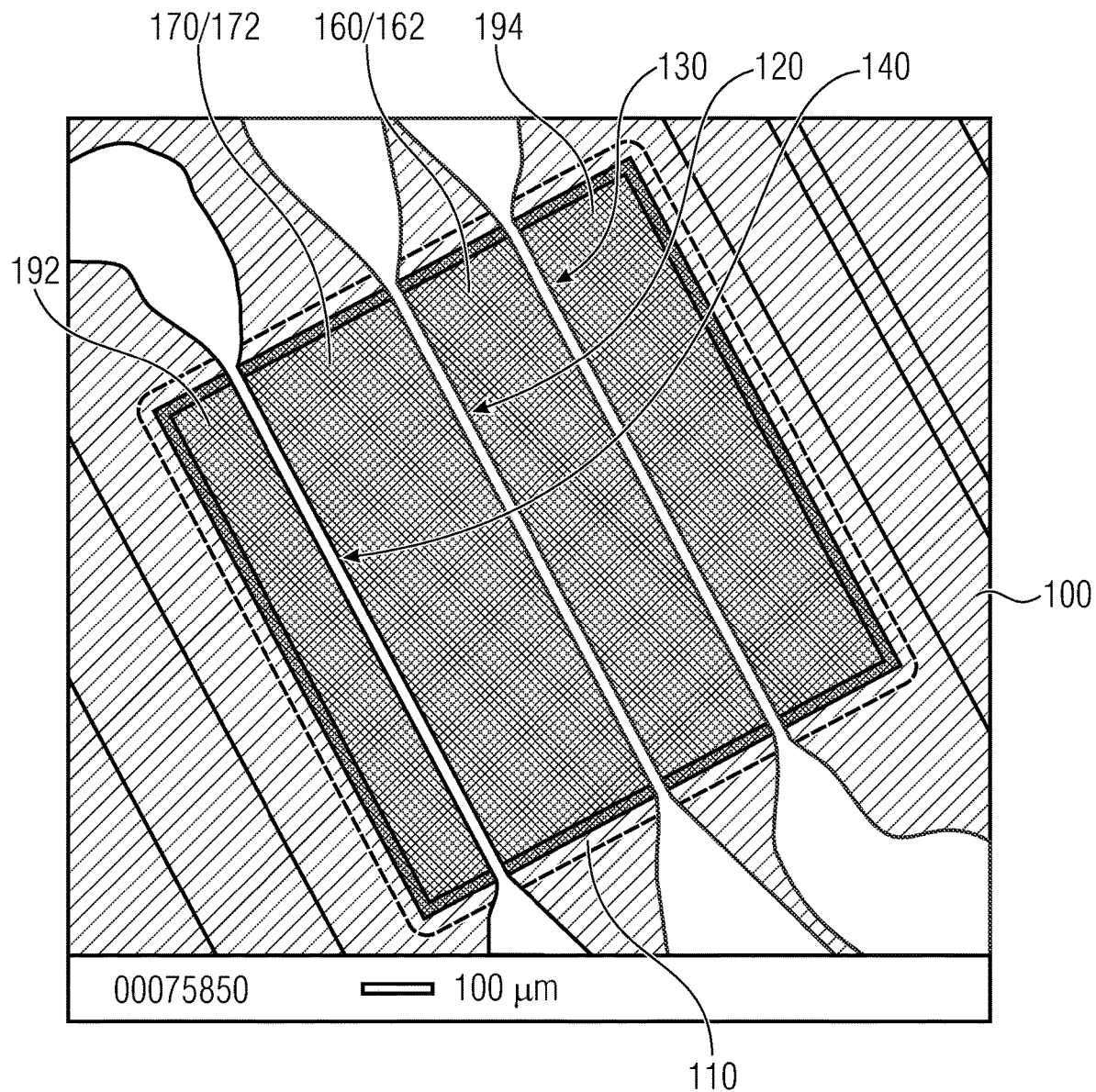
FIG. 2b shows a schematic illustration of a gas sensor in the scanning electron microscope, according to an embodiment of the present invention.

FIG. 2*a* and FIG. 2*b* each show a schematic illustration of a gas sensor 100 for measuring physical gas properties. The thermal gas sensor 100 may comprise a thin-layer membrane 110 and a heating element 120, e.g., that may be arranged as a self-supporting bridge structure on the membrane 110 between a first discontinuation area 160 of the membrane 110 and a second discontinuation area 170 of the membrane 110. In the case of a wire sensor (an example for the temperature sensor structures 130, 140; cf. FIG. 2 and FIG. 3), a thickness of the thin-layer membrane 110 (consisting of several base layers, sensor layers, and passivation layers, for example) may be between 1-10 μm, for example. The heating element 120 may also be referred to as a heater. According to FIG. 2*a* and FIG. 2*b*, the entire first discontinuation area 160 may comprise a discontinuation 162 of the membrane 110, and the entire second discontinuation area 170 may comprise a discontinuation 172 of the membrane. Thus, the heating element 120 may be arranged in a self-supporting manner between the first discontinuation 162 and the second discontinuation 172. The first discontinuation 162 may be limited by the heating element 120 and a first temperature sensor structure 130 in the form of a self-supporting bridge structure. The second discontinuation 172 may be limited by the heating element 120 and a second temperature sensor structure 140, e.g., in the form of a self-supporting bridge structure. The first temperature sensor structure 130 and/or the second temperature sensor structure may be a wire sensor, thermopiles, temperature-variable resistors or thermistors.

Optionally, the gas sensor 100 may comprise a first outer discontinuation 192 and a second outer discontinuation 194. Thus, for example, the first thermal element structure 130 may be a self-supporting bridge structure between the first discontinuation 160 and the second outer discontinuation 194, and the second thermal element structure 140 may be a self-supporting bridge structure between the second discontinuation 172 and the first outer discontinuation 192. The first thermal element structure 130 may also be referred to as a first detector or a first sensor, the second thermal element structure 140 may also be referred to as a second sensor or a second detector.

A cross-section of the gas sensor 100 can be seen in the upper area of FIG. 2a. For example, the gas sensor 100 includes a frame 150 made of a carrier material. For example, the frame 150 made of a carrier material may spread the membrane 110. According to an embodiment, the membrane 110 may comprise a thickness 111 (e.g. an expansion perpendicular to a surface of the membrane 110 on which the first thermal element structure 130, the second thermal element structure 140, and the heating element 120 are arranged) in a range of 1 µm to 50 µm, 2 µm to 25 µm, or 3 µm to 10 µm, e.g. 8 µm. According to an embodiment, the membrane 110 may be realized by recess 190 from the frame 150. Thus, for example, the recess 190 may be selected such that a membrane 110 may be realized with the desired thickness 111.

According to the embodiment in FIG. 2a and FIG. 2b, the recess 190 may be implemented such that only the heating element 120, the first thermal element structure 130, and the second thermal element structure 140 remain spread out between the frame 150, for example. According to an embodiment, a surface of the membrane 110 on which the first thermal element structure 130, the second thermal element structure 140, and the heating element 120 are arranged may comprise an expansion in a range from 200×200 µm² to 5×5 mm², 500×500 µm² to 2000×2000 µm² or 800×800 µm² to 1200×1200 µm², wherein the expansion may be a square or rectangular expansion. The gas sensor 100 may comprise a thickness 101 (e.g. in parallel to the thickness 111 of the membrane 110) in a range from 500 nm to 5 mm, 1 µm to 1 mm, or from 200 µm to 600 µm, e.g. 400 µm. An expansion of the gas sensor 100 in parallel to the surface of the membrane 110 on which the heating element 120 is arranged may be in a range from 1×1 mm² to 1×1 cm², 1.5×1.5 mm² to 9×9 mm², or from 2×2 mm² to 8×8 mm², e.g. 6.5×2.5 mm².

According to an embodiment, the first thermal element structure 130, the second thermal element structure 140, and/or the heating element 120 may be part of the membrane 110.

In order to measure a heat transport that depends on the gas type and/or the gas mixture, a microchip (an example for the thermal gas sensor 100) with three fine bridge structures (e.g. the heating element 120, the first thermal element structure 130, and the second thermal element structure 140) that are spread out in a self-supporting manner between a frame and may be surrounded as micro wires by gas to be analyzed may be used. For example, the gas to be analyzed may be arranged in the first discontinuation 162, the second discontinuation 172, the first outer discontinuation 192, and/or the second outer discontinuation 194. A central bridge structure may be implemented as the heater 120, and two detector structures (e.g. the first thermal element structure 130 and the second thermal element structure 140) arranged on both sides in different distances to the heater 120 may be used as temperature sensors for measuring a transfer response from the gas mixture.

For example, a periodic heat signal is applied to the center wire (the heating element 120), as a result of which heat is radiated by the heating element, for example. A heat transfer may take place via unknown heat transitions from the heater 120 into the gas to be analyzed, and from the gas into the sensor wire (e.g. into the first thermal element structure 130 and/or the second thermal element structure 140). The heat transfer detected in such a way by the first thermal element structure 130 and/or the second thermal element structure 140 may be understood as a transfer response or as a sensor signal (e.g. a first sensor signal detected by the first thermal element structure 130 and a second sensor signal detected by the second thermal element structure 140) By measuring a temperature response (e.g. the transfer response) with two identical sensors (e.g. the first thermal element structure 130 and/or the second thermal element structure 140) in different distances to the heater 120, the unknown heat transitions in the measuring arrangement may be eliminated, for example. The phase and amplitude of the two sensor signals may essentially depend on the heat transfer by the gas.

1.1.1 Example: The gas sensor 100 as an MEMS wire sensor (evaluation of a TCR (temperature coefficient of resistance) at detector resistors (e.g. a resistance of the first thermal element structure 130 and/or the second thermal element structure 140)) (alternative embodiment, optionally usable in combination with the signal generation and evaluation according to section 1.2 and the evaluation algorithm according to section 1.3)

A first variation of the thermal gas sensor 100 may be built on the basis of a silicon-on-insulator (SOI) wafer substrate. For example, it consists of a microchip with self-supporting fine bridge structures made of silicon micro wires (e.g. the first temperature sensor structure 130 and the second temperature sensor structure 140) spread out in the gas space to be analyzed. A center wire may be implemented as a heater 120, and two detector wires (e.g. the first temperature sensor structure 130 and the second temperature sensor structure 140) may be used as temperature sensors on both sides of the heater in different distances to the same (cf. FIG. 2a, FIG. 2b).

For example, FIG. 2a shows an image of the MEMS wire sensor chip (the gas sensor 100) in a light microscope and FIG. 2b shows a close-up of structures in a scanning electron microscope.

Figure 3:
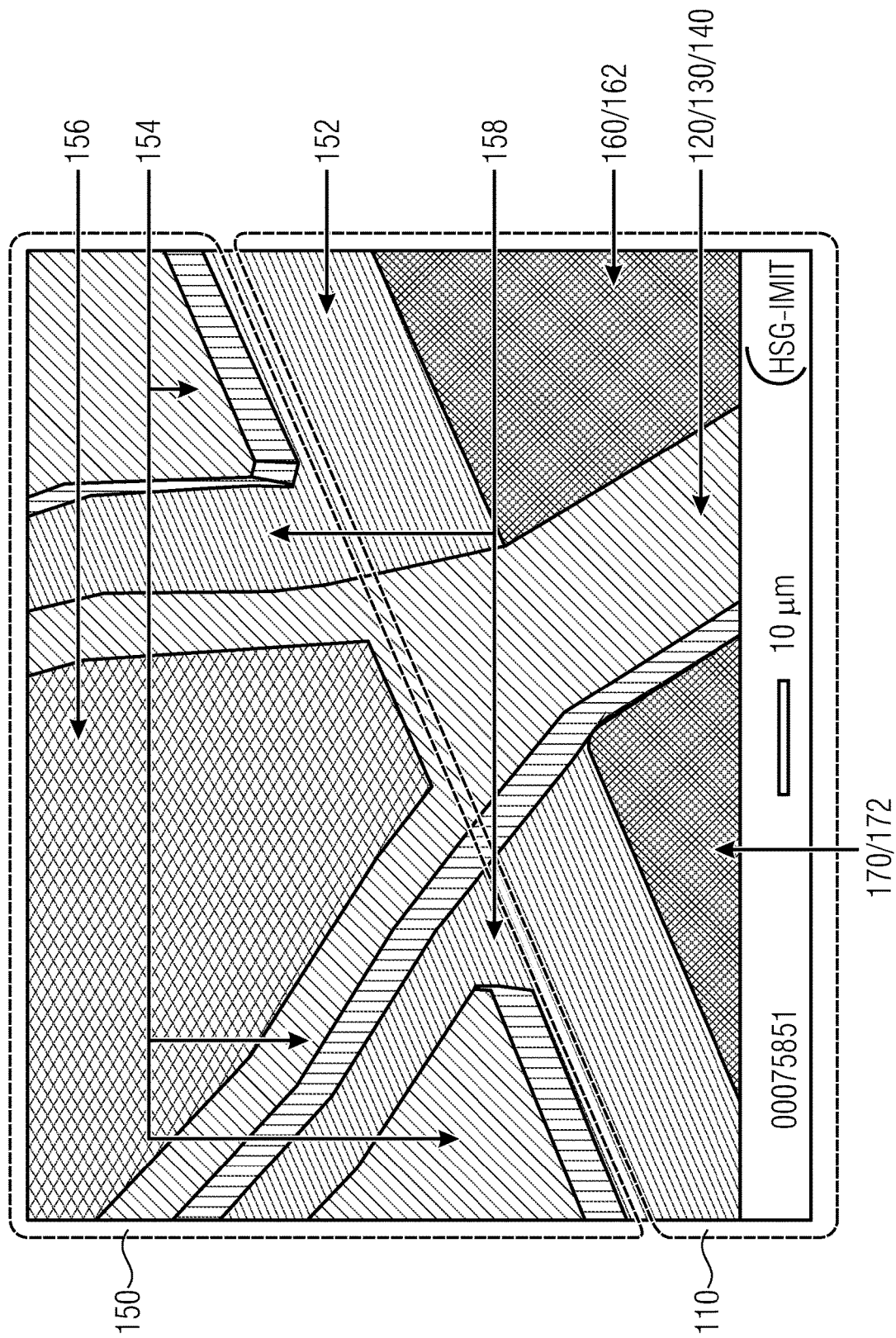
FIG. 3 shows a schematic illustration of a section of a scanning electron microscope image of micro bridge for a gas sensor according to an embodiment of the present invention.

FIG. 3 shows a schematic illustration of a silicon bridge 120/130/140 that may be used for a heating element, a first thermal element structure, and/or a second thermal element structure of a gas sensor, for example. In other words, FIG. 3 shows a detail of a micro bridge (SEM, scanning electron microscope) of a thermal MEMS wire sensor (e.g. a gas sensor). For example, the illustrated silicon bridge 120/130/140 may be manufactured in SOI technology. Thus, for example, a substrate or carrier material of a frame 150 may comprise an oxide material 152, a silicon material 154, and an aluminum material 156. For example, in order to realize the silicon bridge, the silicon material 154 may be partially removed in order to realize cutouts 158 (e.g. trenches) in the carrier material of the frame 150 and to therefore realize the silicon bridge 120/130/140. The silicon bridge 120/130/140 may be arranged on the membrane 110 (e.g. consisting of the oxide material 152).

For example, the membrane 110 may comprise a first discontinuation area 160/162 and a second discontinuation area 170/172. The first discontinuation area 160/162 and the second discontinuation area 170/172 comprise a discontinuation that may be a cavity, for example. Thus, the membrane 110 may comprise a first discontinuation 162 and a second discontinuation 172 in which the gas to be analyzed may be arranged and where heat is transferred to the same from the silicon bridge 120/130/140 if the silicon bridge constitutes a heating element 120, or where the same may transfer heat to the silicon bridge 120/130/140 if the silicon bridge 120/130/140 constitutes the first thermal element structure 130 and/or the second thermal element structure 140. The silicon bridge 120/130/140 may be contacted by the aluminum material 156, as a result of which the aluminum material 156 may be used as a bond pad, for example. For example, by means of the bond pad, an excitatory heater signal may be applied to the heating element 120, or the first thermal element structure 130 and/or the second thermal element structure 140 may be read out (e.g. a first or second sensor signal).

Advantages of the SOI Technology:
Crystalline resistive paths, the temperature coefficient of the resistance (TCR) for the detectors (e.g. for the first thermal element structure 130 and the second thermal element structure 140) may solely depend on the base doping of the wafer material (in the active layer);
TCR of similar magnitude as in platinum at a high base resistance of the resistors of the temperature detectors (e.g. the first thermal element structure 130 and the second thermal element structure 140) enables miniaturized sensor dimensions (e.g. dimensions of the first thermal element structure 130 and the second thermal element structure 140) due to short resistive paths (e.g. from a frame side of the frame 150 to an opposite frame side of the frame 150) of the bridge structures 120, 130, 140 (shorter than 1 mm) and, for the area of resistance temperature detectors (RTD) (e.g. a first thermal element structure 130 and the second thermal element structure 140), comparably small temperature measuring errors due to self-heating since, e.g., base resistance values larger than 8 kOhm may be used, which may need less than 360 µW of power input during the measuring operation.
Heater resistance (e.g. of the heater 120) adaptable to a low operating voltage (3.3 v) by implantation;
Very homogenous distribution of the ohmic sensor resistance, e.g. the resistance of the first thermal element structure 130 and/or the second thermal element structure 140, above the wafer (e.g. the frame 150) in a very narrow process field, in particular, the tolerances of the detector resistances (e.g. sensor resistances) are determined, e.g., by tolerances of the SOI material in an active layer (active layer, base doping, and material thickness) as well as by the lateral structure accuracy of the deep etching (Deep RIE).
Disadvantages of the SOI Technology:
Comparably expensive SOI substrate material when purchasing wafers;
Often not available in desired specifications (wafer diameter, material thickness of handle and active layer, doping of the active layer);
Currently no passivation of the structures, under certain circumstances, passivation leads to bimetal effects due to the different material expansion of the layers upon heat input, variation of the characteristic curve of the TCR;

1.1.2 Example: The gas sensor 100 as a MEMS thermopile sensor on a thin-layer membrane (embodiment according to aspect 1, optionally usable in combination with the signal generation and evaluation according to section 1.2 and the evaluation algorithm according to section 1.3)

Figure 4:
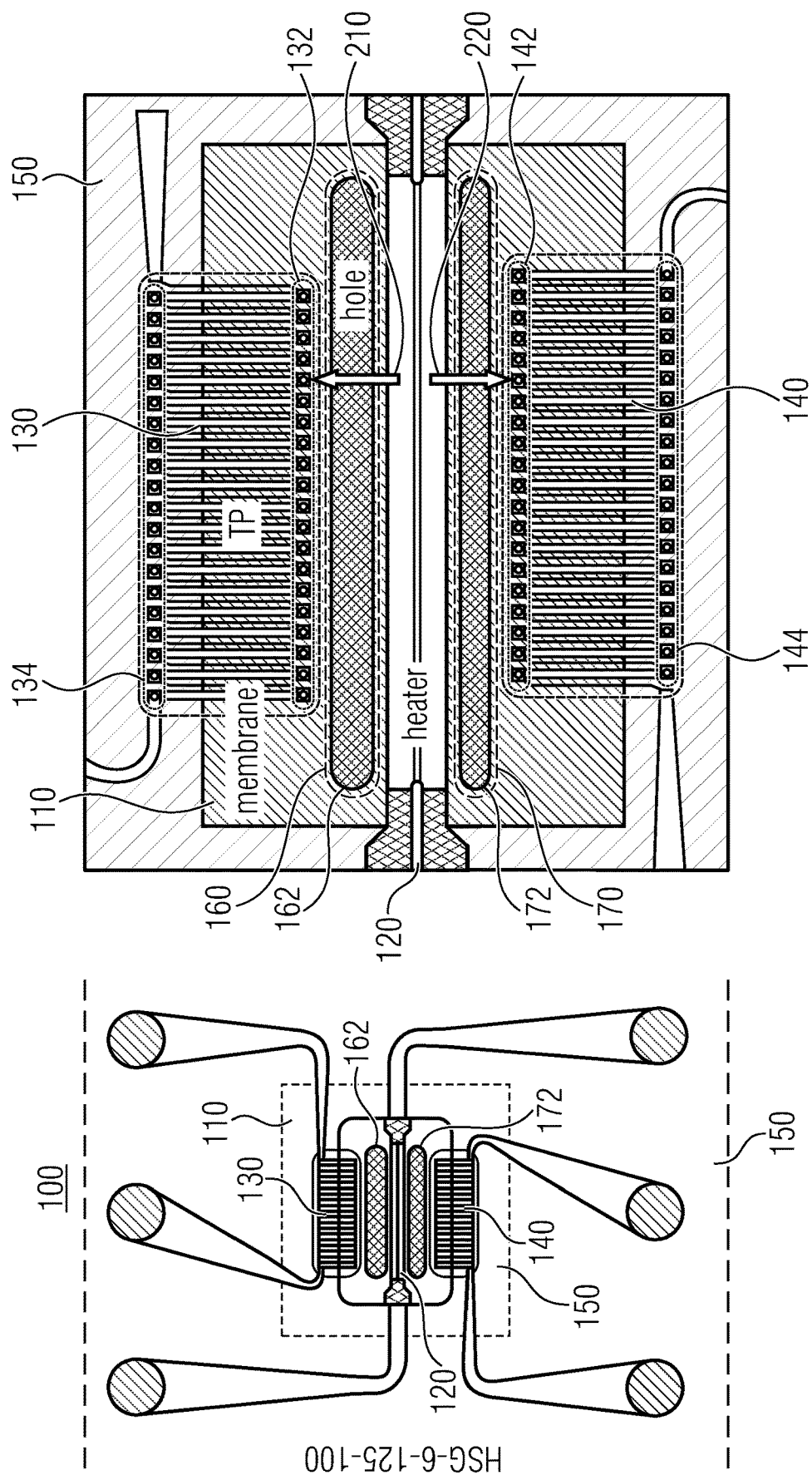
FIG. 4 shows a schematic illustration of a gas sensor with a first discontinuation having an expansion perpendicular to a heater that differs from an expansion perpendicular to a heater of a second discontinuation, according to an embodiment of the present invention.

FIG. 4 shows a schematic illustration of a gas sensor 100 on the left side and a detailed view of the gas sensor 100 on the right side.

According to an embodiment, the gas sensor 100 may comprise a membrane 110 and a heating element 120 that may be arranged on the membrane 110 between a first discontinuation area 160 of the membrane 110 and a second discontinuation area 170 of the membrane 110. The first discontinuation area 160 may comprise a discontinuation 162, and the second discontinuation area 170 may comprise a discontinuation 172.

The first discontinuation 162 and/or the second discontinuation 172 may comprise a longitudinal expansion in parallel to a direction of maximum expansion of the heating element 120 (that may be referred to as a heater, for example), and may comprise a lateral expansion, e.g. in a direction perpendicular to a direction of maximum expansion of the heating element 120. According to FIG. 4, the first discontinuation 162 may therefore have a larger lateral expansion than the second discontinuation 172. In addition, according to FIG. 4, the first discontinuation 162 and the second discontinuation 172 may comprise the same longitudinal expansion. For example, the first discontinuation 162 and the second discontinuation 172 comprise the longitudinal expansion that is large enough that the first discontinuation 162 and the second discontinuation 172 fully cover the area between the first thermal element structure 130 and the second thermal element structure 140, respectively, and the heating element 120. Thus, for example, the longitudinal expansion of the first discontinuation 162 and the second discontinuation 172 extends along the entire length of the heating element 120. This avoids that a majority of the heat radiated by the heating element 120 is transported via the membrane 110. Thus, it may be achieved that a majority of the heat is transferred to the respective thermal element structure 130, 140 via the gas arranged in the first discontinuation 162 and in the second discontinuation 172.

For example, the first thermal element structure 130 may comprise a different distance to the heating element 120 than the second thermal element structure 140. Thus, for example, according to FIG. 4, the first thermal element structure 130 comprises a larger distance to the heating element 120 than the second thermal element structure 140. For example, the first thermal element structure 130 may detect a first heat transfer 210 from the heating element 120 to the gas in the first discontinuation 162, and from the gas to the first thermal element structure 130, and may sense the same as a first sensor signal. For example, the second thermal element structure 140 may detect a second heat transfer 220 from the heating element 120 to the gas in the second discontinuation 172, and from the gas to the second thermal element structure 140, and provide the same as a second sensor signal. Due to the different distance of the first thermal element structure 130 and the second thermal element structure 140 to the heating element 120, a difference signal may be formed from the first sensor signal and the second sensor signal, as a result of which unknown transitions (e.g. a transition from the heating element to the gas and/or from the gas to the respective thermal element structure) may be calculated out, and therefore, the gas sensor 100 mainly, or only, considers the heat transfer via the gas in the first discontinuation 162 or the second discontinuation 172.

According to an embodiments, the heat sensor 100 may further comprise a frame 150 that may spread out the membrane 110. The first thermal element structure 130 and the second thermal element structure 140 may be arranged at least partially on the membrane 110 and at least partially on the frame 150. In this case, the first thermal element structure 130 and the second thermal element structure 140 may comprise hot ends 132, 142 that are arranged to face the heating element 120. In addition, the first thermal element structure 130 and the second thermal element structure 140 may comprise cold ends 134, 144 that may be arranged on a side of the thermal element structure 130 and the second thermal element structure 140, respectively, opposite the side with the hot ends 132, 142 and that are therefore arranged facing away from the heating element 120. Thus, for example, the hot ends 132, 142 may be arranged on the membrane 110, and the cold ends 134, 144 may be arranged on the frame 150. In this case, for example, the frame 150 may comprise a different material than the membrane 110. Through this, for example, a reference temperature may be applied to the cold ends 134, 144 by means of the frame material of the frame 150, with respect to a temperature measured by means of the hot ends 130, 142 and transferred from the heating element 120.

In other words, the left illustration of the gas sensor 100 may constitute a layout, and the right side of FIG. 4 may constitute an image of the gas sensor 100 (e.g. a MEMS membrane sensor) for measuring a gas type-dependent heat transport (embodiment according to aspect 1), for example. For example, FIG. 4 shows a variation of the gas sensor 100 with a constant discontinuation (e.g. a first discontinuation 162 and a second discontinuation 172) of a membrane 110. For example, the constant discontinuation 162, 172 causes a main part of a heat transport between a heater 120 and the detectors (e.g. the first thermal element structure 130 and the second thermal element structure 140), e.g., to occur compulsory via the measuring gas volume enclosed between the two elements, e.g., via the measuring gas arranged in the first discontinuation 162 and in the second discontinuation 172.

For example, in order to reduce the process effort in the technological fabrication of the gas sensor 100 and to increase the sensitivity during the measurement of the gas type-dependent heat transport 210, 220, a microchip may be realized on the basis of a thin-layer membrane 110 with heater structures 120 and thermopile structures 130, 140 (detectors), wherein the thin-layer membrane 110 may be etched out in a lateral area between the heater 120 and the detectors 130, 140.

Compared to a wire sensor (e.g. described in section 1.1.1), the membrane sensor (e.g. the gas sensor 100) only needs ⅓ of the heat energy with an identical sensitivity for the gas concentration of a binary mixture. Same as with the wire sensor, the heater structure (e.g. the heating element 120) is located as a self-supporting fine bridge structure centrally spread out in a measuring space of the gas to be detected, for example. The two detector wires arranged on both sides (e.g.) in different distances to the heater 120 may be replaced by "thermopile" structures (e.g. of the first thermal element structure 130 and/or the second thermal element structure 140) that may be located on laterally spread out membrane surfaces (of the membrane 110) and may reach up to the trench edge (e.g. an edge of the first discontinuation 162 or the second discontinuation 172), for example.

For example, the cold ends 134, 144 of the thermopiles 130, 140 should directly contact the carrier material (e.g. of the frame 150) that may have a high thermal conductivity (e.g. silicon, approximately 150 W/(*K)) and may serve as a heat sink (cooling body near room temperature). For example, the base membrane material (the material of the membrane 110), which electrically insulates the contacts from the silicon, is located between the cold ends 134, 144 of the thermopiles and the silicon. However, since this layer is very thin, the heat from the thermopiles can be effectively transferred into the silicon. In this way, the over-temperature (e.g. measured by means of the hot ends 132, 142) may be measured as a direct difference to the room temperature (e.g. measured by means of the cold ends 134, 144). For example, a measuring location for the temperature compensation is directly mechanically connected on or to the silicon chip (e.g. the frame 150).

In order to reduce a parasitic effect of the heat transport 210, 220 between the heater 120 and the detector structures 130, 140 due to a heat conduction in the membrane material of the membrane 110, the membrane 110 may be consequently interrupted such that the heat transport 210, 220 of the heater 120 to the detectors 130, 140 may be mainly carried out via a shortest lateral distance, and therefore, e.g., passes through a path across a volume of the measuring gas located in between (e.g. arranged in the first discontinuation 162 and the second discontinuation 172). As a result, the gas type-dependent transfer response (e.g. the first sensor signal and the second sensor signal) of the sensor 130/140 to periodic heat pulses of the heater 120 may be significantly increased.

Figure 5:
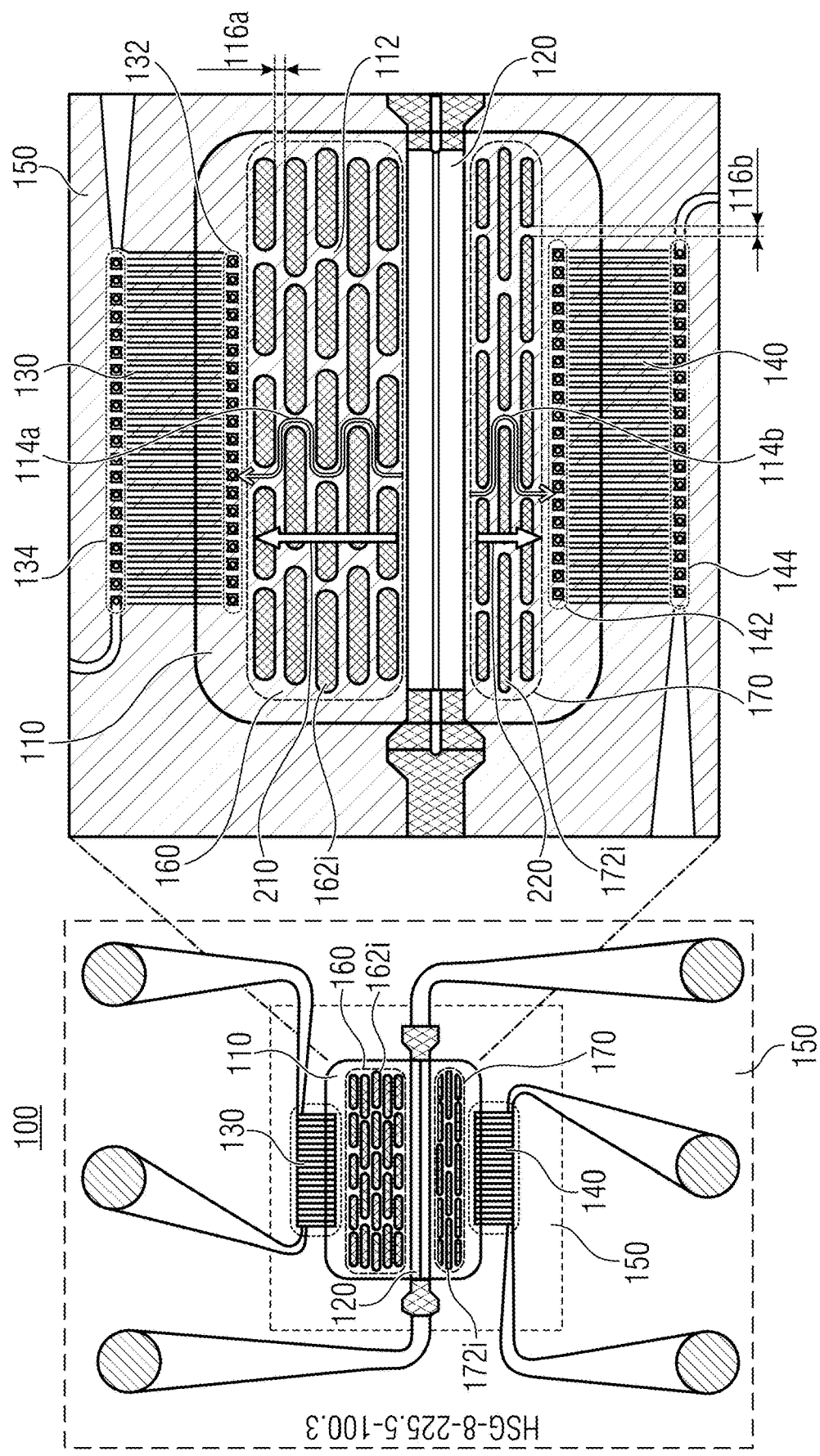
FIG. 5 shows a schematic illustration of a gas sensor with a first discontinuation area and a second discontinuation area each having a plurality of discontinuations, according to an embodiment of the present invention.

According to an embodiment, FIG. 5 shows on its left side a schematic illustration of the gas sensor 100 and on its right side an enlarged detailed view of the gas sensor 100. The gas sensor 100 of FIG. 5 may comprise the same features and functionalities as the gas sensor 100 of FIG. 4, wherein the gas sensor 100 of FIG. 5 may differ from the gas sensor 100 of FIG. 4 in a design of the first discontinuation area 160 and/or the second discontinuation area 170. Thus, for example, the first discontinuation area 160 of the gas sensor 100 of FIG. 5 may comprise a multitude of discontinuations $162_i$, and the second discontinuation area 170 may also comprise a multitude of discontinuations $172_i$. Thus, for example, the index i of the discontinuations $162_i$ of the first discontinuation area 160 of the gas sensor 100 may reach from 1 to 23 since the first discontinuation area 160 may comprise 23 discontinuations according to the embodiment in FIG. 5. For example, the index i of the discontinuations $172_i$ of the second discontinuation area 170 of the gas sensor 100 may reach from 1 to 14 since the second discontinuation area 170 may comprise 14 discontinuations according to an embodiment of FIG. 5. Optionally, the index i of the discontinuations $162_i$ and the discontinuations $172_i$ may define a natural number, for example, wherein the index i indicates how many discontinuations $162_i$, $172_i$ are present in a discontinuation area 160, 170.

The discontinuations $162_i$, $172_i$ may be arranged in the first discontinuation area 160 and in the second discontinuation area 170, respectively, in rows in parallel to a direction of maximum expansion of the heating element 120, and the rows may additionally be arranged offset to each other. For example, this means that lateral ridges 112 (e.g. extending in a direction perpendicular to a direction of maximum expansion of the heating element 120, from the heating element 120 to the respective thermal element structure 130, 140)—formed by membrane material—of successive rows are arranged offset to each other. For example, this causes a parasitic heat conduction 114a, 114b in the membrane 110 to pass through as long a path as possible.

For example, the discontinuations $162_i$, $172_i$ are arranged such that a grid structure is created in the membrane 110, wherein a path of a parasitic heat conduction 114a, 114b through the membrane 110 is longer than a direct path 210, 220. For example, a direct path 210, 220 may be a straight path perpendicular to the heating element 120, from the heating element 120 to the respective thermal element structure 130, 140, wherein the direct path 210, 220 may pass through a gas to be analyzed that is arranged in the discontinuations $162_i$, $172_i$. For example, the path of the parasitic heat conduction 114a, 114b should not extend in a straight line through the membrane 110, but should form a winding path, as is illustrated in FIG. 5. For example, there should be no direct heat path across the membrane 110. This makes it possible that the first thermal element structure 130 and the second thermal element structure 140 may detect a heat transfer from the heating element 120 via the direct path 210 and/or 220 and that influences of a parasitic heat conduction 114a, 114b may be minimized in the detection, as a result of which the gas may be analyzed very precisely.

For example, the discontinuations $162_i$, $172_i$ may be longitudinal discontinuations that may be perpendicular to a main direction of the heat conduction (e.g. the direct path 210, 220 from the heating element 120 to the thermal element structures 130, 140) with a tolerance of +/−20°.

According to an embodiment, the discontinuations $162_i$, $172_i$ may be rectangular cutouts with rounded corners. For example, they may also be referred to as a longitudinal hole, and they may also be oval holes, for example. In this case, the discontinuations $162_i$, $172_i$ may be at least three times longer than they are wide. For example, the length may be defined as a direction in parallel to a maximum expansion of the heating element 120, and the width may be defined as a direction perpendicular to the maximum expansion of the heating element 120. Due to this feature, the path of the parasitic heat conduction 114a, 114b may be realized to be very long, as a result of which a quality of the gas analysis by the gas sensor 100 may be increased.

According to an embodiment, the discontinuations $162_i$, $172_i$ in the first discontinuation area 160 and the second discontinuation area 170, respectively, may be arranged such that a distance 116a, 116b between the discontinuations $162_i$, $172_i$ corresponds to a smallest realizable structural width that results in a mechanically durable grid structure. For example, the distance 116a, 116b is a width of ridges made of a membrane material over the membrane 110. The smaller the distance 116a, 116b is realized, the smaller a parasitic heat conduction 114a, 114b may be, as a result of which a quality of a gas analysis by the gas sensor 100 may be increased. In this case, the distance 116a, 116b should be selected such that the grid structure membrane 110 created by the discontinuations $162_i$, $172_i$ is mechanically durable in order to ensure a high quality of the gas analysis by the gas sensor 100.

In other words, FIG. 5 may illustrate a layout of an MEMS membrane sensor (e.g. the gas sensor 100) for measuring the gas type-dependent heat transport (via the direct path 210, 220) (embodiment according to aspect 1), for example. Thus, the gas sensor 100 of FIG. 5 may illustrate a variation having a grid structure made of the membrane material of the membrane 110 in order to increase the mechanical stability of the gas sensor 100. The geometrical shape of the grid may be selected such that the parasitic heat conduction 114a, 114b has to pass through as long a path as possible in the membrane material.

FIG. 5 shows a further embodiment of the gas sensor 100, showing a grid structure between the heater elements 120 and the detector elements (e.g. of the first thermal element structure 130 and the second thermal element structure 140) which is to improve the mechanical stability of the gas sensor 100 in the long-term operation. Such an arrangement may decrease the gas type-dependent sensitivity of the thermal gas sensor 100 since the heat conduction may now also occur in a parasitic manner 114a, 114b via the grid ridges of the membrane material. Thus, a part of the heat energy periodically input into the heater 120 may be transported earlier to the detector structure (e.g. the first thermal element structure 130 and/or the second thermal element structure 140) than the part of the heat energy that is transported through the measuring gas via the shortest lateral distance 210, 220. Due to the thermal mass of the detectors (e.g. the first thermal element structure 130 and/or the second thermal element structure 140) that may respond to the periodic excitation as a low pass filter, for example, the two thermal wave runtimes (e.g. the parasitic heat conduction 114a with the heat transfer via the direct path 210 and/or the parasitic heat conduction 114b with the heat transfer via the direct path 220) are looped together to a single sinusoidal detector signal (e.g. to a first sensor signal or to a second sensor signal).

For example, the geometrical shape of the grid is selected such that the parasitic heat conduction 114a, 114b has to pass through as long a path as possible in the membrane material. For example, oval holes (e.g. the discontinuations $162_i$, $172_i$) are located lateral to the main direction of the heat conduction. For example, the aspect ratio of the oval holes is such that they are at least three times longer than they are wide, the ridge width (e.g. the distance 116a, 116b) corresponds to the smallest realizable structural width that results in a mechanically durable grid structure with the available layer technology, for example.

Figure 6A:
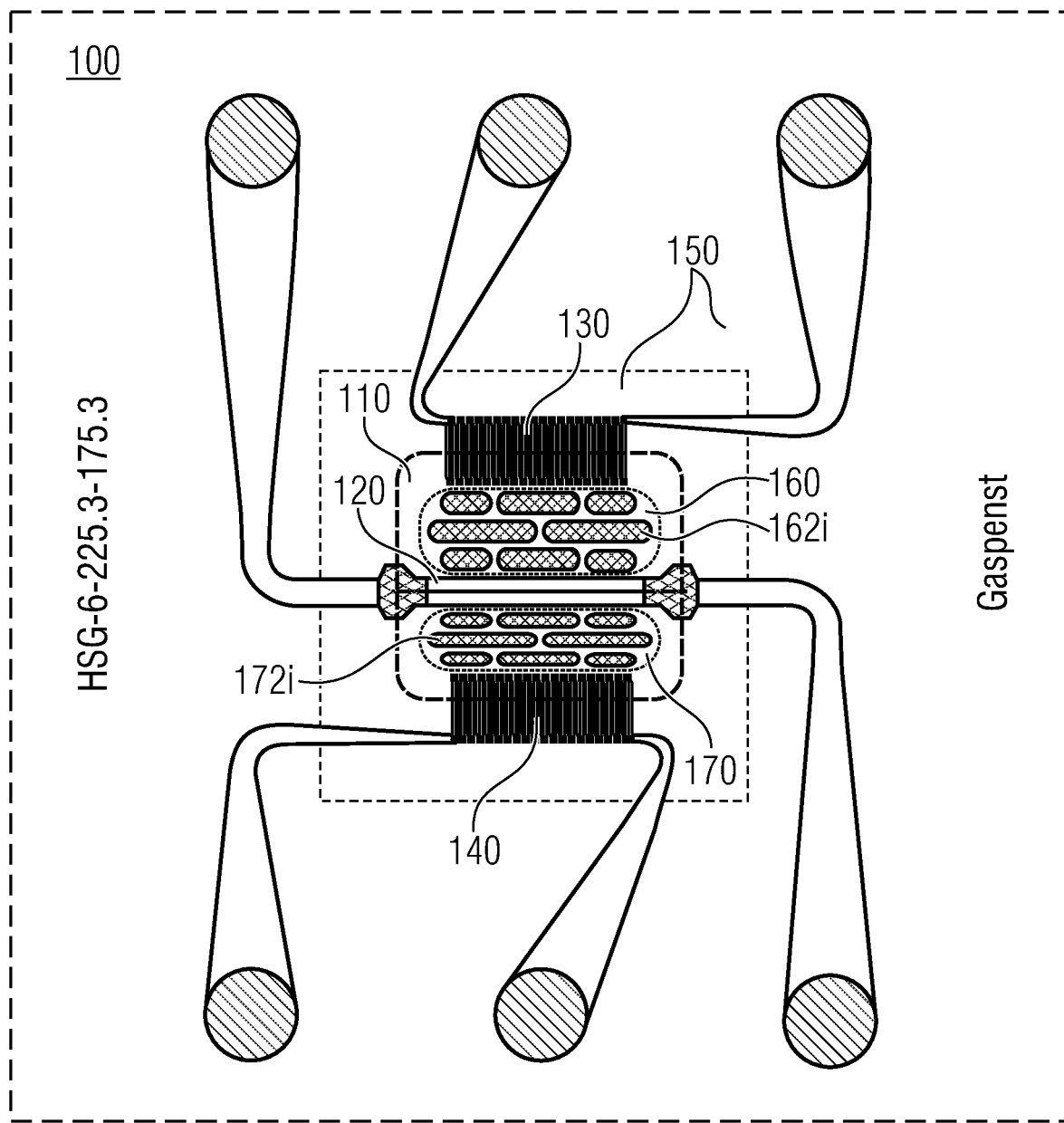
FIG. 6a shows a schematic illustration of a gas sensor with an equal number of discontinuations in the first discontinuation area and in the second discontinuation area, according to an embodiment of the present invention.
Figure 6B:
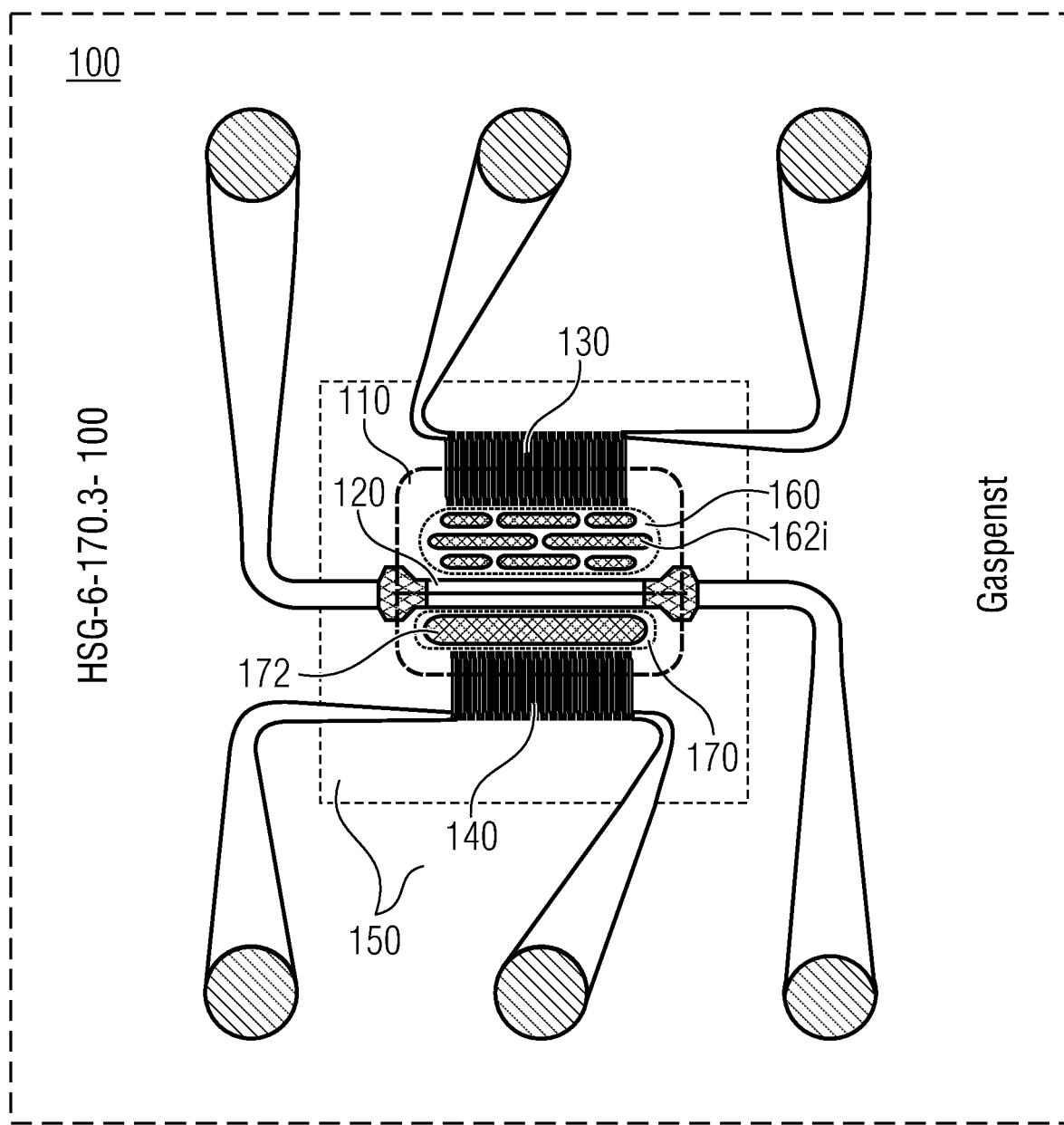
FIG. 6b shows a schematic illustration of a gas sensor with a multitude of discontinuations in a first discontinuation area and a single discontinuation in a second discontinuation area, according to an embodiment of the present invention.
Figure 6C:
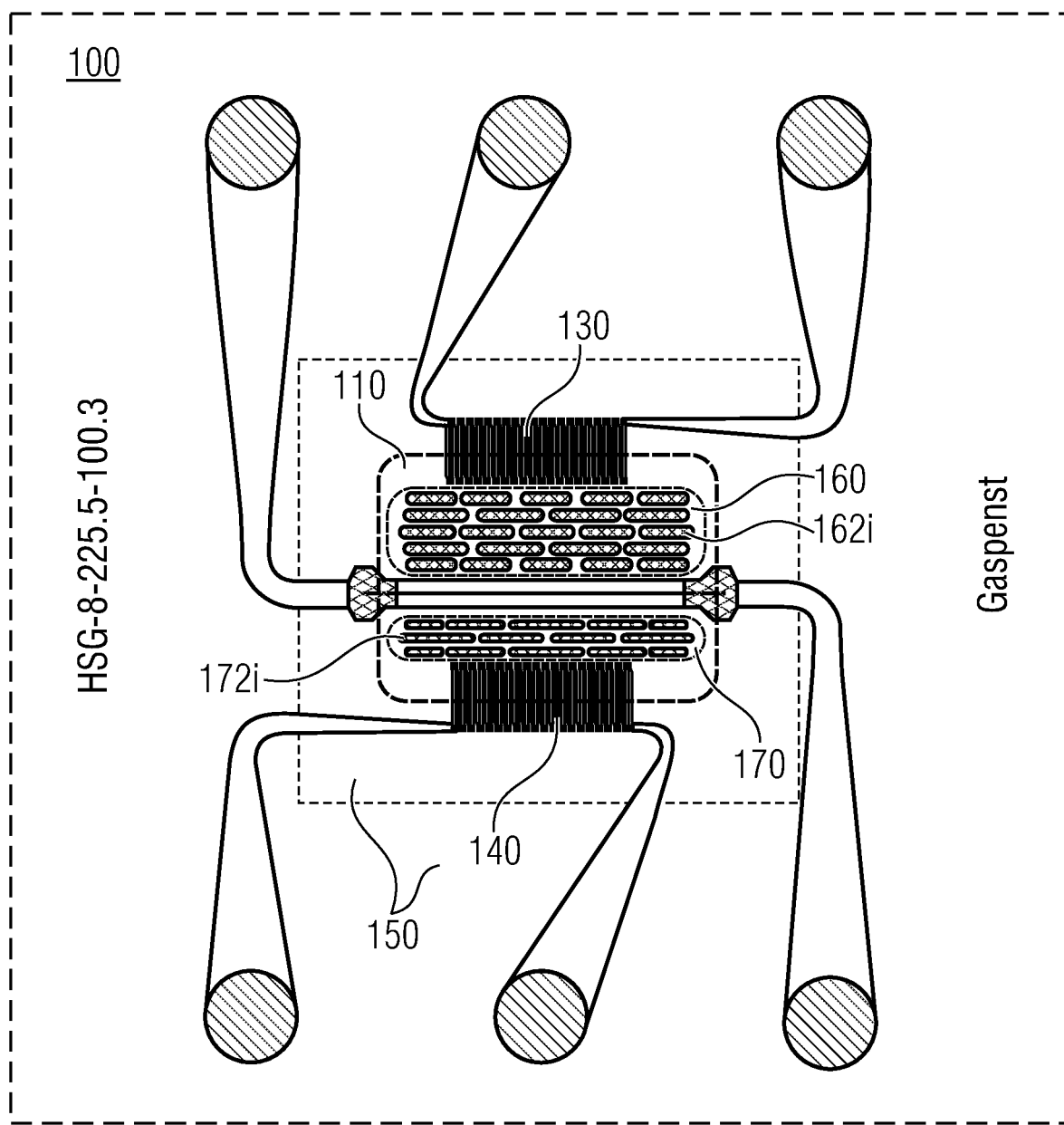
FIG. 6c shows a schematic illustration of a gas sensor, wherein a multitude of discontinuations in a first discontinuation area comprise a different expansion perpendicular to a heater than a multitude of discontinuations in a second discontinuation area, according to an embodiment of the present invention.

FIG. 6a, FIG. 6b, and FIG. 6c show schematic illustrations of further embodiments of a gas sensor 100. In this case, the gas sensor 100 of FIG. 6a, FIG. 6b, and FIG. 6c may comprise the same features and functionalities as the gas sensor 100 of FIG. 4 and/or FIG. 5. There may be differences between the gas sensors 100 in the first discontinuation area 160 and the second discontinuation area 170 of the gas sensor 100.

Thus, for example, the gas sensor 100 of FIG. 6a may comprise eight discontinuations $162_i$ in the first discontinuation area 160 and eight discontinuations $172_i$ in the second discontinuation area 170. In this case, for example, the discontinuations $162_i$ may comprise a larger lateral extension than the discontinuations $172_i$. In addition, the discontinuations $162_i$, $172_i$ may comprise different longitudinal expansions within their discontinuation areas 160 and 170, respectively.

For example, the gas sensor 100 of FIG. 6b comprises a first discontinuation area 160 with eight discontinuations $162_i$ and a second discontinuation area 170 with a continuous discontinuation 172. Thus, for example, in the variation of FIG. 6b, the variations of FIG. 6a and/or FIG. 5 and FIG. 4 are combined with each other in the discontinuation areas 160, 170.

For example, the gas sensor 100 of FIG. 6c comprises a first discontinuation area 160 and a second discontinuation area 170 with several discontinuations $162_i$, $172_i$, wherein the first discontinuation area 160 may comprise 23 discontinuations $162_i$ and the second discontinuation area 170 may comprise 14 discontinuations $172_i$, for example. In this case, for example, the continuations $162_i$, $172_i$ of a discontinuation area 160 and 170, respectively, may comprise the same lateral expansion and/or the same longitudinal expansion. Optionally, it is also possible that the discontinuations $162_i$, $172_i$ comprise only in rows the same longitudinal expansion and/or lateral expansion.

Thus, in other words, FIG. 6a, FIG. 6b, and FIG. 6c may illustrate further layout variations of the MEMS membrane sensor (e.g. the gas sensor 100), which differ in number and size of the perforations of the membrane (e.g. the discontinuations $162_i$, $172_i$) (embodiments according to aspect 1).

Advantages of the Thermopile Structures (e.g. the First Thermal Element Structure 130 and/or the Second Thermal Element Structure 140) on Membrane Technology (Examples):

- Simple 5-mask MEMS processed on cost-efficient substrates is possible since the properties of the wafer material should be specified only with respect to, e.g., thickness, surface quality and, for structuring the trench, adapted base doping. (in contrast to the gas sensor on SOI structuring of a trench (e.g. for the membrane 110)).
- For example, the structures (e.g. the heating element 120, the membrane 110, the first thermal element structure 130, the second thermal element structure 140) are passivated with protective layers and provide better resistance against free radicals that may be located in the measuring gas and that etch the active sensor structures (e.g. the first thermal element structure 130 and/or the second thermal element structure 140) and therefore mechanically weaken or thermally change them.
- For example, compared to the sensor in SOI substrate, the gas sensor 100 on a thin-layer membrane 110 only needs a third of the heating power to achieve the same gas sensitivity, the power input is approximately 12 mW in contrast to 36 mW in the SOI technology.
- Instead of temperature-variable resistance structures (RTD), thermopiles 130, 140 may be realized as detectors of a heat distribution field in the measuring space: for example, the electronic signal evaluation of the thermopiles 130, 140 is 0.6 μW, therefore almost powerless, whereas the detectors (e.g. the first thermal element structure 130, the second thermal element structure 140 of FIG. 2a, FIG. 2b, or FIG. 3) based on resistance structures of the SOI technology need a current flow for a stable signal generation, as a result of which a heating power is applied into the detector, which is at approximately 140 μW and therefore low, however, it is 200 times larger compared to the thermopile technology and contributes to the self-heating of the RTD detectors and may therefore reduce the gas selectivity in a parasitic way.

Disadvantages of the Membrane Technology:

- Fine perforated membranes 110 may break in the production process and in the long-term operation, an optimized design (e.g. FIG. 4, FIG. 5, FIG. 6a, FIG. 6b, or FIG. 6c) is favorable.

1.1.3 Sensor Principle (Details Optional)

Figure 7:
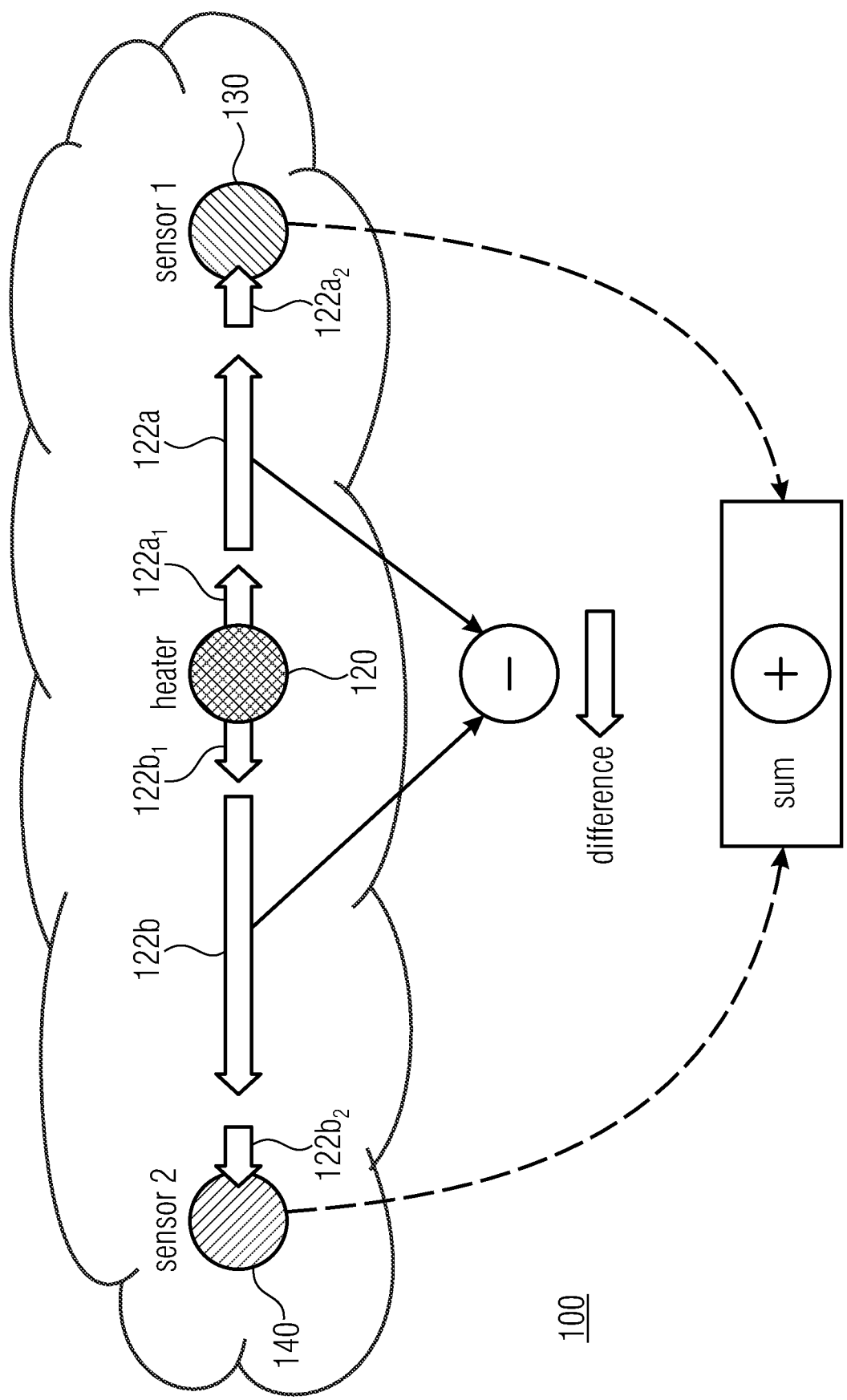
FIG. 7 shows a schematic illustration of a principle of a gas sensor according to an embodiment of the present invention.

FIG. 7 illustrates a fundamental principle of the thermal sensor 100 (the gas sensor may here also be referred to as a thermal sensor): What can be clearly seen is the spatial separation between the heater 120 and the sensor structures 130, 140 (the first temperature sensor structure and the second temperature sensor structure may here also be referred to as sensor structures, detector structures, sensors, temperature sensors or detectors) with thermal coupling by means of the gas mixture to be analyzed; and the measurement with the sensor structures 130, 140. In this case, the sensor structures 130, 140 may be arranged in different distances or in the same distance to the heater 120.

In other words, FIG. 7 shows a schematic illustration of a fundamental sensor principle for a path 122a, 122b of the heat transport between the heater 120 and the detectors 130, 140 via the gas to be measured.

The Heater 120 and the Sensors 130, 140 are Separated by a Medium

The heater 120 and the sensor(s) 130, 140 are arranged separately in the medium and are surrounded by the gas to be analyzed. For example, the heat flow 122a, 122b from the heater 120 to the temperature sensors 130, 140 is carried out only via the gas itself.

Measurement in Several Distances

For example, the heat transport 122a, 122b is also carried out via unknown heat transitions $122a_1$, $122b_1$ from the heater 120 into the gas to be analyzed, and via unknown heat transitions $122a_2$, $122b_2$ from the gas into the sensor structure 130, 140. When measuring in two distances $180_1$, $180_2$, the heat transitions $122a_1$, $122b_1$, $122a_2$, $122b_2$ are almost identical. The difference of both sensor signals essentially depends on the heat transfer by the medium itself.

Measurement in Identical Distances

Analogously to the measurement with several distances, in this case there are also unknown heat transitions $122a_1$, $122b_1$, $122a_2$, $122b_2$. A very precise gas analysis may also be performed by evaluating a sum of the two sensor signals and, under certain circumstances, the unknown heat transitions $122a_1$, $122b_1$, $122a_2$, $122b_2$ may also be considered in the analysis.

It is to be noted that, when measuring in several distances, a sum signal may be evaluated as an alternative.

It is further to be noted that evaluating a sum signal is advantageous to evaluating a difference signal since a signal-noise distance of the difference signal is smaller than in the sum signal.

Optionally, a quotient of a difference signal and sum signal (which is a common standardization) may be used for the evaluation. For example, this highlights the measuring effect more strongly as is the case if only the sum signal or only the difference signal is evaluated.

Electrical Analogy

An electrical analogy has been created (cf. FIG. 8, for example) in order to identify and estimate the heat flows. Optimizing the heat loss is an essential factor in order to increase the sensitivity of the sensor 130, 140 without having to feed in too large of a heating power, e.g. via the heating element 120.

Figure 8:
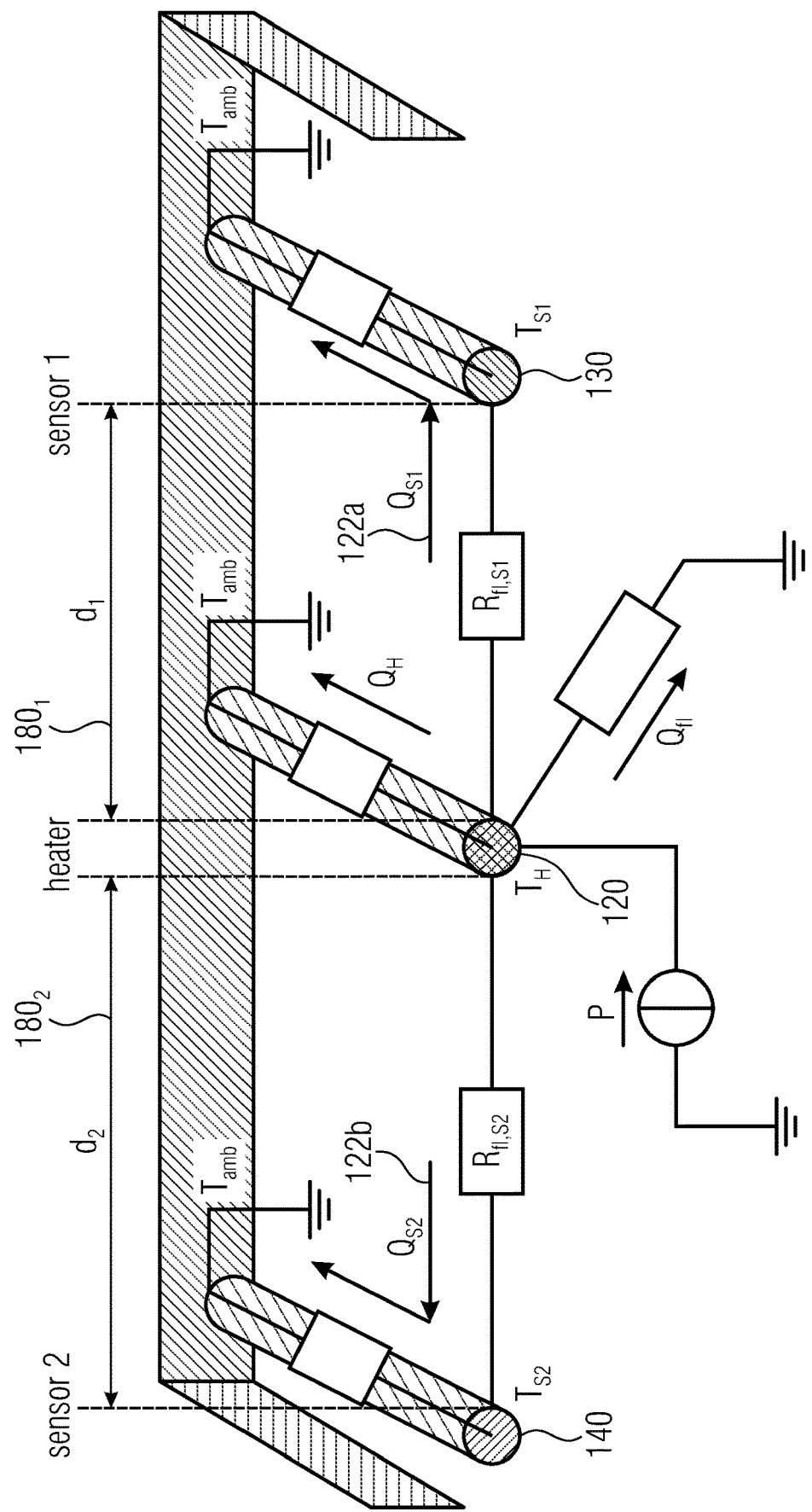
FIG. 8 shows a schematic illustration of a heat transport at a gas sensor according to an embodiment of the present invention.

According to an embodiment, FIG. 8 comprises features and functionalities of the gas sensor 100 of FIG. 7. In other words, FIG. 8 shows a schematic illustration of the heat transport at the gas sensor 100. The heat transport from the heater 120 (temperature $T_H$) to the sensor 130, 140 (temperature $T_S$) essentially takes place via the gas to be measured.

1.2 Embodiment of the Gas Sensor in Operation: Signal Generation and Signal Evaluation on an Embedded System 1.2.1 Functional Principle (Details Optional)

With a sinusoidal heating power 122, there is a sinusoidal progression of the sensor signals 210, 220 (e.g. FIG. 9, for example) that strongly depends on the thermal properties of the gas surrounding the sensor structures. By measuring the temperature of the heater 120 with two identical sensors 130, 140 in different distances $180_1$, $180_2$ to the heater 120, the unknown heat transition in the measuring arrangement may be eliminated or reduced.

Figure 9:
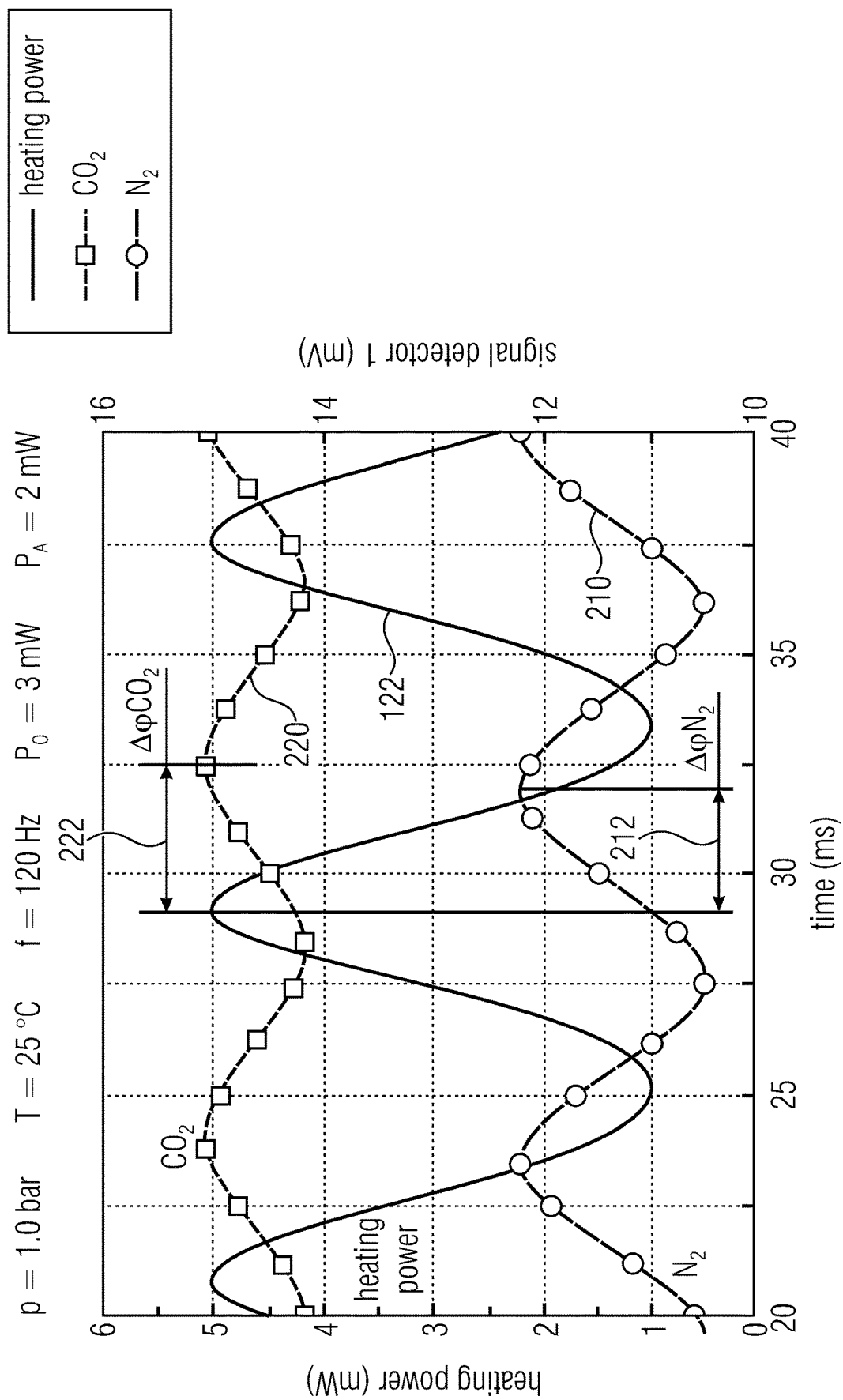
FIG. 9 shows a diagram of a heater signal, a first sensor signal, and a second sensor signal of a gas sensor according to an embodiment of the present invention.

In the evaluation, emitted and received periodic temperature waves are compared (cf. FIG. 9). A calibration of the signal 210, 220 through the phase shift 212, 222 between the heater and the sensors, for example, may be used to resolve the $CO_2$ content in the air as being 0.2 vol %, e.g. by means of the gas sensor. Since gases may be compressed and change their density through pressure and temperature, the corresponding drifts should be compensated.

FIG. 9 shows signals 210, 220 upon excitation with a sinusoidal heating power 122 in comparison for $CO_2$ and $N_2$. With the same heating power 122, the sensor signals 210, 220 received differ with respect to their amplitude, offset and phase position. According to an embodiment, the signals 210, 220 are difference signals of a signal of a first thermal element structure and a second thermal element structure of the gas sensor.

By evaluating further measuring quantities that the sensor provides, the thermal conductivity, the thermal diffusivity and, if the density of the gas is known, also the specific heat capacity may be determined—a possible approach to analyze unknown gas mixtures as well.

Through the structural difference of self-supporting bridge structures compared to thin-layer membranes, parasitic thermal decoupling between the heater and the detector elements is mostly achieved, and the signal quality is significantly increased. Due to the low thermal mass of the heater, it is possible to modulate the heater with frequencies of up to 300 hertz since the heat may be quickly provided and dissipated.

1.2.2 Theoretical Consideration for Determining the Thermal Diffusivity (Details Optional)

In order to determine the thermal diffusivity at a sinusoidal heating power 122, a model according to [Baehr 2008] may be used to describe the propagating temperature field.

The following equation describes the time-dependent (time t) a temperature propagation along the longitudinal axis x in a rod that has a sinusoidal temperature applied at one end (mean value $T_m$, amplitude $T_A$, angle frequency $\omega$):

$$T(x,t) = T_m + T_A \cdot \eta \cdot e^{-k_1 \cdot x} \cdot \sin(2\pi f \cdot t - (k_1 \cdot x + \in)) \quad (1)$$

When entering into the gaseous medium from the heater, the temperature field experiences the phase shift $\in_0$ and the attenuation $\eta_0$.

$$\epsilon_0 = \arctan\frac{k}{1+k} \text{ and } \frac{1}{\eta_0} = \sqrt{1 + 2k + 2k^2} \quad (2)$$

Dependent on the path x covered by the medium, the temperature field experiences the phase shift $\in(x) = k_1 \cdot x$ and the attenuation $\eta(x) = e^{-k_1 \cdot x}$. The essential factor for the change of the path-dependent values, $k_1$, depends on the thermal diffusivity a, the angular frequency $\omega$, and therefore on the excitation frequency f, according to [Baehr 2008]:

$$k_1 = \sqrt{\frac{\omega}{2 \cdot a}} = \sqrt{\frac{\pi \cdot f}{a}} \quad (3)$$

The factor for considering the influences in the heat transfer between a solid body and a gas results from the factor $k_1$, the heat transfer coefficient $\alpha$, and the thermal conductivity $\lambda$:

$$k = \frac{k_1 \cdot \lambda}{\alpha} = \frac{b}{\alpha} \cdot \sqrt{\pi \cdot f}$$

with the heat penetration coefficient b:

$$b = \sqrt{\lambda \cdot c_p \cdot \rho} = \frac{\lambda}{\sqrt{a}} \quad (4)$$

In order to determine the thermal diffusivity according to the above-mentioned model, the evaluation of the phase shift is sufficient. The total phase shift in equation (1) amounts to:

$$\Delta\varphi = k_1 \cdot x + \in_0 \quad (5)$$

When comparing two temperature measurements in two different distances, the constant heat transition effects cancel each other out:

$$\Delta\varphi(x_2) - \Delta\varphi(x_1) = (k_1 \cdot x_2 + \in) - (k_1 \cdot x_1 + \in) \quad (6)$$

Simplified with the differences $\Delta\varphi_{12} = \Delta\varphi(x_2) - \Delta\varphi(x_1)$ and $\Delta x_{12} = x_2 - x_1$ $$\Delta\varphi_{12} = k_1 \cdot \Delta x_{12} \quad (7)$$

and with (3), the following results:

$$\Delta\varphi_{12} = \sqrt{\frac{\pi \cdot f}{a}} \cdot \Delta x_{12} \quad (8)$$

The following applies for the thermal diffusivity a (with angles in the circular measure):

$$a = \pi \cdot f \cdot \frac{\Delta x_{12}^2}{\Delta\varphi_{12}^2} \quad (9)$$

If the phase shifts are available in degrees, the following applies for the thermal diffusivity a:

$$a = \frac{180°^2 \cdot f2}{\pi} \cdot \frac{\Delta x_{12}^2}{\Delta\varphi_{12}^2} \quad (10)$$

The temperature wave oscillates harmonically at the same angular frequency as its excitation and decays rapidly and strongly attenuated with increasing penetration depth in the medium, while the phase shifts increases. The penetration depth and wave length increase as the oscillation duration and thermal diffusivity of the medium increase. When considering the wavelength $\wedge$ of the temperature oscillation, which results from the distance between two measuring points $x_1$ and $x_2$ at which the phase angle differs by $2\pi$, the penetration depth of the temperature wave may be derived, where the temperature amplitude has decreased to the n-th part of its value at the entry point into the medium x=0. The following applies:

from $e^{-2\pi x_n/\wedge} = 1/n$, the following applies:

$$x_n = \frac{\Lambda}{2\pi} \cdot \ln n = \sqrt{\frac{a}{\pi \cdot f}} \ln n \qquad (4)$$

Thus, the attenuation of the amplitude is also a measure for the thermal diffusivity of the medium.

1.2.3 Theoretical Consideration for Determining the Thermal Conductivity (Details Optional)

The thermal conductivity λ of the medium is represented by the mean temperature distribution in the measuring space. Dependent on the mean heater temperature and the gas type and/or mixture concentration in the volume of the measuring space, a mean temperature arises at the temperature detectors, said mean temperature being in proportion to the heat flow that flows through the gaseous medium from the heater to the housing wall via the detectors. The temperature of the heater and that of the detectors have to be known to determine the thermal conductivity, e.g. with an appropriate calibration, it is sufficient to control a detector (the detector closer to the heater) to a constant (over) temperature if the needed mean heating energy is determined as a measure of the thermal conductivity.

According to [Simon 2002] and [Baar 2001], the fundamental principle for measuring the thermal conductivity of gases is that an over temperature above the ambient temperature is generated in a flow-free measuring space with a heater element (e.g. a hot wire or a "hot plate") that is free-standing in the gas. The heating power needed to maintain this over temperature ΔT is the direct measure of the thermal conductivity λ and may be described with the following relationship:

$$P = \lambda \cdot \Delta T \cdot G \qquad (5)$$

wherein G represents the geometric constant of the arrangement. The condition for correct measurement is a stationary gas in the measuring space, e.g. in a dead volume or behind a diffusion barrier, since convective heat flow leads to a measuring error [Baar 2001]. These measuring errors are discussed in the literature, where methods that may measure the thermal conductivity in the presence of convective heat flow are also proposed [IST AG 2011, 2013, 2015]. Furthermore, methods with a periodic excitation of the heater are known, which may determine not only the concentration of binary gas mixtures but also mixtures of several components by Fourier analysis [Grien 2012].

1.2.4 Embedded Microcontroller, Electronic System and Software of the Inventive Gas Sensor (Details Optional)

The object of the electronic system and signal evaluation is to generate, e.g., a reliable measuring result that directly depends on the gas concentration with a miniaturized system that is as inexpensive as possible. In addition, the inventive gas sensor should be usable in a respiratory gas monitor in which the carbon concentration in the air mixture may change very dynamically. Thus, the gas sensor should be able to resolve changes in the gas composition in the respiratory cycle of inspiration and expiration up to a rate of 60 strokes per minute. Thus, a fast evaluation of the sensor signals is desirable.

1.2.4.1 Hardware 1.2.4.1.1 Example: Heater Control of the Inventive Gas Sensor (Embodiments According to Aspect 3, Details Optional)

Figure 10:
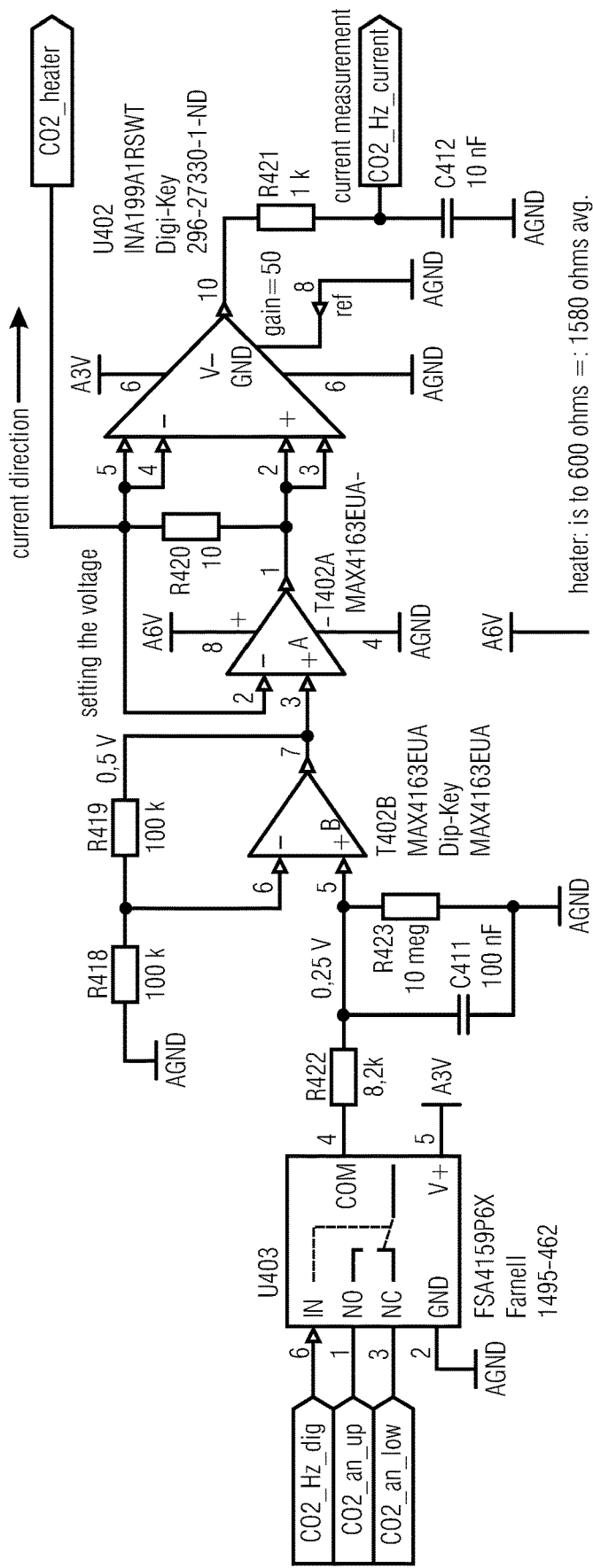
FIG. 10 shows a schematic illustration of driving a heater for a gas sensor according to an embodiment of the present invention.

FIG. 10 shows an electric circuit diagram of a heater control for a thermal gas sensor according to an embodiment of the present invention. For example, a CPU specifies a lower and upper heater voltage and switches timers in a controlled manner back and forth between these two values. A CPU may measure the current heating current at certain points in time in order to calculate the heating power. In other words, FIG. 10 illustrates a heater supply with a voltage specification and a current measurement.

In contrast to the analogy in the above theoretically-considered analogy in the transfer of the principles for an attenuated oscillation to a heat transport phenomenon using the example of a sinusoidal heater excitation, (e.g.,) a square-wave signal is generated on the developed microcontroller electronic system. Due to the timer structures in the processor, this signal may be generated much more precisely than a synthetic sinusoidal signal that would be output by the processor on its digital/analog (DA) port.

For example, 2 heater voltages are specified via a DA converter. This is due to the fact that the DA converter is controlled via SPI, and that the point in time at which a new DA value is adopted may not be determined exactly with the selected processor component (CPU). However, this is a prerequisite in order to be able to determine the phase position of the sensor response. Thus, for example, one of the two voltages is alternately applied to the heater amplifier via an analog switch. For the steep switching edges to propagate less in the system, for example, they are smoothed out by a downstream low-pass filter. The operational amplifier (OP) circuit raises the voltage onto the voltage level needed by the heater. For example, a further OP compensates the voltage drop at the current measurement resistor. Since the current is measured and the heater voltage is known, the heater power may be calculated. This is important because the heater resistance may change with the temperature.

For example, a heater duty cycle of 50% may be used (wherein, e.g., a periodic square-wave signal with a duty cycle of 50%+/−2% is applied to the heater, for example).

Alternatively, shorter duty cycles may be used, e.g., in the range of 5 . . . 50%.

In order to obtain the same power between a sinusoidal wave (offset at Upp/2, both half-waves in the positive range) and a square wave, a duty cycle of 42% is needed for an "equivalent" square-wave signal or a square-wave signal with the same power.

In some embodiments, adapting the heater power by controlling the duty cycle is not realized—this is more difficult on the MSP430, but interesting when using more powerful microcontrollers: a fixed operating voltage may be used, and the duty cycle may be changed (a type of PWM control).

In other words, it is optionally possible to set the (mean) heater power by changing the duty cycle. Alternatively, the heater power may be set by changing the voltage level (of the voltage applied to the heater), or the current level (of the current flowing through the heater, or the heating element). The two options may also be combined.

1.2.4.1.2 Example: Detector Signal Evaluation of the Gas Sensor (Details Optional)

Figure 11:
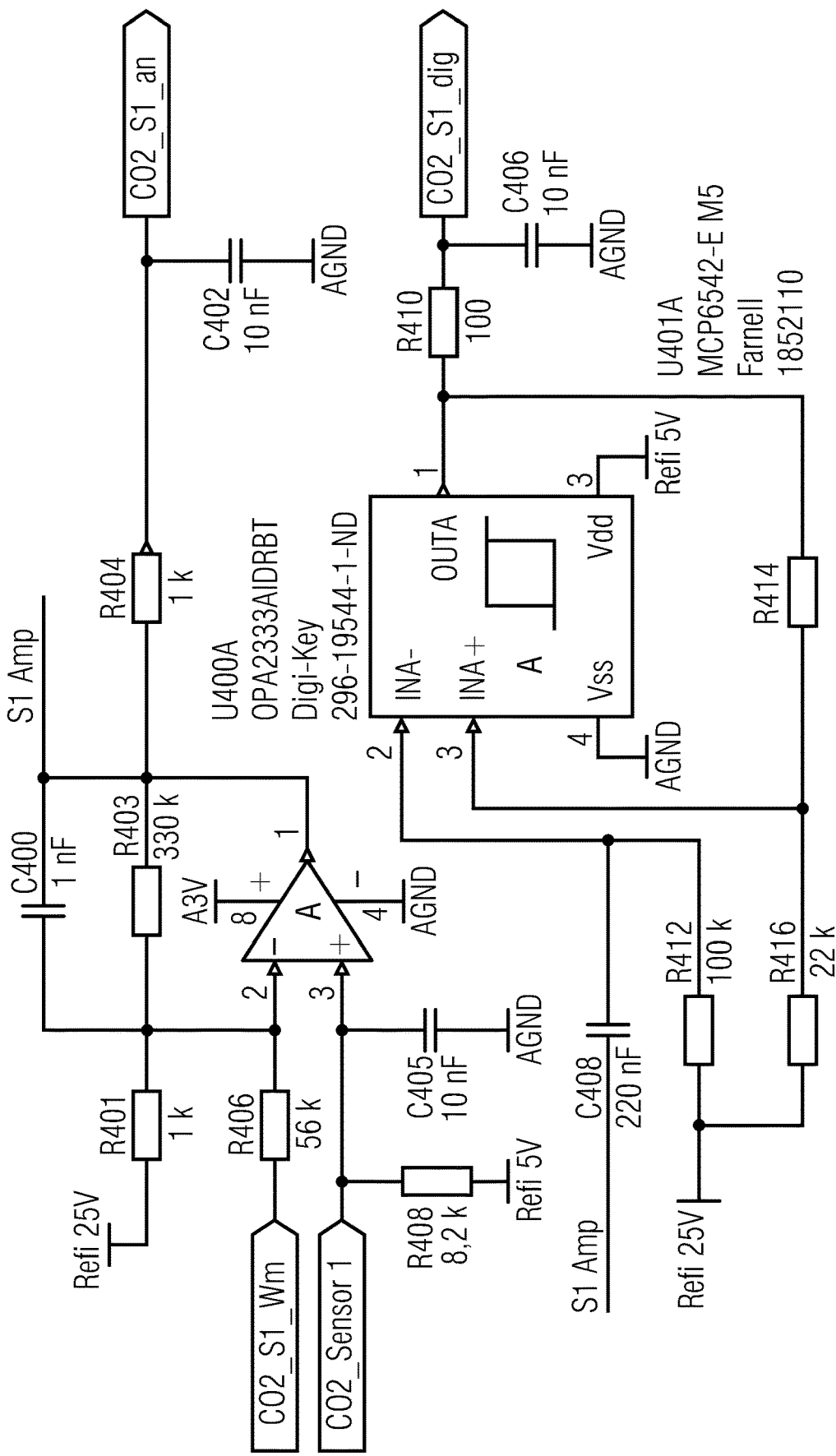
FIG. 11 shows a schematic illustration of a circuit for evaluating a sensor signal of a gas sensor according to an embodiment of the present invention.

FIG. 11 shows an electric circuit diagram of a detector signal evaluation of a thermal gas sensor according to an embodiment of the present invention. In this case, a first thermal element structure and a second thermal element structure of the gas sensor may comprise the detector signal evaluation illustrated in FIG. 11 in order to evaluate, in a respective detector signal (e.g. detected by means of the first thermal element structure or the second thermal element structure, and may also be referred to as a sensor signal herein), heat transferred from a heating element of the gas sensor to the first thermal element structure and the second thermal element structure via a gas to be analyzed. According to an embodiment, FIG. 11 illustrates the detector signal evaluation of the sensor 1 (first thermal element structure). In this case, e.g., the detector signal evaluation is configured to receive a first input signal, e.g. a DAC signal CO2_S1_Win, from a CPU (magnifying glass function), and a second input signal, e.g. a detector signal CO2_Sensor1, and to provide a first output signal, e.g. an amplified detector signal CO2_S1_an, and a second output signal, e.g. a comparator signal for a phase evaluation CO2_S1_dig.

According to an embodiment, a CPU controls a heater such that an amplitude of the sensor signal remains within a ADC range. For example, the sensor signal is kept within the ADC boundaries via a magnifying glass function. For example, a phase evaluation is carried out via the comparator using the MSP430 timer structures (time structures).

A resistance change of the sensor wire (e.g. of the thermal element structure) is very low. For this reason, an amplifier having a high amplification factor is advantageous or needed. Since an absolute value of an input voltage (e.g. of the sensor signals) depends on many factors, it is recommended to compensate for this value.

One possibility would be to use an alternating current (AC) amplifier. The disadvantage is that it causes an unknown phase shift.

Therefore, for example, a direct current (DC) amplifier has been used, which does not have any phase shift. In order to compensate for the DC component of the signal, in an embodiment, the negative input terminal is raised to mean value of the detector signal at the differential input of the operational amplifier (OP), and is actively tracked by means of a software controller, the digital-analog converter (DAC) of the processor directly outputs this voltage. Due to the differential operation of the differential input at the OP, the DC components of the input voltages are subtracted from each other, and only the AC component of the signal is amplified. To this end, according to an aspect, the (ADC) signal converted from analog to digital is measured, and an examination as to whether it is within reasonable boundaries that may be detected by the ADC is carried out. If the signal hits the upper or lower voltage limit of the OP, the DAC value is adapted accordingly. This results in an amplifier in which the amplified signal is continuously kept in the optimum operating range or operating window, where the amplification factor at the OP may be increased by removing the DC component, a type of "magnifying glass function". The DAC value needed for the compensation may be used as a further parameter for the evaluation, with which the absolute mean temperature may be determined, and the thermal conductivity of the gas mixture may be determined via the relationship from equation (5).

In order to determine the phase position of the sensor signal, for example, a Schmitt trigger was used. It is set such that it switches shortly above or below the zero crossing of the sensor signal. Here, the signal is steepest and therefore causes the smallest phase noise. For example, the DC component is removed via a capacitor. This enables a phase determination of the sensor response.

By using the internal timer structures of the processor (MSP430, Texas Instruments), a theoretical phase resolution of 0.009° is possible. However, this is not achieved due to noise of the circuit.

1.2.4.2 Example: Software (Details Optional; Functionalities According to Aspects 3 and 4 are Described Together, but May be Used Separately) for the Gas Sensor For example, the software has different tasks:

Setting the start values for the heater voltage, the sampling times of the sensor signals and the start value for the DC operating point (magnifying glass function).

Initially, for example, an attempt is made to find the DC operating point. To this end, the DAC values of the two sensors are set such that the sensor signal is centered in the ADC range, for example.

Measuring the sensor voltage at certain points in time. In order to determine the amplitude, the voltage is detected at the assumed maximum and minimum. In order to recognize that the sampling time has been selected incorrectly, another measurement is made at the assumed "zero crossing". If the sampling times are correct, the following applies, for example:

$$\frac{Umax + Umin}{2} = U0$$

If the sampling times are incorrect, the above equation is no longer correct. For example, the software may recognize from this that the sampling times have to be adapted. For example, the readjustment may be deactivated via software. It is only carried out if the signal is within the ADC boundaries.

If the amplitude controller is active, an attempt is made, for example, to keep the amplitude of the Sensor1 signal at a certain target value. For example, the heater energy is adjusted such that the S1 amplitude fills the ADC range by at least ¾. The controller may optionally be switched off via software. In addition, for example, it is only active if sampling times or DC offsets have not been changed. This optionally ensures that this control loop is only active in the steady state.

Determining the phase position of the sensor signal with the help of the Schmitt trigger circuit (optional). Dependent on the setting, the calculation of the 3 sampling times of the sensor signal for the next sampling period is also carried out here.

The ambient pressure and the temperature are detected via further sensors (optional)

1.2.4.3 Example: Software Controller (Details Optional) for the Gas Sensor

Figure 12:
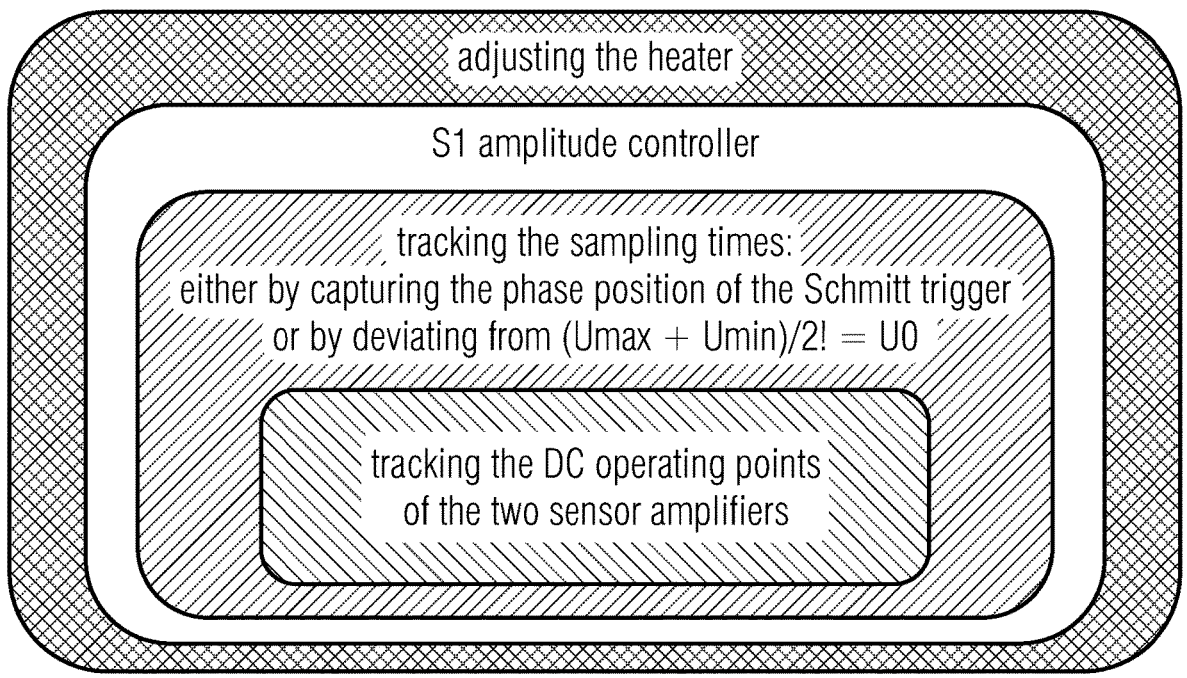
FIG. 12 shows a schematic illustration of a control of a gas sensor according to an embodiment of the present invention.

FIG. 12 shows a schematic illustration of interleaved controllers of the software for a thermal gas sensor according to an embodiment of the present invention.

Several interleaved controllers operate in the software. The innermost one is the DC operating point controller. For example, only if it is in a steady state (the DC offset did not have to be adapted), tracking the sampling times is carried out. In the amplitude control loop, e.g., the amplitude of S1 is kept constant—but only if, for example, the DC offset and the sampling time did not have to be adapted. In the outer control loop, the heating energy needed for adjusting the S1 amplitude may be (optionally) adjusted such that the thermal system may dynamically adapt itself to a large bandwidth of certain gas mixtures.

For determining the amplitude, for example, 3 A/D samples per sensor wire are needed: minimum at the lower peak, zero crossing, and maximum at the upper peak. For example, the process is as follows:

For example, all AD values are initially measured with the current setting.

Now, for example, an examination as to whether the min/max A/D values for S1 and S2 are in the valid range is carried out. If this is not the case, the DC operating point of the amplifier is readjusted (via DAC), and all further controllers are temporarily switched off. Only when both sensor channels are within the allowed operating range ($A/D_{max}$<3900, or $A/D_{min}$>200, i.e. in the range from 5 ... 95% of the A/D range of 4096 digits), the further controllers become active again.

To ensure a correct measurement of the amplitude, the A/D conversion should be carried out at the correct time (upper/lower peak, and at the zero crossing for verification). Currently, for example, there are two ways to do this:
- Through the A/D conversion itself: the time of the zero crossing is expected in half the time between the two measured times for the minimum and maximum peak of the A/D values, i.e. (min+max)/2 should correspond to the A/D value at the zero crossing. In case of deviations, the sampling time for the next measurement is adapted. For example, a deviation of approximately 0.625° (degrees) or 14.47 µs is tolerated.
- Through the comparator signal: since the comparator switches at the time of the zero crossing of the sensor signal, for example, the time at which the A/D measurements are to be carried out may be determined: at the measuring value of the switching time of the positive edge, 90° (or 2.0833 ms for the upper peak), 180° (4.1666 ms for the zero crossing of the negative edge), and 270° (6.2499 ms for the lower peak) are added. Here, a deviation of 0.625° is also tolerated.

For example, only if both controllers (DC operating point and phase) did not require a change of control values, and were therefore in the steady state, then the amplitude controller will take effect. It readjusts the heater value such that the desired amplitude of S1 is achieved.

Figure 13A:
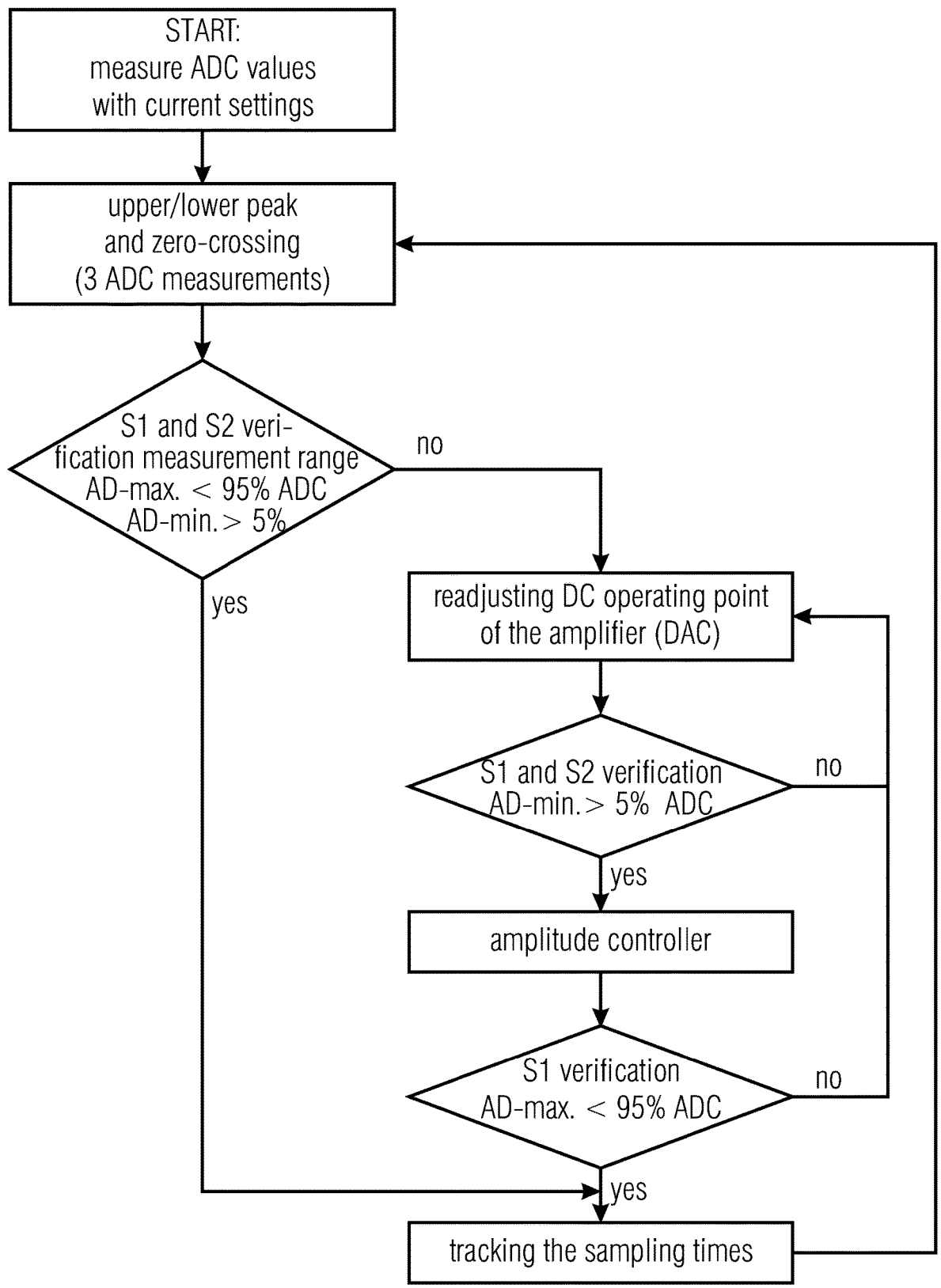
FIG. 13a shows a block diagram of a method for analyzing a sensor signal of a gas sensor according to an embodiment of the present invention.

FIG. 13a shows a block diagram illustrating the control and tracking of the DC operating points of the two detector amplifiers according to an embodiment of the present invention.

Figure 13B:
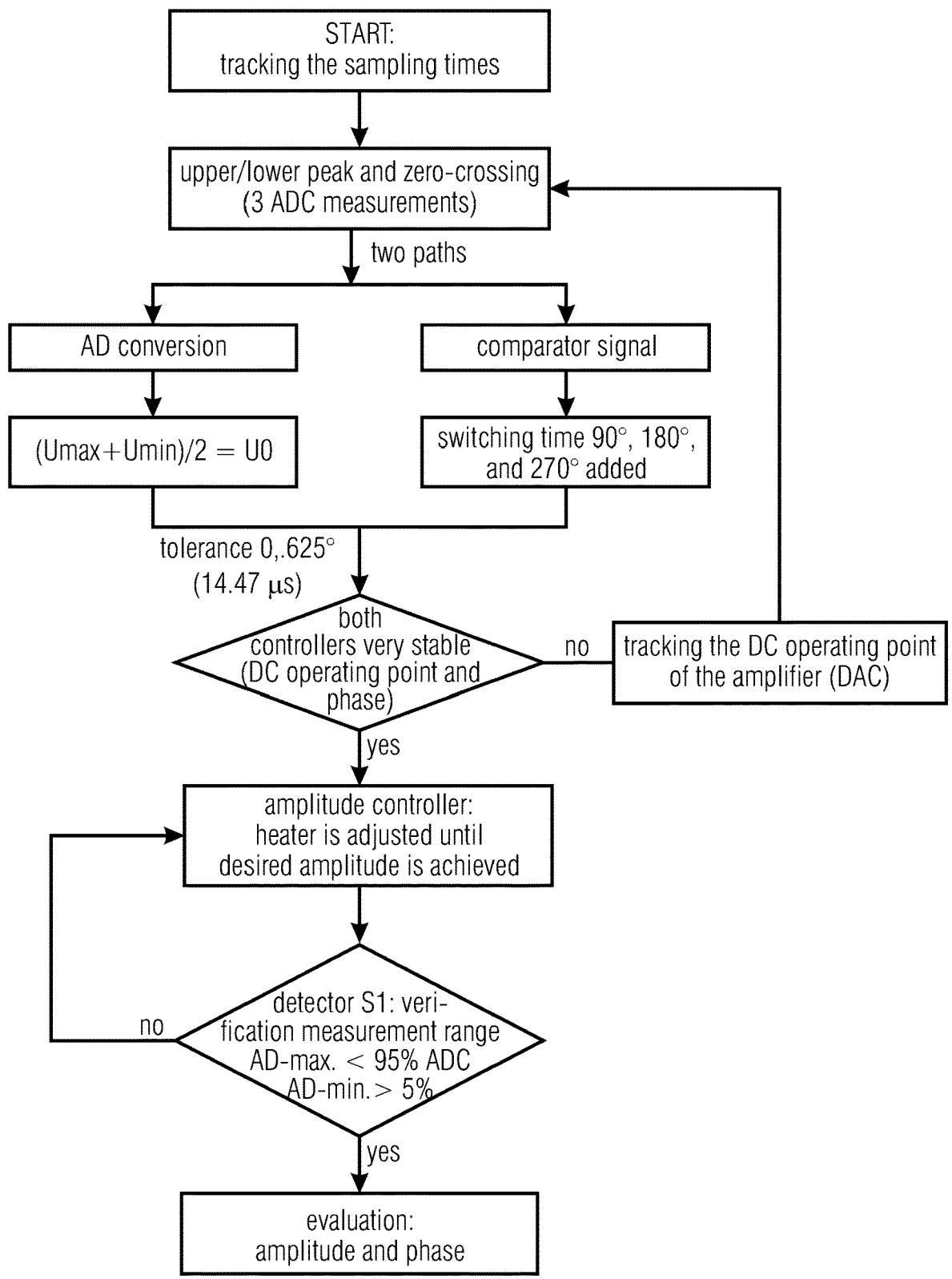
FIG. 13b shows a block diagram of a method for evaluating a sensor signal of a gas sensor with tracking sampling times, according to an embodiment of the present invention.

FIG. 13b shows a block diagram illustrating the tracking of the sampling times for the amplitude measurements of the detectors signals and S1 amplitude controllers. If all controllers are tuned, for example, the gas mixture is evaluated with the measured values for the amplitude and phase of the detectors.

According to an embodiment, FIGS. 13a and 13b may be considered to be one block diagram, where FIG. 13b is connected to FIG. 13a via the block "tracking the sampling times".

1.2.4.4 Example: Timing Table (Details Optional) for the Gas Sensor

For example, the ADC measuring times at which the analog-digital converter of the microcontroller measures the current consumption of the heater and the detector voltages (an example for the sensor signals) are defined in a timing table of the software extending across two heater pulse periods. According to an embodiment, these two periods are needed, e.g., since only one timer is available on the processor used for the variable ADC control. If the heater is operated at 120 Hz, all measuring values relevant for the gas mixture evaluation are obtained after 2 periods, i.e. with a frequency of 60 Hz. Since the pulse shape of the heater is stable across the period, the input heater current may be measured at fixed times: at 45° for the peak value and at 170° for the lower heat current value (generally zero). The respective 3 ADC measuring values per detector (upper and lower peak, and zero crossing) are expected as variable measuring values in time windows that are defined in the timing table:

ADC_SENSOR1:
 CO2-S1-min: 33.6° ... 123.6° (778 µs ... 2861 µs)
 CO2-S1-Null: 123.6° ... 213.6° (2861 µs ... 4944 µs)
 CO2-S1-max: 213.6° ... 303.6° (4944 µs ... 7028 µs)

ADC_SENSOR2:
 CO2-S2-min: 68.6°-141.4° (1588 µs ... 3273 µs)
 CO2-S2-Null: 158.6°-231.4° (3671 µs ... 5356 µs)
 CO2-S2-max: 248.6° ... 321.4° (5755 µs ... 7440 µs)

Figure 14:
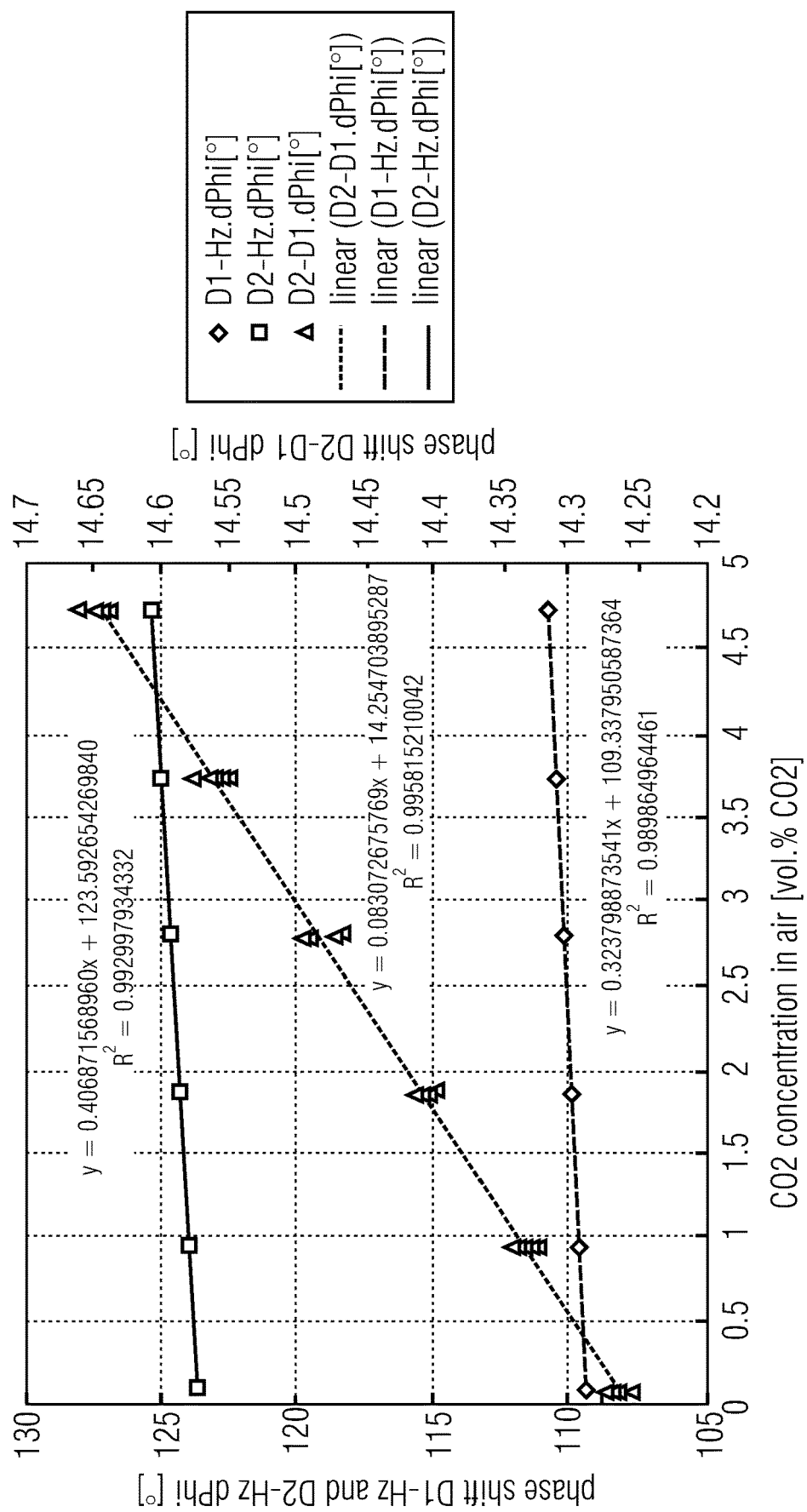
FIG. 14 shows a diagram of a phase shift between a heater signal and two sensor signals of a gas sensor according to an embodiment of the present invention.

1.3 Example: Evaluation Algorithm for Calibration with Respect to a Gas Mixture with Drift Correction for Gas Pressure and Gas Temperature (e.g. According to Aspect 2; Details Optional) of a Gas Sensor 1.3.1 Measurements in Gas Mixtures 1.3.1.1 Binary Mixture FIG. 14 exemplarily shows a $CO_2$ dependence of the sensor in the phase signal at a constant temperature and constant pressure. Here, for example, three phase shifts are illustrated; a phase difference D1-Hz.dPhi (red) between the heater and the detector 1, with a distance of 200 µm, a phase difference D2-Hz.dPhi (blue) between the heater and the detector 2, with a distance of 300 µm, and a phase difference D2-D1.dPhi (green, right y axis) between the detector 2 and the detector 1. According to an embodiment, FIG. 14 illustrates phase shifts between the heater and the detectors for (0 ... 5) vol % of $CO_2$ in the air at a pressure of p=1010 mbar, a temperature of $T_{amp}$=24° C., and a heating power of P=(15±12.5) mW at a frequency of f=120 Hz.

Figure 15:
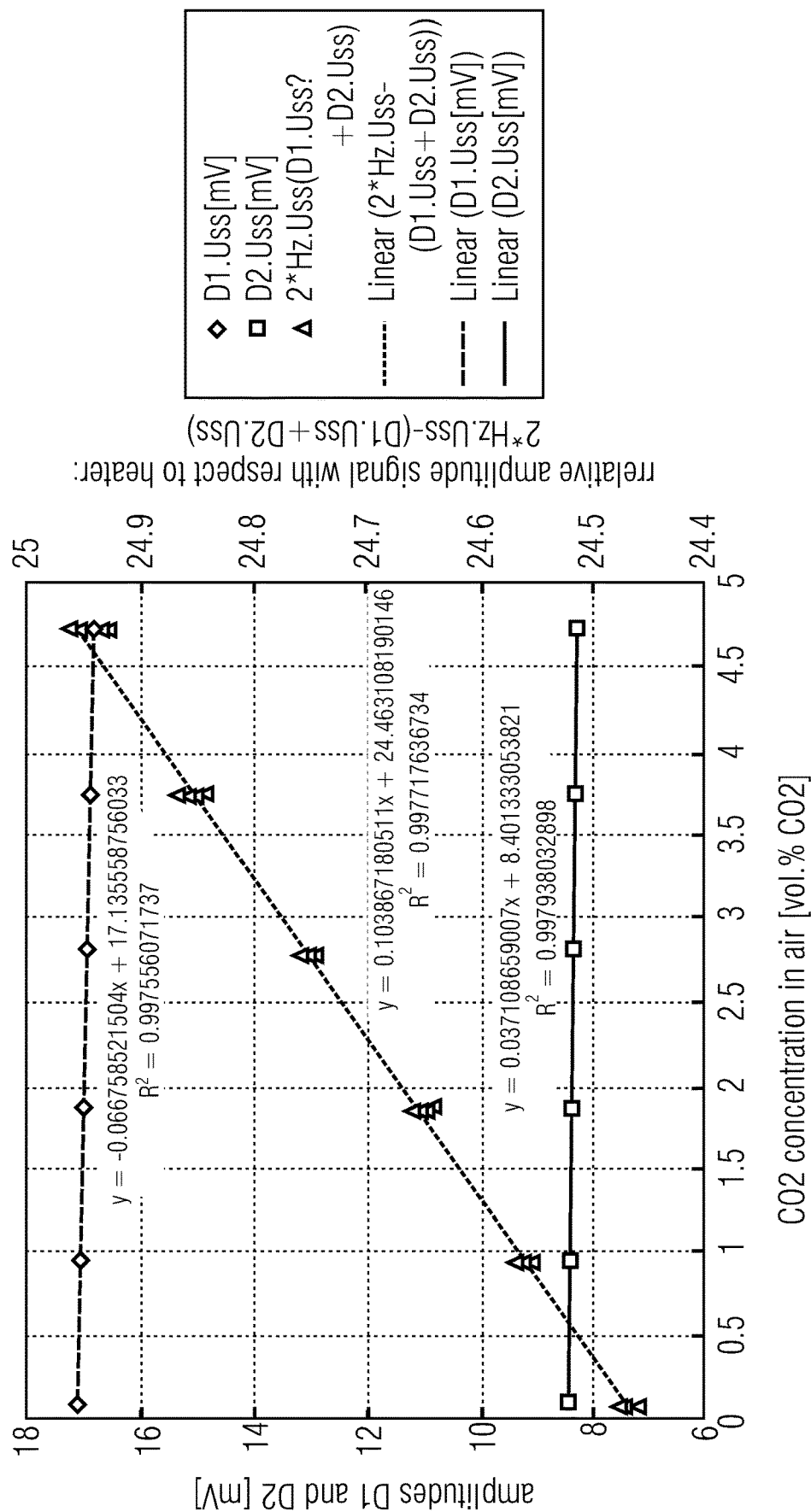
FIG. 15 shows a diagram of amplitudes of at least one sensor signal of a gas sensor according to an embodiment of the present invention.

FIG. 15 illustrates exemplarily measured amplitudes at the detectors D1 and D2 and a sum signal of the amplitudes formed relative to the heater amplitude, about the $CO_2$ dependence of the sensor. Here, for example, the amplitude D1.Uss (red) at the detector 1 and the amplitude D2.Uss (blue) at the detector 2 are illustrated. For example, at an increase of the $CO_2$ concentration, i.e. at an increase of the thermal diffusivity in the gas mixture, the two amplitude signals fall off. By forming a difference of the heater amplitude and the sum of the detector amplitudes, the relative amplitude signal sigUss=2*Hz.Uss−(D1.Uss+D2.Uss) (green, right y axis) will increase with an increase of the $CO_2$ content in the gas mixture, for example. According to an embodiment, FIG. 15 illustrates the amplitudes at the detectors for (0 ... 5) vol % of $CO_2$ in the air at a pressure of p=1010 mbar, a temperature of $T_{amp}$=24° C., and a heating power of P=(15±12.5) mW at a frequency of f=120 Hz.

1.3.1.2 Pressure Dependence

Figure 16:
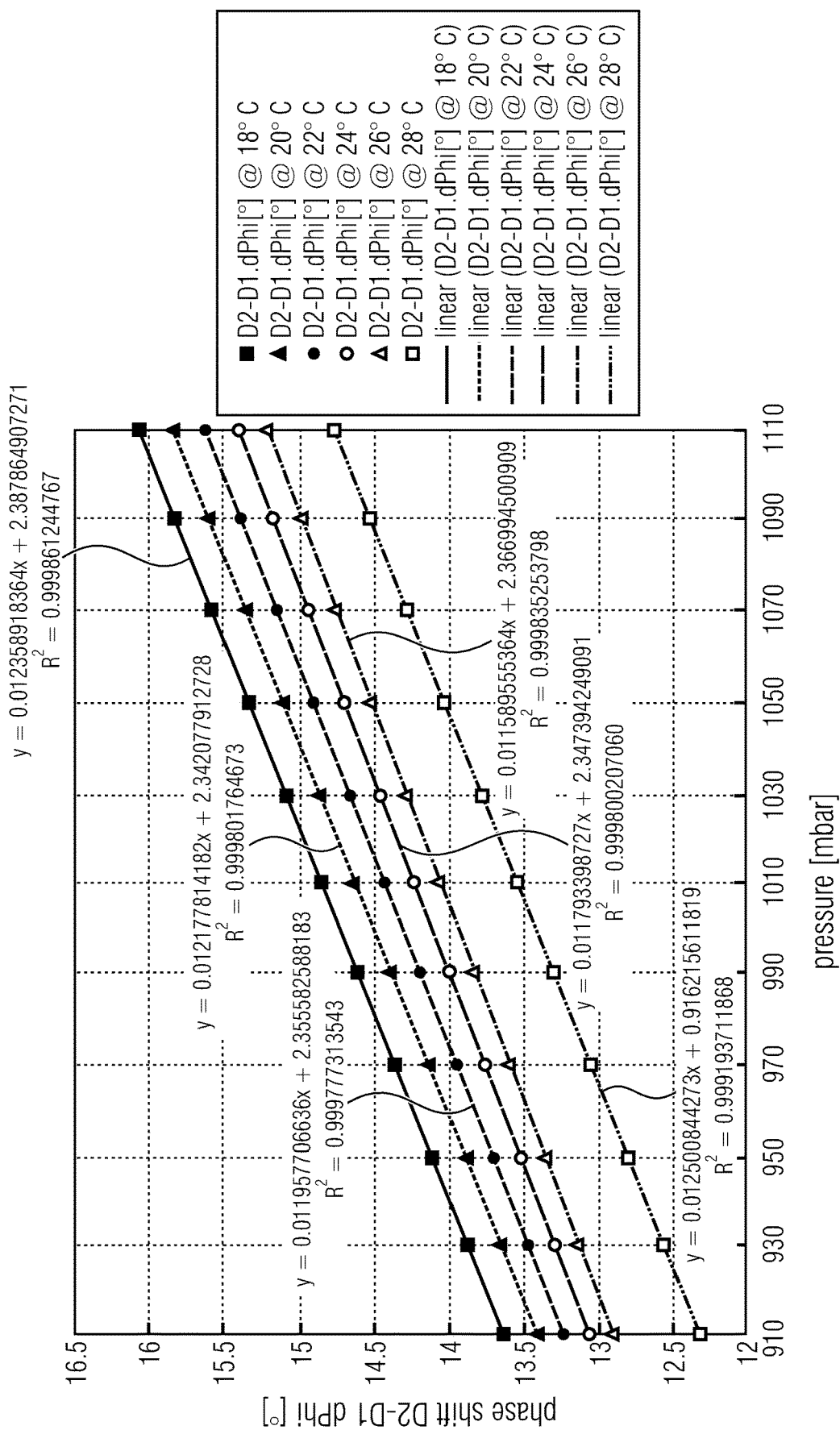
FIG. 16 shows a diagram of phase shifts between a first sensor signal and a second sensor signal of a gas sensor as a function of a pressure, according to an embodiment of the present invention.

A sensor signal may depend strongly on the pressure and the temperature. To correctly determine the gas properties, the cross-effects should therefore be known and corrected by the algorithms. For example, FIG. 16 illustrates the cross-sensitivity of the sensor signal in the air with respect to the absolute pressure and for different temperatures. What is exemplarily illustrated is the cross-sensitivity of a phase shift D2−D1 between the detectors D2−D1 (e.g. between the first thermal element structure D1 and the second thermal element structure D2) for the air with respect to a pressure p=(910 ... 1110) mbar across different temperatures $T_{amp}$=(18 ... 28)° C. in the air at a heating power of P=(15±12.5) mW with a frequency of f=120 Hz.

The pressure influence shows a linear relationship, the temperature influence shows a square relationship, as theoretically calculated. Both cross-sensitivities are in the order of magnitude of the signal for the gas concentration.

1.3.1.3 Heating Power and Frequency Dependence

Figure 17A:
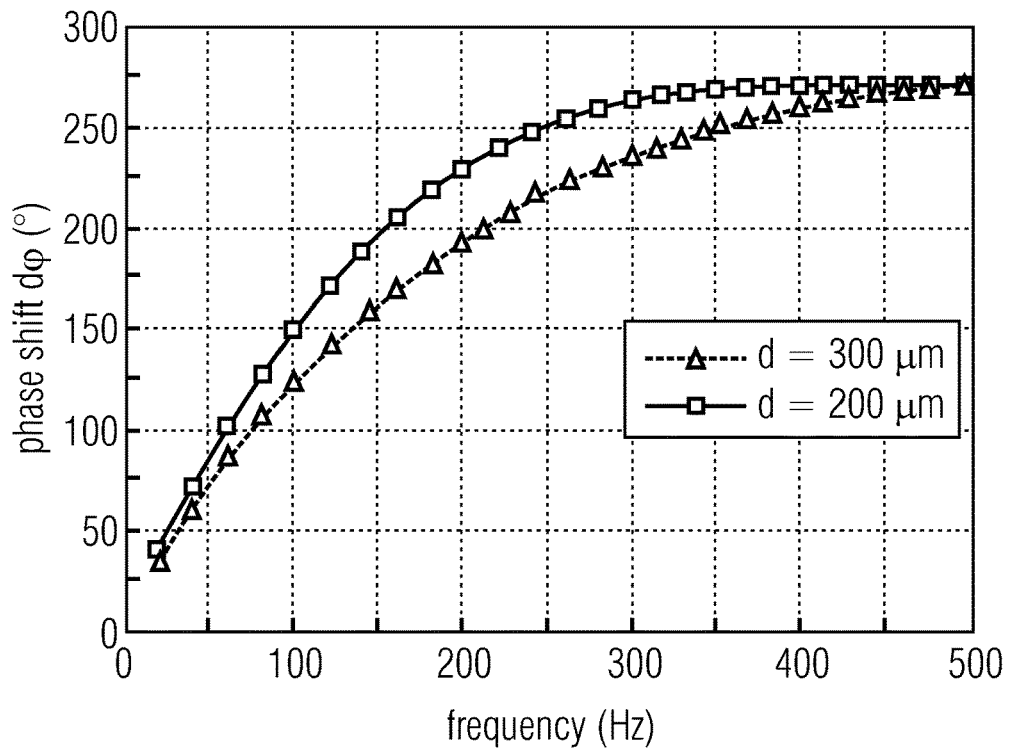
FIG. 17a shows a diagram of a phase shift of a sensor signal of a gas sensor as a function of a frequency, according to an embodiment of the present invention.

FIG. 17a shows an illustration of a sensor signal for a phase across the frequency in a measurement in $CO_2$. In other words, FIG. 17a shows a diagram of a phase shift in 100% $CO_2$ as a function of the frequency. The phase goes into saturation.

Figure 17B:
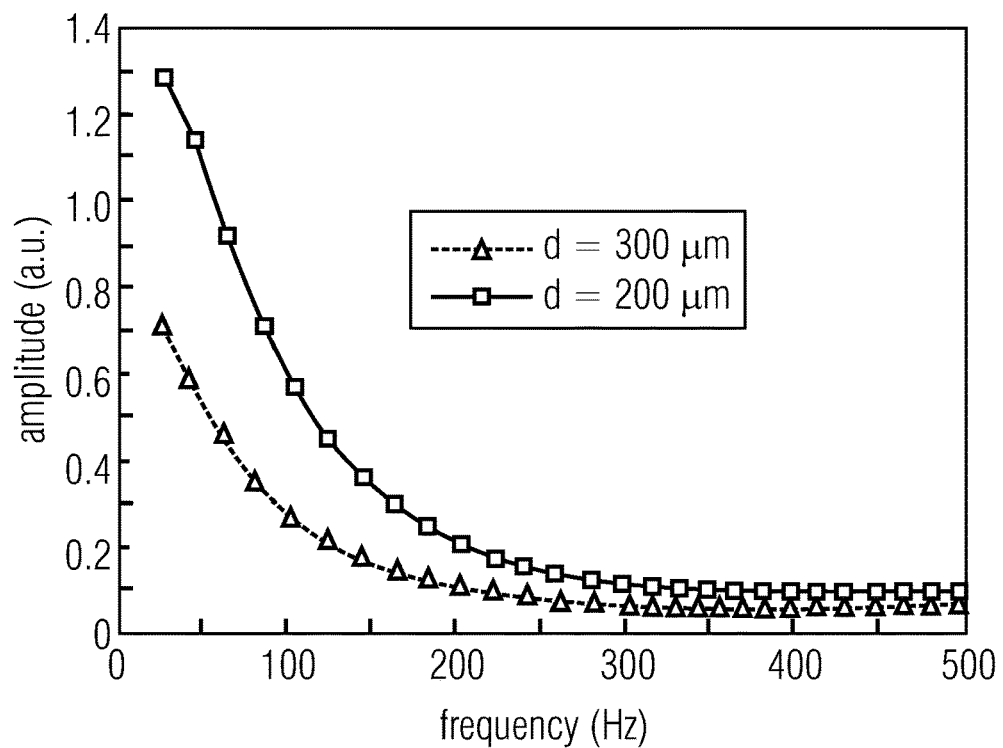
FIG. 17b shows a diagram of an amplitude of sensor signal of a gas sensor as a function of a frequency, according to an embodiment of the present invention.

FIG. 17b shows an illustration of a sensor signal for an amplitude across the frequency in a measurement in $CO_2$. In other words, FIG. 17b shows a diagram of the amplitude in 100% $CO_2$ as a function of the frequency. The amplitude decreases towards zero.

Compared to air, the heating power should be reduced in measurements in fuel gases so that the system does not exceed its A/D range. The heating power variation has shown that it makes sense in practice to operate the system with the largest possible sensor amplitude and to therefore obtain more stable signals, as compared to setting the heating power to a minimum, where the sample gas is less thermally influenced, but the signal-to-noise distance also decreases. The heating energy periodically introduced into the sensor has to be able to leave the sample volume within this period, for example, so that it does not heat up continuously. For example, a peak heating power of approximately 26 mW at 120 Hz was specified in three measurement systems.

The sensor behavior constitutes an ideal low pass filter of the 1st order, there are no overtone spectral components in the sensor signal. For this reason, actively sweeping through a frequency spectrum does not yield additional information. Thus, it was decided to operate the sensor at a fixed frequency, the effort with respect to electronics for this system could be reduced, the measuring time until a secured value is obtained is significantly shorter (all optional).

The higher the excitation frequency at the heater, the less energy may be transferred between the heater and the detector via the gas, since the thermal masses of the sensor itself limit the transfer speeds between the solid body and the gas. The amplitude decreases with increasing frequency up to a disappearing signal towards zero (cf. FIG. 17b), the phase shift saturates itself to a maximum (cf. FIG. 17a).

Forming an optimum of a phase resolution, a phase difference and an amplitude for different gas mixtures resulted in the best phase response at a frequency of, e.g., 120 Hz at a heating power of 26 mW for the micro sensor wire, and of 160 Hz at approximately 8 mW for the MEMS thermopile sensor on a thin-layer membrane (details optional).

1.3.1.4 Fuel Gas Mixtures

Figure 18:
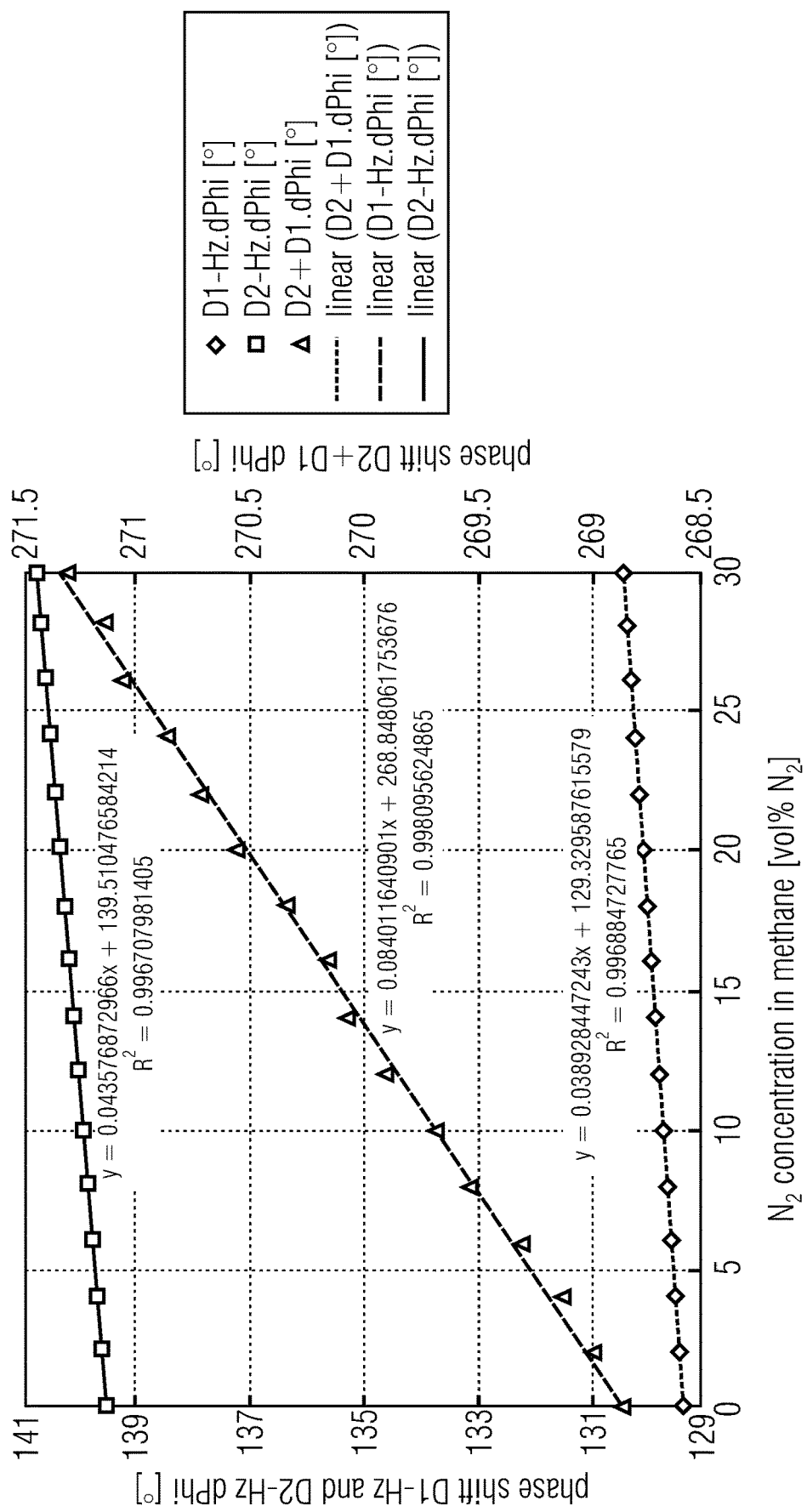
FIG. 18 shows a diagram of phase shifts of a first sensor signal, a second sensor signal, and a heater signal of a gas sensor as a function of a nitrogen concentration, according to an embodiment of the present invention.

Different gas compositions were examined at a measuring station. FIG. 18 shows a change of a phase signal of a sensor for methane with increasing addition of nitrogen as a nearly linear behavior. For example, what is illustrated is the phase signal as a function of the nitrogen concentration in methane as a phase difference D1-Hz.dPhi (red) between the heater and the detector 1, with a distance of 200 μm, a phase difference D2-Hz.dPhi (blue) between the heater and the detector 2, with a distance of 300 μm, and a phase difference D2-D1.dPhi (green, right y axis) between the detector 2 and the detector 1. Here, according to an embodiment, the phase shift between heater-detectors is illustrated for (0 . . . 30) vol % of $N_2$ in methane at a pressure of p=990 mbar, a temperature $T_{amp}$=21° C., and a heating power of P=(13±12.5) mW at a frequency of f=120 Hz in FIG. 18.

Figure 19:
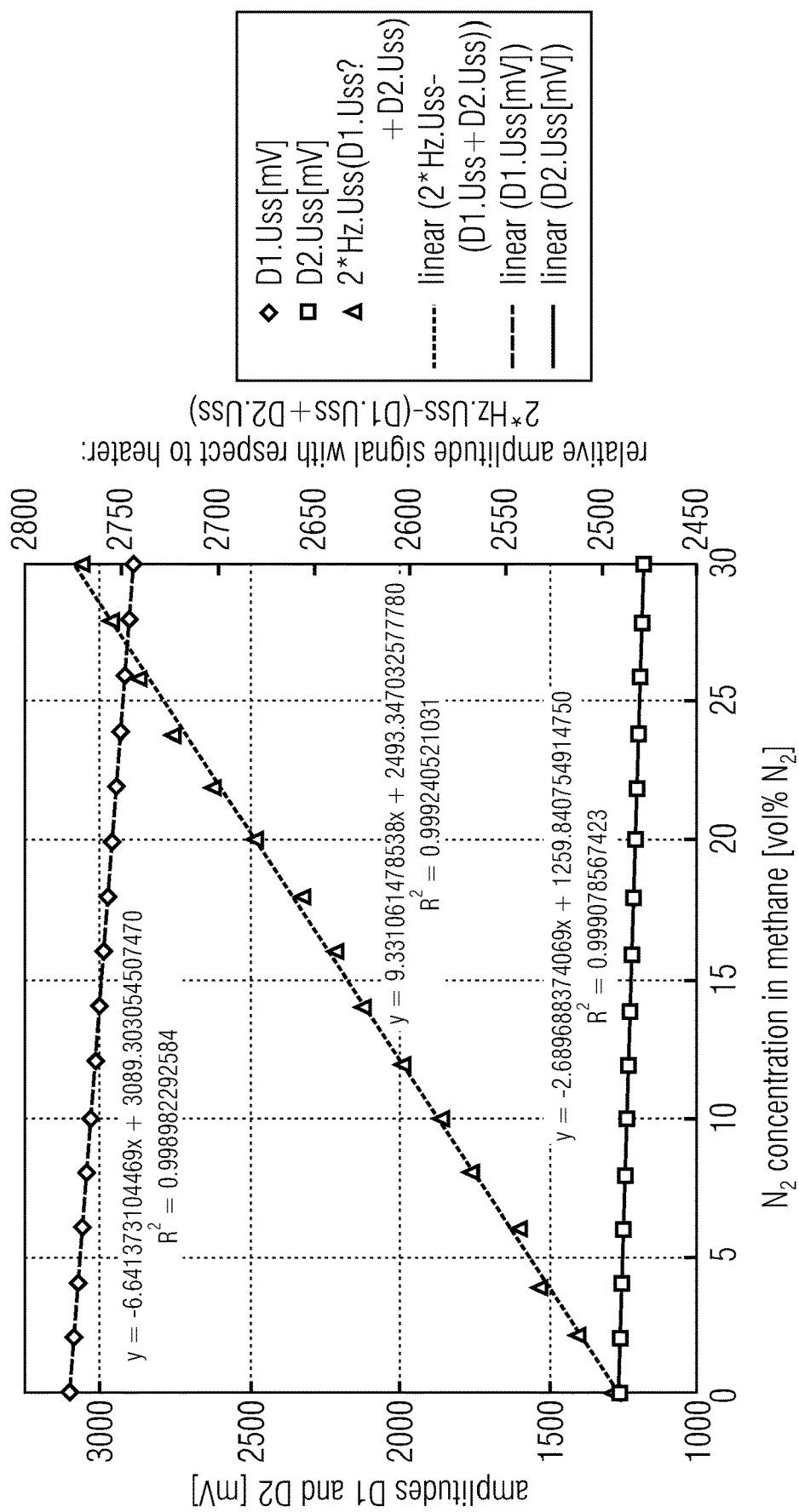
FIG. 19 shows a diagram of an amplitude of a first sensor signal and a second sensor signal of a gas sensor as a function of a nitrogen concentration, according to an embodiment of the present invention.

FIG. 19 shows a diagram of the amplitude D1.Uss (red) detected by means of the first detector, and the amplitude D2.Uss (blue) detected by means of the second detector. Here, according to an embodiment, the amplitudes of the detectors are illustrated for (0 . . . 30) vol % of $N_2$ in methane at a pressure of p=990 mbar, a temperature $T_{amp}$=21° C., and a heating power of P=(13±12.5) mW at a frequency of f=120 Hz in FIG. 19. Both amplitude signals D1.Uss and D2.Uss fall off with an increase of the $N_2$ concentration in methane, i.e. when decreasing the thermal diffusivity in the gas mixture, for example. By forming a difference of the heater amplitude and the sum of the detector amplitudes, the relative amplitude signal sigUss=2*Hz.Uss−(D1.Uss+D2.Uss) (green, right y axis) increases with an increase of the $N_2$ concentration, for example.

Figure 20:
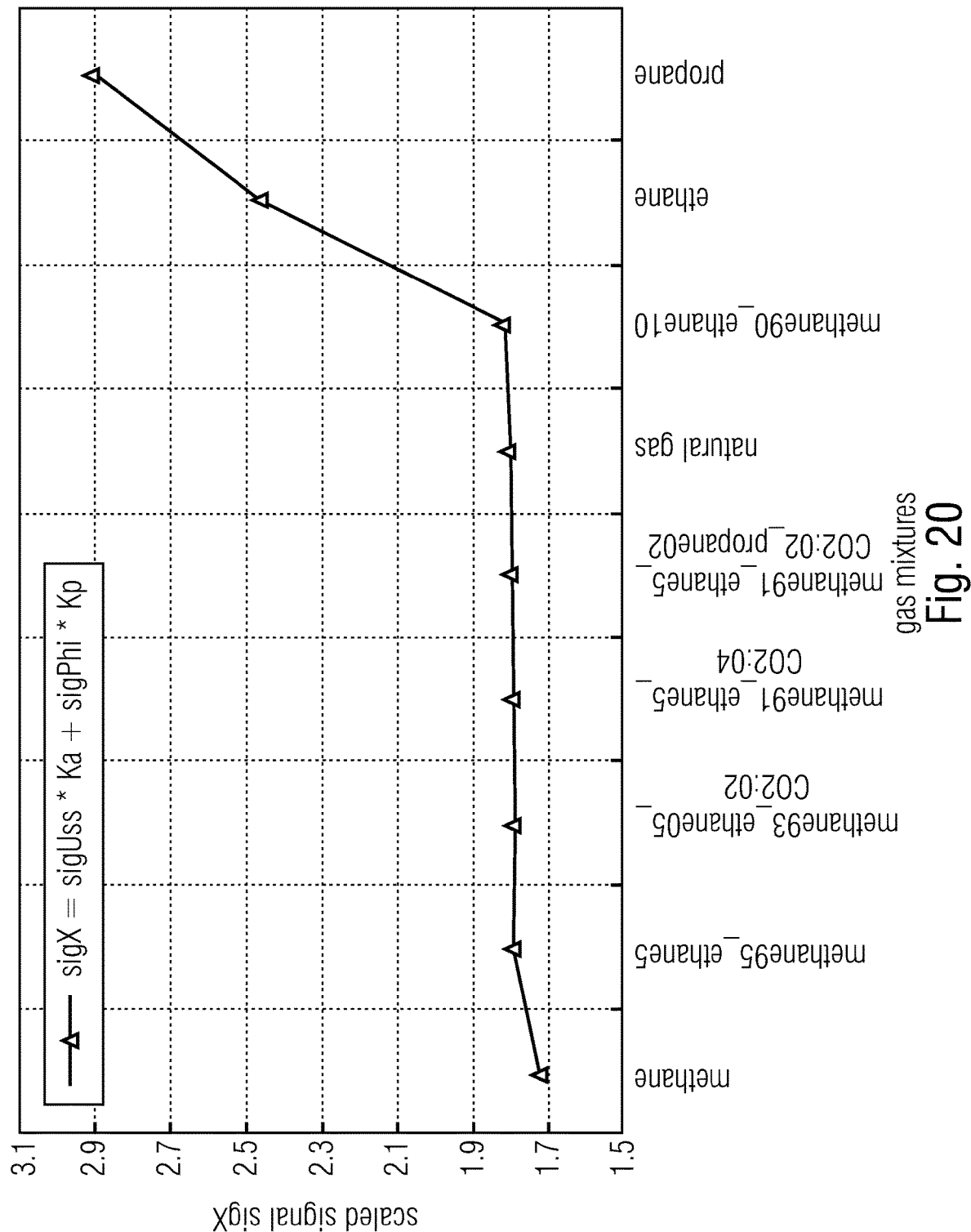
FIG. 20 shows a diagram of a combination signal of a gas sensor for different gas mixtures, according to an embodiment of the present invention.

FIG. 20 shows a diagram of a calculated sensor signal sigX (an example for a combination signal of the gas sensor) from a phase and an amplitude for different fuel gas mixtures. Thus, FIG. 20 shows the sensor signal (an example for a combination signal of the gas sensor) for different fuel gases and their mixtures: methane, ethane, and propane, as well as the mixtures: methane95-ethane05, methane93-ethane05-CO202, methane91-ethane05-CO204, methane91-ethane05-CO202-propane02, methane90-ethane10 and natural gas-L (the 2-digit numbers indicate the proportion of gas components in percent by volume). Methane, ethane and propane differ significantly from one another, but the methane mixtures also differ from one another with components of 2 vol % to 10 vol % of different gases. According to an embodiment, FIG. 20 illustrates the sensor signal for different fuel gases at a pressure of p=1001 mbar, a temperature $T_{amp}$=26° C., and a heating power of P=(13±12.5) mW at a frequency of f=120 Hz.

1.3.1.5 Findings from the Measurements in Gas Mixtures

The sensor signal shows strong pressure and temperature dependencies. In order to correctly determine the gas properties of a known mixture with a traceability to standard conditions and the comparison from tables, the cross-effects should therefore be known and corrected, for example. The pressure influence shows a linear relationship, the temperature influence shows a square relationship. Both cross-sensitivities are in the order of magnitude of the signal for the gas concentration.

1.3.2 Example: Method for the Calibration to a Gas Mixture with a Drift Correction with Respect to a Gas Pressure and a Gas Temperature (e.g. According to Aspect 2, Details Optional) for a Gas Sensor 1.3.2.1 Sum Signal of Phase and Amplitude (Example)

A combination of a phase/amplitude measurement has been shown to be a particularly stable sensor signal (combination signal). For example, both signals are weighted with the aid of separate constants and added and therefore combined to form a single sensor signal, for example:

$$sigX = sigUss * Ka + sigPhi * Kp \quad (6)$$

wherein sigX represents the calculated sum signal, sigUss represents the relative amplitude signal, and sigPhi represents the added phase signal of both detectors. The factors Ka and Kp are constants with which both partial signals are multiplied. For example, when converting the amplitude signal into mV, Ka=1/3500, and when converting the phase signal into degrees, for example, Kp=1/276 for $CO_2$ air mixtures up to 30 vol % of $CO_2$.

For example, the added phase signal sigPhi is formed from the sum of the two phase differences for the runtimes between the increasing edge of the heater impulse and the increasing edges at the detectors. For example, the following applies:

$$sigPhi = (D1\text{-}Hz).phi + (D2\text{-}Hz).phi \quad (7)$$

wherein (D1-Hz).phi and (D2-Hz).phi are to constitute the phase differences between the heater and the detectors.

As can be seen in FIG. 14, the phase difference between the heater and the detectors increases with increasing $CO_2$ concentration, i.e. with increasing thermal diffusivity, however, the two amplitudes at the detectors fall off with increasing thermal diffusivity (FIG. 15).

For example, the relative amplitude signal becomes increasing with an increase of the $CO_2$ content in the gas mixture due to a difference formation of the heater amplitude and the sum of the detector amplitudes:

$$sigUss = 2*Hz.Uss - (D1.Uss + D2.Uss) \quad (8)$$

For example, the signal sigX calculated from the phase and the amplitudes is in the range between (1.7 . . . 2.0) for (0 . . . 6) vol % of $CO_2$, for example. The device (e.g. the gas sensor) was measured in a temperature range between (16 . . . 28)° C. and in a barometric pressure field between (900 . . . 1200) mbar.

1.3.2.2 Drift Correction Via Polynomial Compensation (Details Optional)

When calibrating the sensor to a known gas mixture, the strong pressure and temperature dependence of the sensor signal should be compensated for in order to be able to infer a gas concentration from the measuring value.

Figure 21:
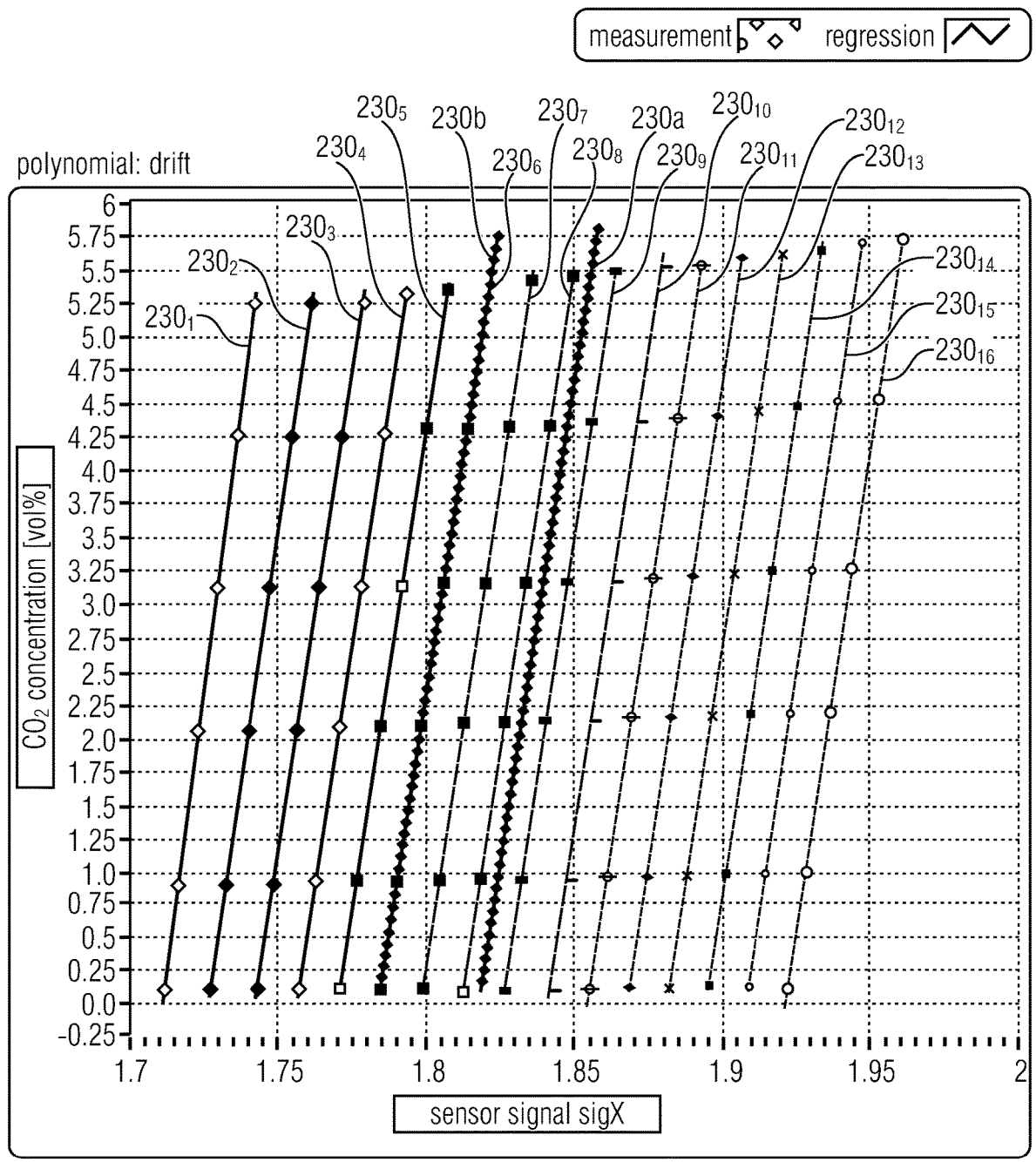
FIG. 21 shows a diagram of a combination signal of a gas sensor as a function of a $CO_2$ concentration, according to an embodiment of the present invention.

For example, this results in a 4-dimensional vector field (matrix) consisting of a gas concentration (CO2 [vol %]), the sensor signal sigX (the sum signal of the phase and amplitude), the pressure drift and the temperature drift. It is noticeable that the individual graphs in the diagram of FIG. 21 showing the dependence between the gas concentration and the temperature signal, which each stand for a constant ambient pressure or a constant temperature, are shifted in parallel to each other. If a graph is now formed from all the parallel shifted characteristic curves, a normalized relationship of the signal is obtained for a mean temperature and a mean pressure (cf. red line 230a in FIG. 21).

FIG. 21 shows the matrix of the measuring data of a variation of a gas concentration of (0 . . . 5) vol % of $CO_2$ in nitrogen in a pressure range of (900 . . . 1200) mbar, and in a temperature range of (16 . . . 28)° C. With the aid of a pressure-dependent polynomial function, the green line 230b of the calibration curve can be shifted towards a current operating pressure. The red line 230a corresponds to the mean of all blue lines $230_1$ to $230_{16}$, and is a characteristic curve of the sensor signal for the gas concentration normalized to a mean temperature and a mean pressure.

When plotting the characteristic curves of the sensor signal sigX from the measured variation are applied for each temperature and a mean gas concentration across the pressure (cf. FIG. 22), a set of curves of straight lines shifted in parallel to each other is obtained as well. Higher pressures and a cold gas, i.e. gas molecules that are closer to each other, lead to a higher sensor signal, low pressures and a warm gas results in a low signal sigX.

Figure 22:
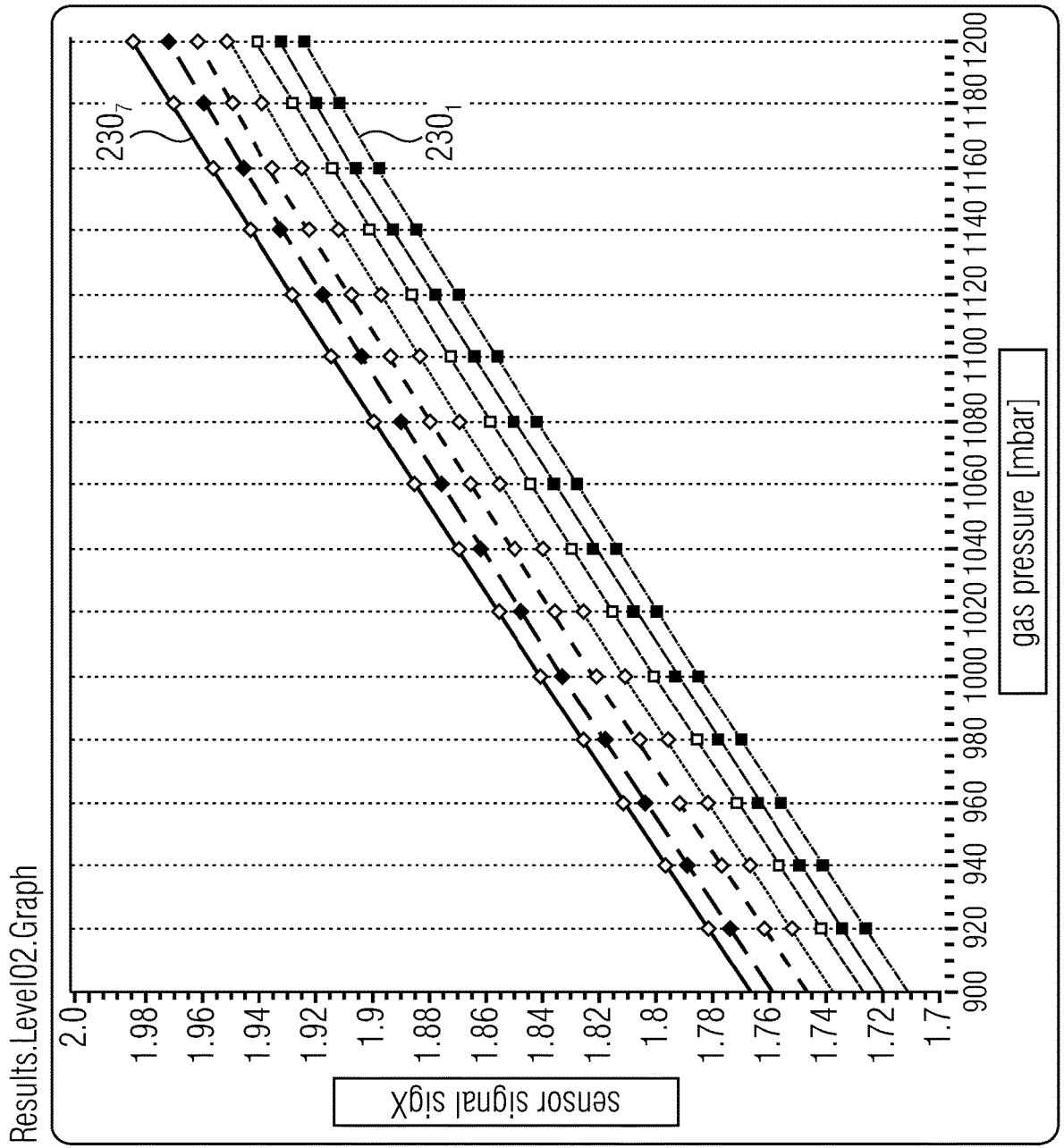
FIG. 22 shows a diagram of a combination signal of a gas sensor as a function of a pressure, according to an embodiment of the present invention.

Thus, FIG. 22 shows a pressure dependence of the sensor signal sigX for a mean fixed gas concentration, a set of curves of different temperatures. The lowest line $230_1$ describes the relationship at the highest temperature of 28° C. in the variation, and the highest line $230_7$ illustrates the pressure dependence of the signal at 16° C.

Figure 23:
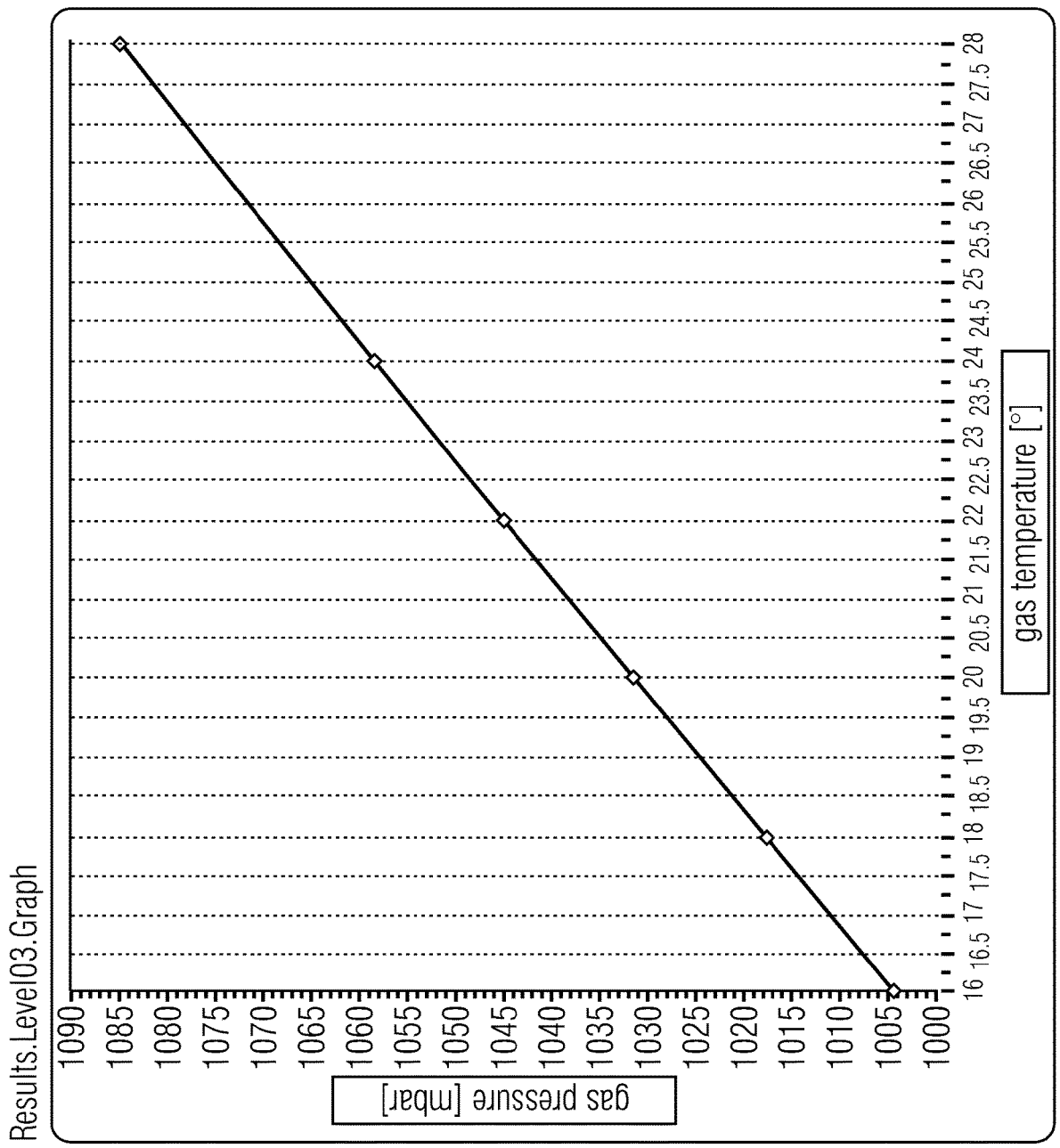
FIG. 23 shows a diagram of a relationship between a gas pressure and a gas temperature for a gas sensor according to an embodiment of the present invention.

If a horizontal line is placed into the parallel set of lines in FIG. 22 for a fixed mean sensor signal, wherein said horizontal line intersects all lines of the set of curves, the relationship between gas pressure and gas temperature of FIG. 23 is obtained.

FIG. 23 shows a slightly square relationship between a gas pressure and a gas temperature (for a mean gas concentration and a mean sensor signal sigX).

1.3.2.3 Determination of a Regression Constant (Details Optional)

When calibrating the gas sensor to a specific gas mixture, regressions are formed from the variation matrix in succession through the above-described relationships. Regression level A describes the relationship between the gas concentration of the calibration reference and the sensor signal sigX. The individual curve per pressure and temperature are each approximated in a square regression according to the form: $y = A.c0 + A.c1*sigX + A.c2*sigX^2$. Since the increase of all curves is approximately constant and the square coefficient c2 goes towards zero, the mean value is formed from all values for the coefficients A.c0, A.c1 and A.c2, the central characteristic curve 230a illustrated in red in FIG. 21 is obtained across the entire measuring value variation $230_1$ to $230_{16}$. This has to be shifted on the x axis according to the drift influence of the pressure. Due to the pressure-dependent $sigX_0 = f(p)$, the associated offset A.c0 is sought, which is inserted into the equation of the regression plane A.

The regression plane B describes the pressure drift of the sensor signal sigX. The offset A.c0 is again calculated as a function of the pressure drift: $A.c0 = sigX.y_0 - B.c1*pressure.x_0 - B.c2*pressure.x_0^2$. If $sigX.y_0 = 0$, the equation is simplified to: $A.c0 = -(B.c1*pressure.x_0 + B.c2*pressure.x_0^2)$. The (now) pressure-dependent polynomial coefficient $A.c0 = f(p)$ is replaced in the regression equation of the plane A (substituted), for example.

For example, the determined pressure-dependent offset for the polynomial of the regression plane A is calculated from the cosine relationship of the angle relationship between the offset and the increase with: $A.c1 = A.c0/sigX_0$; $sigX_0 = f(p)$ and $A.c0 = (-1)*sigX*A.c1$. With polynomials of a higher order, the 1st derivative of the curve should be formed, and the slope in the reference point should be calculated therefrom.

TABLE 1 polynomial coefficients of the three regression planes (examples)

| Regressions plane | | Polynomial coefficients | | | Coefficient of determination | Reference to the previous plane (center of the variation range) |
|---|---|---|---|---|---|---|
| | | c0 | c1 | c2 | | |
| A | Signal-to-CO2 | −266.153759 | 144.315423 | 0 | 0.999258 | 0 |
| B | Pressure to signal shift | 0.94394 | 0.001017 | −1.50E−07 | 0.999929 | 1.843335 |
| C | Temperature-to-pressure shift | 884.519093 | 7.844777 | −0.023415 | 0.9983 | 1050 |

TABLE 1-continued polynomial coefficients of the three regression planes (examples)

| Regressions plane | Polynomial coefficients | | | Coefficient of determination | Reference to the previous plane (center of the variation range) |
|---|---|---|---|---|---|
| | c0 | c1 | c2 | | |

1.3.2.4 Converting the Signal to a CO2 Value (Example: Details Optional)

For example, the value for the gas concentration calculated from the polynomial of the regression plane A is corrected by the pressure and temperature drift:

$$CO_2[vol\ \%] = A.y(sigX) \cdot \left(1 - \left[\frac{B.y(p) - B.ref}{sigX - B.ref}\right] \cdot \left(1 - \left[\frac{C.y(T) - C.ref}{p - C.ref}\right]\right)\right) \quad (9)$$

wherein A.y(sigX), B.y(p) and C.y(T) correspond to the respective full polynomials for the measuring signal, the gas pressure, and the gas temperature.

If the fixed references constituting the geometric center of the variation range are inserted into the equation, and the polynomials are resolved accordingly, the following equation results. With B.ref=B.y(c.ref), the following applies:

$$CO_2[vol\ \%] = Ay.(sigX) \cdot \left(1 - \left[\frac{B.c1 \cdot (p - C.ref) + B.c2 \cdot (p^2 - C.ref^2)}{sigX - B.y(C.ref)}\right]\right) \cdot \left(1 - \left[\frac{C.y(T) - C.ref}{p - C.ref}\right]\right) \quad (10)$$

If C.ref=1050 mbar is inserted, the following applies:

$$CO_2[vol\ \%] = A.y(sigX) \cdot \left(1 - \left[\frac{B.c1 \cdot (p - 1050) + B.c2 \cdot (p^2 - 1050^2)}{sigX - B.y(1050)}\right]\right) \cdot \left(1 - \left[\frac{C.y(T) - 1050}{p - 1050}\right]\right) \quad (11)$$

Figure 24:
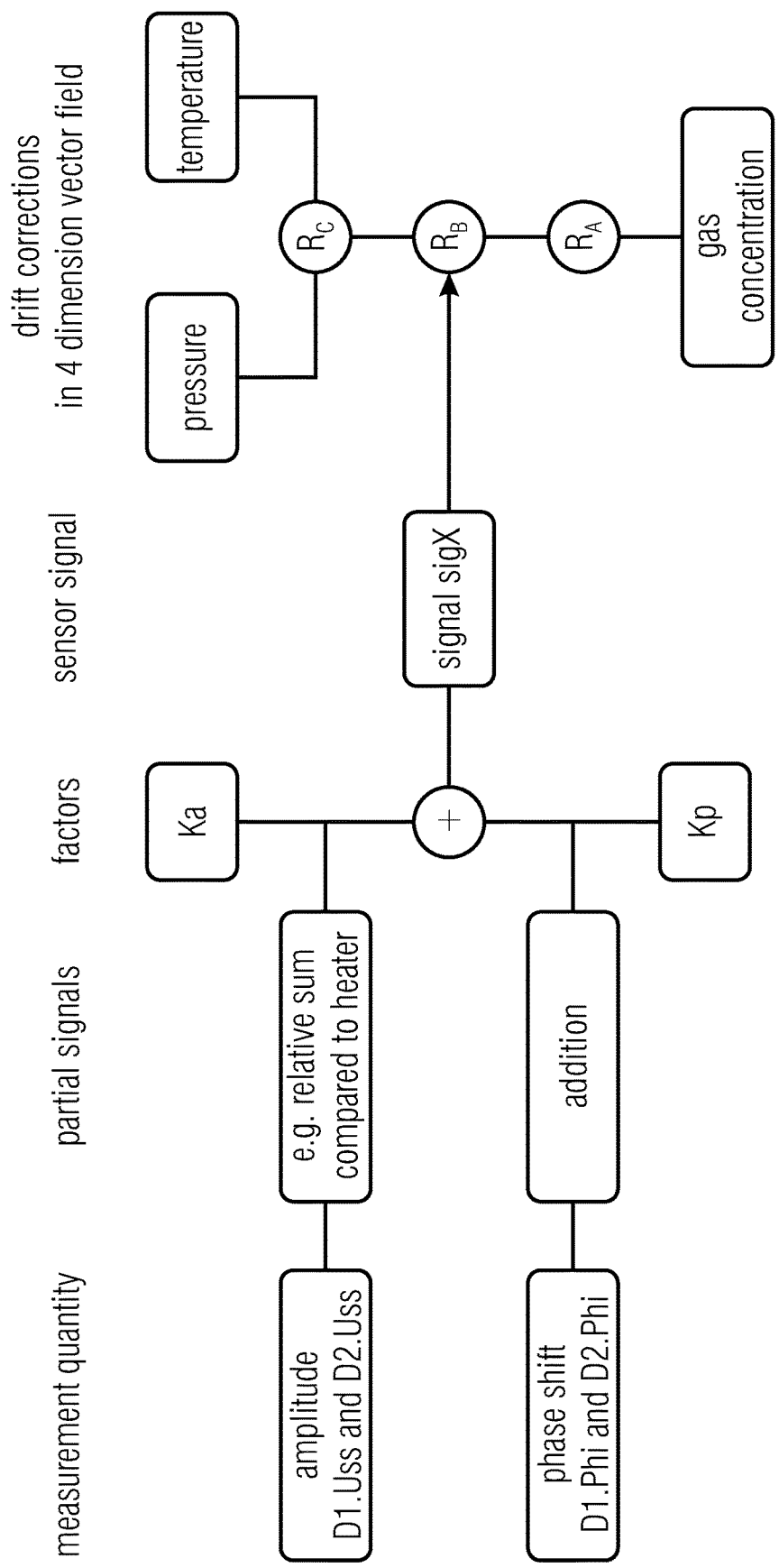
FIG. 24 shows a block diagram of a method for generating a combination signal of a gas sensor according to an embodiment of the present invention.

FIG. 24 shows a block diagram of a schematic process for determining a gas concentration under consideration of the influences of the pressure and the temperature from the formed sensor signal sigX. In other words, FIG. 24 shows a schematic illustration for forming the sensor signal sigX from amplitudes and phases as well as the determination of a gas concentration from sigX under the consideration of a pressure and temperature influence (example).

Figure 25:
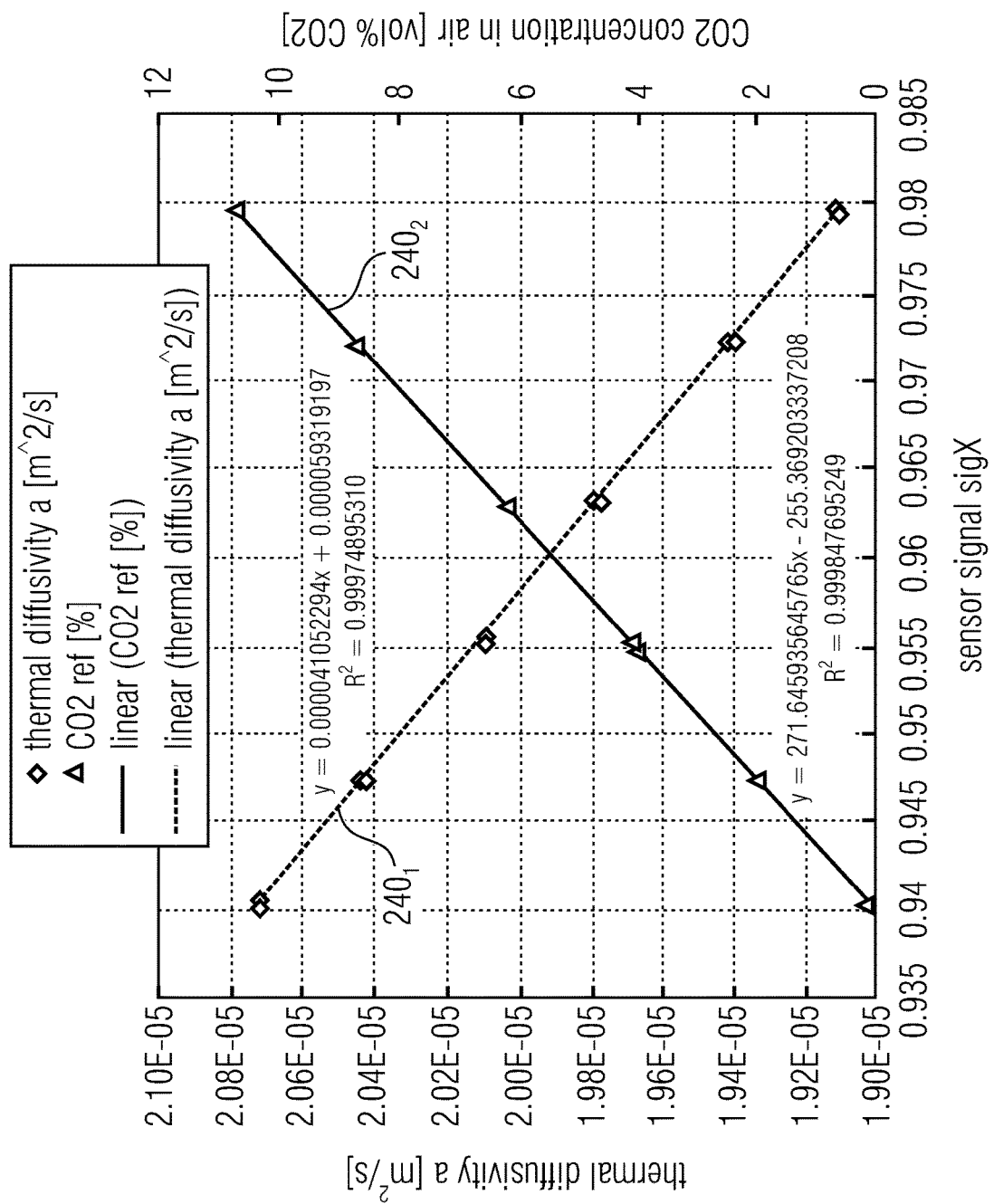
FIG. 25 shows a diagram of a thermal diffusivity as a function of a combination signal of a sensor according to an embodiment of the present invention.

Besides the calibration of the sensor signal to the concentration of a known gas mixture, it is also possible to directly determine the thermal diffusivity a of the gas mixture. In FIG. 25, the theoretically calculated thermal diffusivity is plotted with respect to the sensor signal sigX. In other words, FIG. 25 shows the thermal diffusivity with respect to the sensor signal sigX at a constant pressure and a constant temperature in a mixture of carbon dioxide $CO_2$ in nitrogen $N_2$. The thermal diffusivity 240$_1$ (red line) falls with an increase of the $CO_2$ concentration 240$_2$ (green line).

Thus, a design and an evaluation of a thermal gas sensor for measuring physical gas properties is described herein. With this invention, the following is proposed (aspects are independent from each other and can be used in combination):

sensor design based on two technology variations: a MEMS wire sensor on a SOI substrate, and a thermopile sensor on a thin-layer membrane operation of the gas sensor: signal generation and signal evaluation on an embedded system evaluation algorithm for calibrating a gas mixture with a drift correction with respect to a gas pressure and gas temperature

1.4 Market—Possible Application Areas (Optional)

In medical technology for respiration

In natural gas analysis—determination of the calorific value

There are various systems for patient ventilation on the market today. These are distinguished according to their use in the clinical and home care sector (e.g. systems from Heinen+Löwenstein, Dräger and Stephan Medizintechnik). The systems of these suppliers contain only in their top versions all the measuring equipment for determining pressure, respiratory flow, and respiratory gas analysis. To this end, several devices have to be combined, which mainly measure remotely from the patient. From this, it may be derived that a cost-efficient measurement of a respiratory flow and $CO_2$ content close to the patient has not yet been implemented, and that the innovative content of the project is therefore confirmed with the development of a multi-sensor system with hybrid filters.

In our opinion, the successful development of the new MEMS-based gas measurement system represents a significant advance for the sensor technology and respiratory care. The integration of both sensors ($CO_2$ and flow) in one sensor system leads to a significant reduction of the installation space and the system weight (an essential criterion for intubated patients). Only the measuring point close to the patient, directly on the mask or tube—as close as possible to the airways—enables a sufficiently accurate measurement to avoid influences from tubes, movements or sources of interference. In addition, the thermal measurement principle is expected to provide more accurate flow measurements and a rapid gas analysis.

Figure 26:
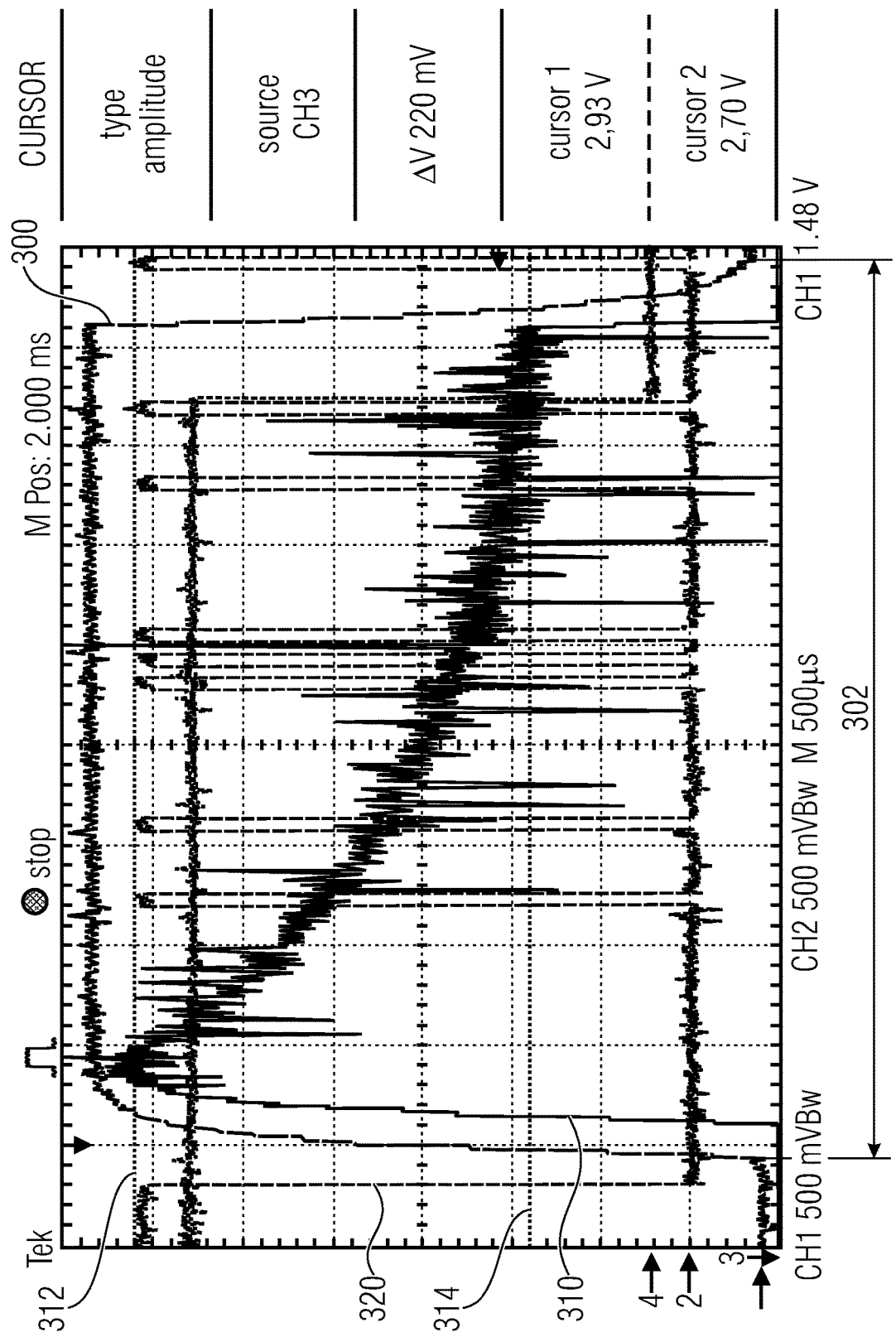
FIG. 26 shows a diagram of a current flow in a heater during a heating period for a first gas mixture according to an embodiment of the present invention.
Figure 27:
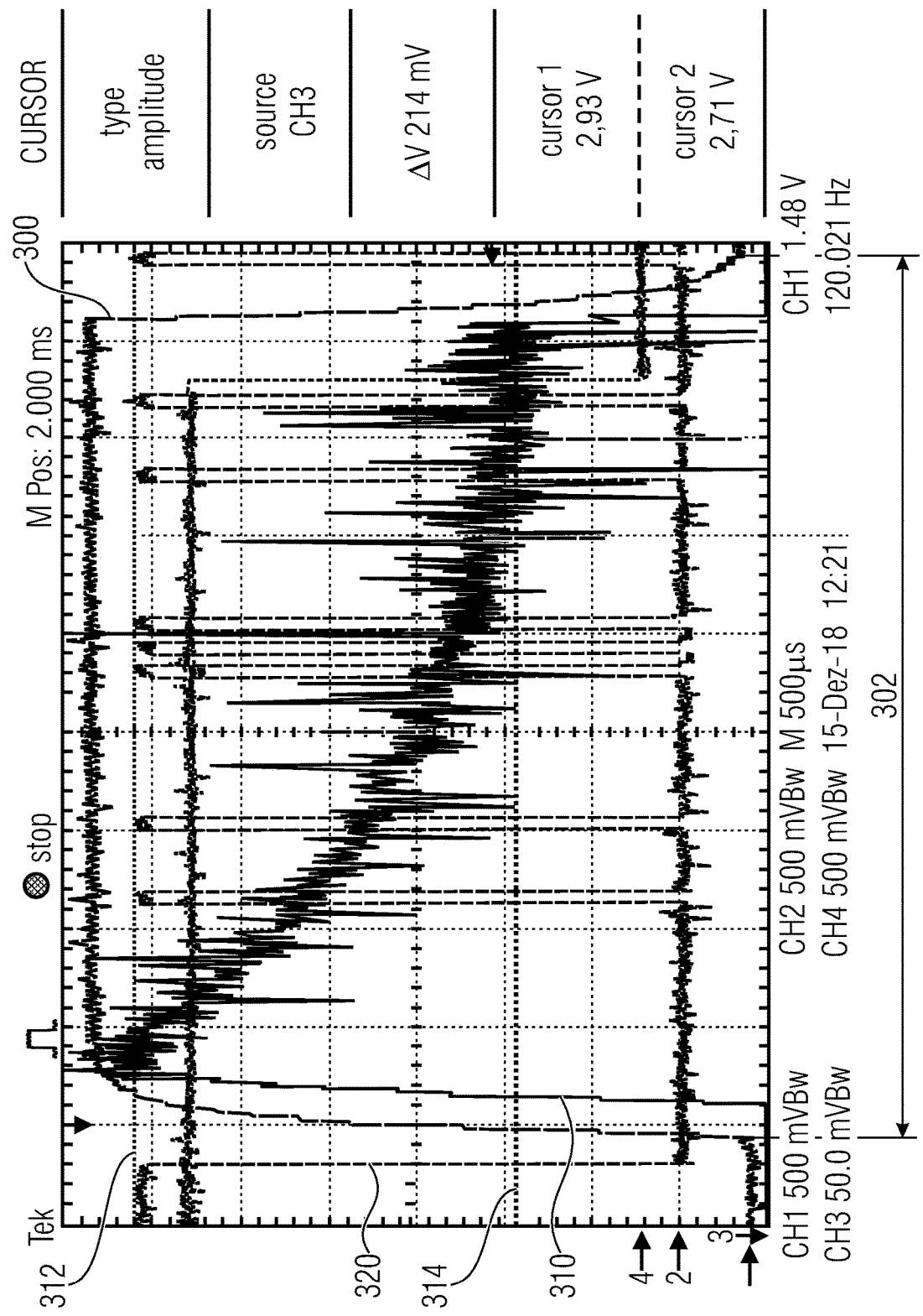
FIG. 27 shows a diagram of a current flow in a heater during a heating period for second gas mixture according to an embodiment of the present invention.
Figure 28:
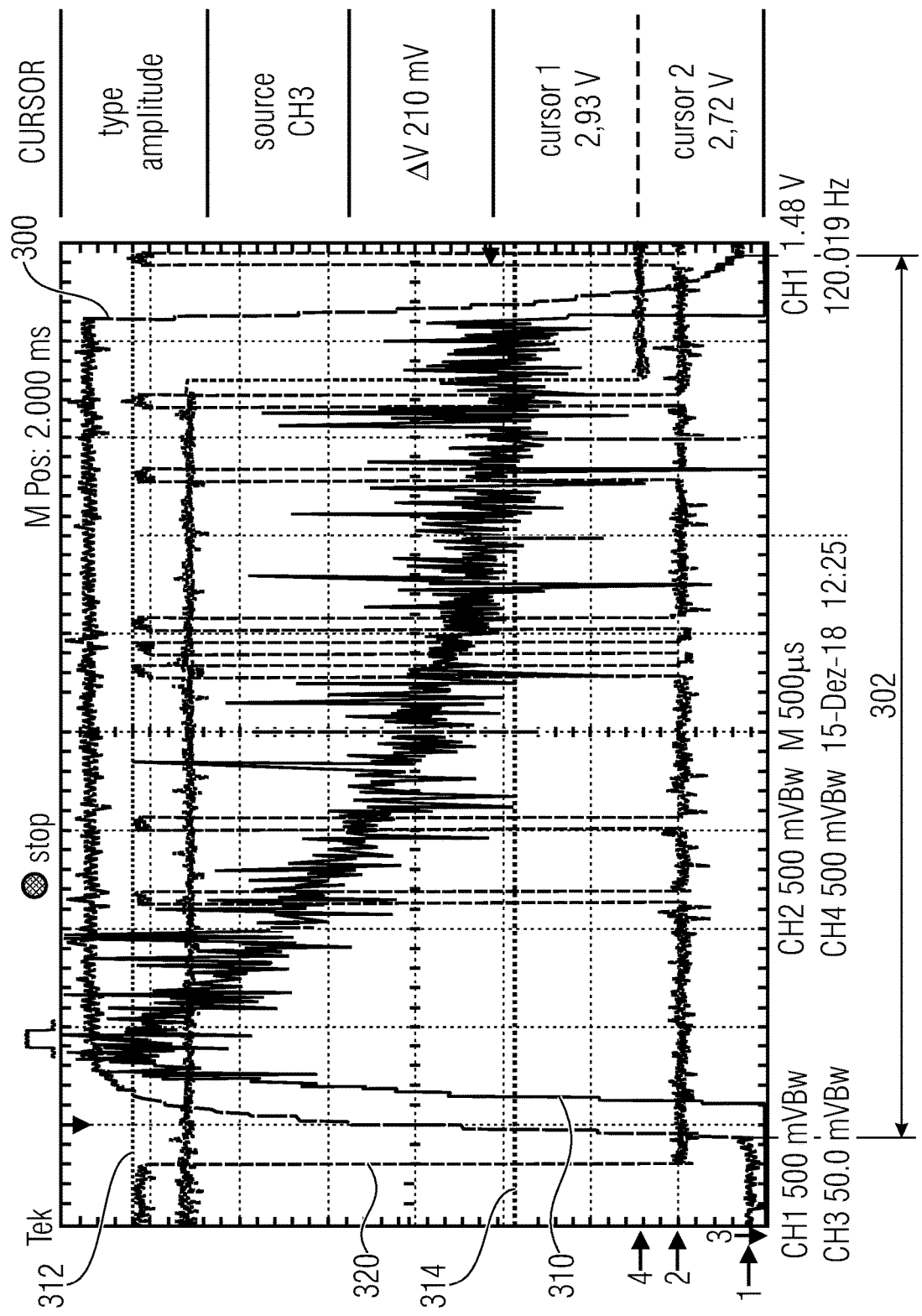
FIG. 28 shows a diagram of a current flow in a heater during a heating period for a third gas mixture according to an embodiment of the present invention.

FIG. 26, FIG. 27 and FIG. 28 show a diagram that illustrates a heating voltage 300 applied to a heater of a gas sensor, a current flow 310 during a heating period 302, measuring times 320 for an optional ADC (analog-digital converter) of an inventive evaluation arrangement, and a comparator signal for a detector (e.g. for a first detector or for a second detector). For example, the inventive evaluation arrangement is configured to obtain the information as to how much heat is dissipated by the heater during the heating period 302 on the basis of a measurement of the current flow

310 through the heater at a specified heating voltage 300. According to an embodiment, the evaluation arrangement is configured to obtain the current flow 310 shortly after switching on the specified heating voltage 300 and shortly after switching off the specified heating voltage. For example, this means that a start peak 312 of the heating current 310 and a heating current end value 314 of the current flow 310 may be processed by the evaluation arrangement.

According to an embodiment, the start peak 312 has the same value for the same gas sensor (there may possibly be small variations of less than 1%, 0.5%, or 0.1%). According to the embodiments illustrated in FIGS. 26 to 28, the start peak 312 is at 2.93V and approximately 400 µs after the switch-on. This value of the start peak 312 is illustrated for a gas sensor in the FIGS. 26 to 28. For another gas sensors, the value of the start peak 312 may deviate from the value illustrated in FIGS. 26 to 28. Here, it is to be noted that the value of the start peak 312 may not only deviate between different gas sensors, but also between gas sensors that are identical in construction.

The heater heats up during the heating period 302, as a result of which a heater resistance increases according to a positive TCR (temperature coefficient) and the heater reaches an end temperature in the switch-off moment ($I_{hz}$=U/$R_{Hz}$→$I_{hz}$≈1/$R_{Hz}$). The smaller the heating current end value 314, the hotter the heater, the smaller the amount of heat dissipated to a gas to be analyzed surrounding the heater and the smaller the thermal conductivity of the gas or gas mixture.

In the embodiment according to FIGS. 26 to 28, a gas or gas mixture is analyzed by an inventive gas sensor and/or an inventive evaluation arrangement. Here, a gas mixture with 10% of $CO_2$ and 90% of $N_2$ (nitrogen) is analyzed according to the embodiment of FIG. 26, the gas nitrogen (100% of $N_2$) is analyzed according to the embodiment of FIG. 27, and the gas oxygen (100% of $O_2$) is analyzed according to the embodiment of FIG. 28. For example, these components comprise different thermal conductivities, e.g. oxygen with a thermal conductivity λ of 0.0263 W/(m*K), nitrogen with a thermal conductivity λ of 0.0260 W/(m*K) and $CO_2$ with a thermal conductivity λ of 0.0168 W/(m*K).

According to the embodiment of FIG. 26, the heating current end value 314 reaches 2.7 V, as a result of which a difference of 220 mV (deltaU=220 mV) is reached between the switch-on current (start peak 312) and switch-off current heating current end value 314. According to the embodiment of FIG. 27, the heating current end value 314 reaches 2.71V, as a result of which a difference of 214 mV (deltaU=220 mV) is reached between the switch-on current (start peak 312) and the switch-off current (heating current end value 314). According to the embodiment of FIG. 28, the heating current end value 314 reaches 2.72V, as a result of which a difference of 210 mV (deltaU=220 mV) is reached between the switch-on current (start peak 312) and switch-off current (heating current end value 314). In other words, the evaluation arrangement processes (examines) the difference of the heating current (the current flow 310) between the switch-on instant and the switch-off instant, i.e. between the cold heater and the hot heater.

Compared to the embodiments of FIG. 27 and FIG. 28, the $CO_2$ mixture of FIG. 26 comprises the highest heater temperature, as a result of which the lowest heating current is reached here (e.g. the lowest heating current end value 314) since $CO_2$ has only half of the thermal conductivity compared to $N_2$ and $O_2$. Compared to this, in 100 vol. % of $N_2$, the heater according to FIG. 27 does not reach the end temperature (e.g. the heating current end value 314) as in the 10% of $CO_2$—90% of $N_2$ mixture of FIG. 26. Similarly, in 100 vol. % of 02, the heater according to FIG. 28 does not reach the end temperature (e.g. the heating current end value 314) as in the 10% of $CO_2$—90% of $N_2$ mixture of FIG. 26. In FIG. 28, with 210 mV, the difference between the switch-on current and the switch-off current is the lowest, and the gas analyzed here accordingly has the highest thermal conductivity compared to the 10% of $CO_2$—90% of $N_2$ mixture (cf. FIG. 26) and the 100 vol. % of $N_2$ (cf. FIG. 27).

According to an embodiment, the measurement effect is at a minimum, since the inventive heater is highly doped, e.g., in order to be able to heat with 3 V, for example. In addition, the TCR (temperature coefficient) of the heater may be low (e.g. ≤6*$10^{-3}$ 1/K, ≤4.1*$10^{-3}$ 1/K, ≤3.9*$10^{-3}$ 1/K).

Thus, with the present gas sensor and/or the present evaluation arrangement, e.g., a sensor signal (e.g. the current flow 310) is used to be able to distinguish the concentration of a third gas. In emergency ventilation, an increased oxygen concentration is used. It is common to use a mixture of 50 vol. % of $O_2$ in $N_2$. Without correcting the sensor signal at a higher oxygen concentration with respect to the fresh gas when calibrating, the gas sensor (e.g. a $CO_2$ sensor, such as the inventive gas sensor, for example) shows a concentration of −5% of $CO_2$ at 50 vol. % of $O_2$ in the $N_2$—$O_2$ gas mixture, for example. That is, the change of the third gas component in the mixture, a change of concentration of oxygen, leads under certain circumstances to an error signal in the $CO_2$ sensor. Similarly, a concentration mixture of approximately 56% of oxygen and 5% of $CO_2$ in nitrogen $N_2$ shows at the sensor, e.g., a $CO_2$ concentration of 0 vol. %, as is the case in the fresh gas calibration with 21 vol. % of $O_2$ and approximately 78 vol. % of $N_2$.

If there is no technical possibility to indicate to the sensor the oxygen concentration of the inhalation gas such that a concentration display of the inventive gas sensor could be corrected accordingly, the sensor would indicate incorrect values, for example.

As can be seen in FIGS. 26 to 28, information about the thermal conductivity is located in the end temperature that the heater reaches up to its switch-off. When comparing the temperature difference (deltaU) between the current peak 312 at the beginning of the heating and the end value 314 shortly before switching off, different thermal conductivities in the gas mixture could be derived at a different deltaU.

According to an embodiment, the heater is operated with a constant voltage (corresponding, according to FIGS. 26 to 28, to a value of 3000 digits at a D/A output, which is only an example and may be selected freely). For example, with the current measurement via a shunt resistor and a current shunt monitor, e.g. the INA199A, component U402 as is the case in FIG. 10, e.g., a voltage signal acting proportional to the heating current is obtained. FIGS. 26 to 28 illustrate screen shots of the signals recorded at the oscilloscope, wherein the heater current path (the current flow 310) is greatly magnified (the noise may be reduced by shielding the measurement lines). For example, a product of the heating voltage 300 and the measured heating current 310 enables a statement about the heating power. The heating current 310 decreases over time since the heater heats up and increases its interior resistance due to its temperature gradient of the resistance (TCR). Due to the higher interior resistance, less current may flow at the same heating voltage ($I_{Hz}$≈1/$R_{Hz}$).

The amount of energy that the heater may dissipate into its surrounding gas depends, among other things, on the thermal conductivity of the gas. For example, at 10% of $CO_2$ in $N_2$, the heater is not able to dissipate a great amount of heat since $CO_2$ has a thermal conductivity of $\lambda=0.0168$ W/(m*K), the heater therefore reaches a higher end temperature before the switch-off in contrast to 100% $N_2$ gas. In the measurement, a difference of deltaU=220 mV has been determined. Nitrogen $N_2$ has a thermal conductivity of $\lambda=0.0260$ W/(m*K), the heater could dissipate twice the amount of heat compared to a gas of 100% $CO_2$. In a measurement, a deltaU of 214 mV has been determined. The difference between the thermal conductivities between nitrogen and oxygen $O_2$ is not very large. However, with the gas sensor and/or the evaluation arrangement described herein, a deltaU=210 mV may be determined, which is slightly smaller than in the measurement of $N_2$.

Figure 29:
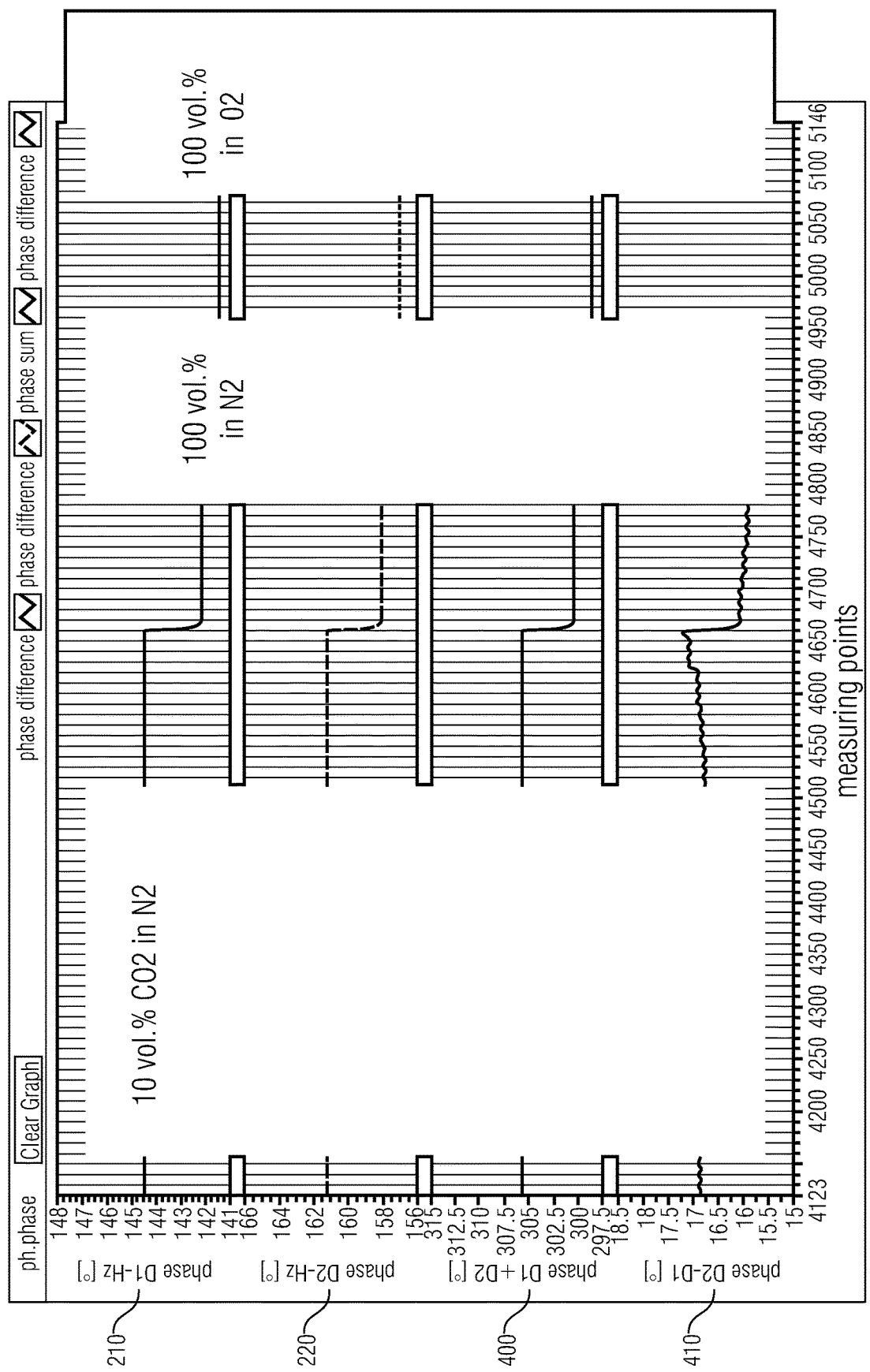
FIG. 29 shows a diagram of different phase information for different gas mixtures according to an embodiment of the present invention.

FIG. 29 illustrates four different phase signals that may represent the phase information sigPhi for the evaluation arrangement according to an embodiment. What is illustrated is the information 210 about the first phase difference, the information 220 about the second phase difference, a phase sum 400 (information 210 plus information 220), and a phase difference 410 (information 220−information 210). According to an embodiment, a temperature of T=24° C. and a pressure of p=1013 mbar are present in the measurement of the phase information 210, 220, 400 and 410. However, this is only an example, and the phase information 210, 220, 400 and 410 may also be captured at different ambient parameter settings (different temperature, different pressure).

According to the embodiment illustrated in FIG. 29, a first portion of (e.g. measurement points 4520 to 4620) constitutes the respective phase information 210, 220, 400 and 410 for a 10 vol. % of $CO_2$ in $N_2$ gas mixture, a second portion of (e.g. measurement points 4670 to 4780) constitutes the respective phase information 210, 220, 400 and 410 for a gas of 100 vol. % $N_2$, and a third portion of (e.g. measurement points 4960 to 5070) constitutes the respective phase information 210, 220, 400 and 410 for a gas of 100 vol. % $O_2$. For example, the durations between the individual portions are waiting times up when the respective mixture is set.

For example, the phase sum 400 constitutes a stable sum signal D1+D2 (D1 corresponds to detector 1 and D2 corresponds to detector 2) of the phase positions. A distinguishability between 100 vol. % of $O_2$ and 100 vol. % of $N_2$ is available for all phase information, for example. According to the embodiment, the largest signal difference occurs between 10 vol. % of $CO_2$ and 0 vol. % of $CO_2$ in $N_2$. Since the phase difference signal 410 is currently very noisy, the phase sum 400 is more advantageous as the phase information.

Figure 30:
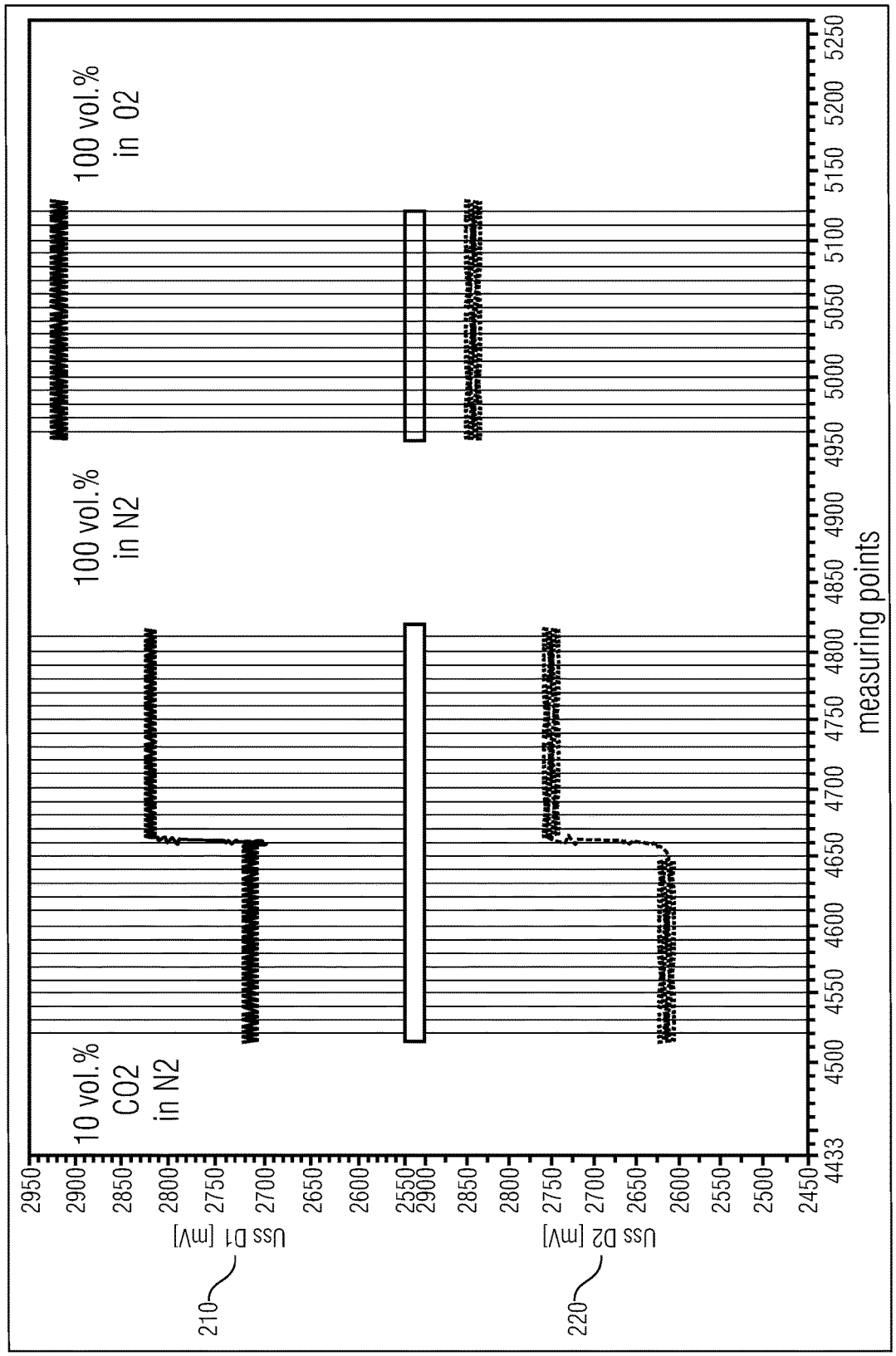
FIG. 30 shows a diagram of different amplitude information for different gas mixtures according to an embodiment of the present invention.

FIG. 30 illustrates information 210 about an amplitude of a detector signal of a first detector and information 220 about an amplitude of a detector signal of a second detector. According to an embodiment, when measuring the amplitude information 210 and 220, there is a temperature of T=24° C. and a pressure of p=1013 mbar. However, this is only an example and the amplitude information 210 and 220 may also be captured at different ambient parameter settings (different temperature, different pressure).

According to the embodiment illustrated in FIG. 30, a first portion (e.g. measurement points 4520 to 4650) constitutes the respective amplitude information 210, 220 for a 10 vol. % of $CO_2$ in $N_2$ gas mixture, a second portion (e.g. measurement points 4670 to 4810) constitutes the respective amplitude information 210, 220 for a gas of 100 vol. % of $N_2$, and a third portion (e.g. measurement points 4960 to 5120) constitutes the respective amplitude information 210, 220 for a gas of 100 vol. % of $O_2$. The durations between the individual portions are waiting times until the respective mixture is set, for example.

The information 210 about the amplitude of the detector signal of the first detector and the information 220 about the amplitude of the detector signal of the second detector constitute stable amplitude signals, for example, wherein D2 (the second detector) has a greater noise according to this embodiment, since its amplitude is lower than the amplitude at D1 (the first detector) (approximately 5 mV compared to 1.8 mV in air). In the two pieces of amplitude information 210, 220, there is a clearer distinguishability between 100 vol. % of $O_2$ and 100 vol. % of $N_2$ as compared to the phase signals (cf. 210, 220, 400 and 410 in FIG. 29). Thus, a comparison of the ratios between the phase and the amplitude may be meaningful in order to infer a concentration of the third gas $O_2$ by means of the evaluation arrangement (for example, if the system has drifted too far away from the fresh air calibration).

Figure 31:
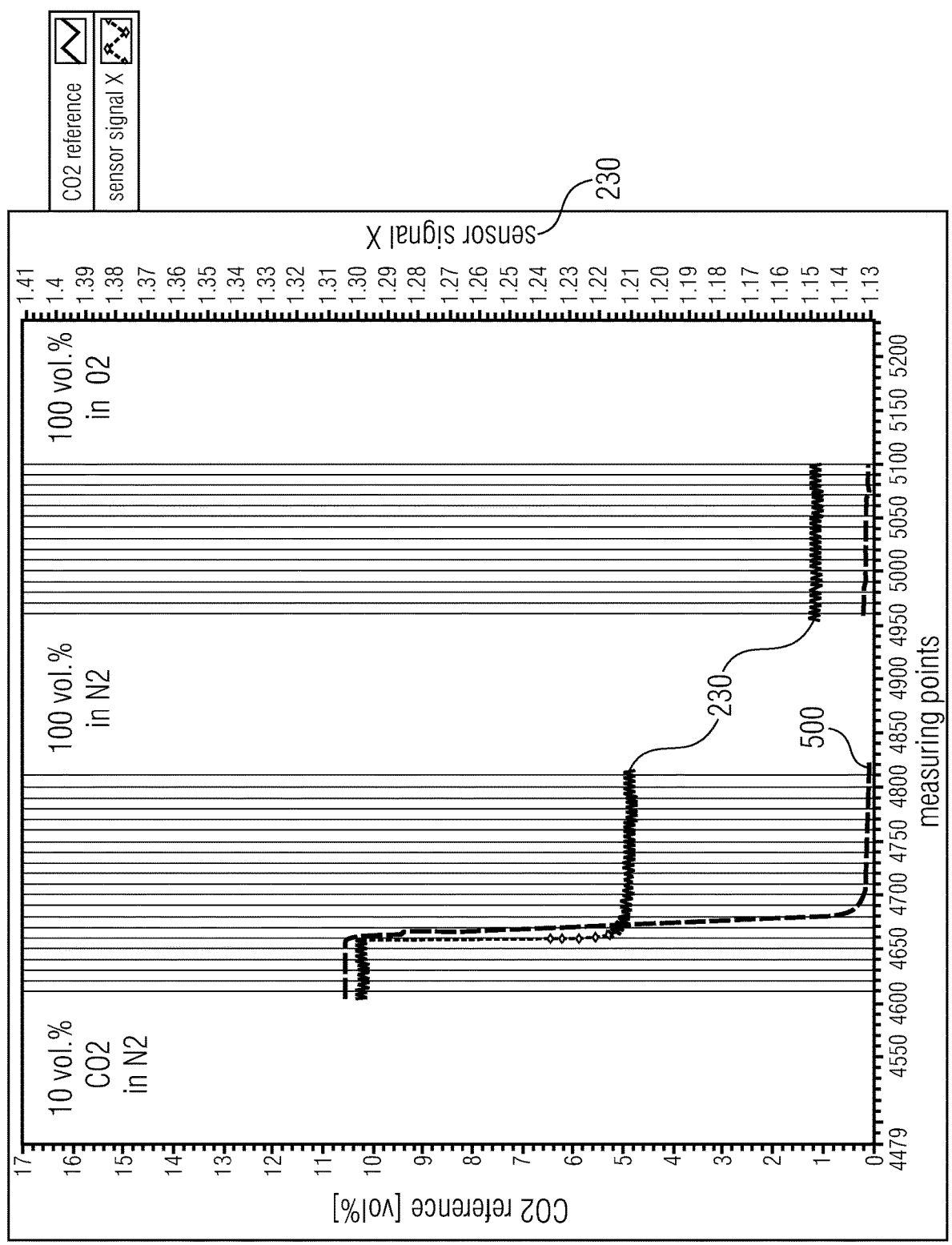
FIG. 31 shows a diagram of a combination signal for different gas mixtures according to an embodiment of the present invention.

FIG. 31 shows a combination signal sigX 230 (with the right y axis) and a $CO_2$ reference signal 500 (with the left y axis). According to an embodiment, when measuring the combination signal sigX 230, there is a temperature of T=24° C. and a pressure of p=1013 mbar. However, this is only an example, and the combination signal sigX 230 may also be captured at different ambient parameter settings (different temperature, different pressure).

According to the embodiment illustrated in FIG. 31, a first portion (e.g. measurement points 4610 to 4650) constitutes a combination signal sigX 230 for a 10 vol. % of $CO_2$ in $N_2$ gas mixture, a second portion (e.g. measurement points 4700 to 4810) constitutes the combination signal sigX 230 for a gas of 100 vol. % of $N_2$, and a third portion of (e.g. measurement points 4960 to 5100) constitutes the combination signal sigX 230 for a gas of 100 vol. % of $O_2$. The durations between the individual portions are waiting times up to when the respective mixture is set, for example. For example, a NDIR reference detector (cf. reference signal 500) only detects a $CO_2$ concentration and cannot differentiate between $N_2$ and $O_2$.

All 3 gas mixtures are clearly distinguishable with the combination signal 230. Thus, comparing ratios between phase and amplitude in order to infer a concentration of the third gas $O_2$ is proposed.

While the difference between 100% of $N_2$ and 100% of $O_2$ only slightly affects the phase signal (FIG. 29), the difference of the amplitude signals between a 10% of $CO_2$-90% of $N_2$ mixture and a 100% of $N_2$ mixture are nearly as large as the difference between 100% of $N_2$ and 100% of $O_2$ (FIG. 30). The combination signal sigX (FIG. 31) slightly blurs this behavior.

In the following, further embodiments describing features and functionalities of the inventive gas sensor in other words are illustrated. These embodiments may be combined with the embodiments described above or may represent alternatives.

According to an embodiment, the gas sensor is a membrane sensor. The thermal gas sensor based on the membrane and thermopile technology with a perforated membrane may be implemented to minimize the parasitic heat transport via the membrane or the suspensions of the structures in order to obtain a higher gas-sensitive signal.

According to an embodiment, the inventive gas sensor may comprise an electronic system, wherein the electronic system may comprise one or several of the following aspects, individually or in combination. The electronic system may comprise a DC sensor amplifier with an operating point that is tracked via software. Furthermore, the electronic system may be implemented to perform a measurement of the phase position via the internal timer structure of the micro controller (MSP430), wherein, e.g., the precise generation of the heater excitation signal via the analog switch and the internal timer structure of the micro controller (MSP430) is used herein. In addition, the electronic system may be implemented to perform a measurement of the phase position of the sensor signals via a Schmitt-trigger that measures the sensor signals free of the DC-offset in the zero point crossing, since the signals are steepest there and the phase noise is therefore minimized. Optionally, the electronic system comprises a control of the heating power via a S1 amplitude controller and/or a control of the timing of the sampling.

According to an embodiment, the gas sensor may have a calibration. The calibration may be configured to form a pseudo signal consisting of a phase and an amplitude, where the emphasis in the signal formation and the equation may be placed on a pseudo signal.

It is to be noted that the embodiments according to the claims may be supplemented with all features, functionalities, and details described herein (if this does not lead to any contradictions).

Features, functionalities, and details of the claims may also be combined with the embodiments described herein in order to obtain additional embodiments.

It is to be noted that features and functionalities shown in individual embodiments or some of the embodiments may also be employed in other embodiments if there are no significant technical reasons against this.

Furthermore, it is to be noted that partial functionalities of the embodiments described herein may be employed if there are no significant technical reasons against this.

Even though some aspects have been described within the context of a device, it is understood that said aspects also represent a description of the corresponding method, so that a block or a structural component of a device is also to be understood as a corresponding method step or as a feature of a method step. By analogy therewith, aspects that have been described within the context of or as a method step also represent a description of a corresponding block or detail or feature of a corresponding device. Some or all of the method steps may be performed while using a hardware device (or using a hardware device), such as a microprocessor, a programmable computer or an electronic circuit. In some embodiments, some or several of the most important method steps may be performed by such a device.

Depending on specific implementation requirements, embodiments of the invention may be implemented in hardware or in software. Implementation may be effected while using a digital storage medium, for example a floppy disc, a DVD, a Blu-ray disc, a CD, a ROM, a PROM, an EPROM, an EEPROM or a FLASH memory, a hard disc or any other magnetic or optical memory which has electronically readable control signals stored thereon which may cooperate, or cooperate, with a programmable computer system such that the respective method is performed. This is why the digital storage medium may be computer-readable.

Some embodiments in accordance with the invention thus comprise a data carrier which comprises electronically readable control signals that are capable of cooperating with a programmable computer system such that any of the methods described herein is performed.

Generally, embodiments of the present invention may be implemented as a computer program product having a program code, the program code being effective to perform any of the methods when the computer program product runs on a computer.

The program code may also be stored on a machine-readable carrier, for example.

Other embodiments include the computer program for performing any of the methods described herein, said computer program being stored on a machine-readable carrier.

In other words, an embodiment of the inventive method thus is a computer program which has a program code for performing any of the methods described herein, when the computer program runs on a computer.

A further embodiment of the inventive methods thus is a data carrier (or a digital storage medium or a computer-readable medium) on which the computer program for performing any of the methods described herein is recorded. The data carrier, the digital storage medium, or the recorded medium are typically tangible, or non-volatile.

A further embodiment of the inventive method thus is a data stream or a sequence of signals representing the computer program for performing any of the methods described herein. The data stream or the sequence of signals may be configured, for example, to be transmitted via a data communication link, for example via the internet.

A further embodiment includes a processing unit, for example a computer or a programmable logic device, configured or adapted to perform any of the methods described herein.

A further embodiment includes a computer on which the computer program for performing any of the methods described herein is installed.

A further embodiment in accordance with the invention includes a device or a system configured to transmit a computer program for performing at least one of the methods described herein to a receiver. The transmission may be electronic or optical, for example. The receiver may be a computer, a mobile device, a memory device or a similar device, for example. The device or the system may include a file server for transmitting the computer program to the receiver, for example.

In some embodiments, a programmable logic device (for example a field-programmable gate array, an FPGA) may be used for performing some or all of the functionalities of the methods described herein. In some embodiments, a field-programmable gate array may cooperate with a microprocessor to perform any of the methods described herein. Generally, the methods are performed, in some embodiments, by any hardware device. Said hardware device may be any universally applicable hardware such as a computer processor (CPU), or may be a hardware specific to the method, such as an ASIC.

For example, the apparatuses described herein may be implemented using a hardware device, or using a computer, or using a combination of a hardware device and a computer.

The apparatuses described herein, or any components of the apparatuses described herein, may at least be partially implement in hardware and/or software (computer program).

For example, the methods described herein may be implemented using a hardware device, or using a computer, or using a combination of a hardware device and a computer.

The methods described herein, or any components of the methods described herein, may at least be partially implement by performed and/or software (computer program).

While this invention has been described in terms of several embodiments, there are alterations, permutations, and equivalents which fall within the scope of this invention.

It should also be noted that there are many alternative ways of implementing the methods and compositions of the present invention. It is therefore intended that the following appended claims be interpreted as including all such alterations, permutations and equivalents as fall within the true spirit and scope of the present invention.

REFERENCES

[Baehr 2008] H. D. Baehr and K. Stephan, Wärme-und Stoffübertragung, 6. neu bearbeitete Auflage ed Springer-Verlag, 2008.
[Simon 2002] I. Simon and M. Arndt. Thermal and gas-sensing properties of a micromachined thermal conductivity sensor for the detection of hydrogen in automotive applications. Sensors and Actuators A: Physical, 97-98, pp. 104-108, April 2002. doi: 10.1016/S0924-4247(01) 00825-1.
[Baar 2001] J. J. van Baar, R. J. Wiegerink, T. S. J. Lammerink, G. J. M. Krijnen, and M. Elwenspoek. Micromachined structures for thermal measurements of fluid and flow parameters. Journal of Micromechanics and Microengineering, 11(4), pp. 311-318, July 2001. doi: 10.1088/0960-1317/11/4/304.
[IST AG 2011] German patent: reference DE 10 2011 075 519 A1; title: Verfahren und Vorrichtung zum thermischen Bestimmen des Massendurchflusses eines Mediums in einer Leitung; inventors: Hepp, Christoph; Krogmann, Florian; Lehmann, Mirko; Polak, Jiri; application date: May 9, 2011
[IST AG 2013] Applied for a German patent under reference DE 10 2013 102 2309.3; title: Thermischer Strömungssensor zur Bestimmung eines Gases oder der Zusammensetzung eines Gasgemisches, sowie dessen Strömungsgeschwindigkeit; inventors: Hepp, Christoph, Krogmann, Florian; application date: Mar. 11, 2013
[IST AG 2015] Applied for a German patent under reference DE 10 2015 107 584.9, title: Verfahren zur Bestimmung eines Produktes aus Wärmekapazität und Dichte, inventors: Hepp, Christoph, Krogmann, Florian, Reyes, Diego; application date: May 13, 2015
[Grien 2012] H. Grienauer—AMS GmbH, Dielheim: Gasanalyse mit thermisch modulierten Wärmeleitfähigkeits-Sensoren mit Fourier-Analyse des Messsignals; 16. GMA/ITG-Fachtagung Sensoren und Messsysteme 2012; 22-23 May 2012; Nürnberg, Germany; Chapter 1.2 Chemische Sensoren; pp 54-61; DOI: 10.5162/sensoren2012/1.2.2; ISBN: 978-3-9813484-0-8
[2003] A. Al-Salaymeh, M. Alhusein, F. Durst, (2003) "Development of a two-wire thermal flow sensor for industrial applications", Journal of Quality in Maintenance Engineering, Vol. 9 Issue: 2, pp. 113-131, "https://doi.org/10.1108/13552510310482370"
[2009] DE 10 2008 047 511 A1 2009 Mar. 19; Vorrichtung und Verfahren zur Atemgasanalyse; Weinmann Geräte für Medizin GmbH+Co. KG, Florian Dietz
[2011] Kliche, Billat, Messner, Zengerle: Sensorsystem zur thermischen Gasanalyse von Gasgemischen, Konferenzbeitrag in Proc. of Mikrosystemtechnik Kongress 2011, Darmstadt, Deutschland, (Poster), 10. Oktober 2011, Seite 875-878, ISBN: 978-3-8007-3367-5 (2011)
[2011] Sensor for gas analysis based on thermal conductivity, specific heat capacity and thermal diffusivity; K Kliche, S Billat, F Hedrich, C Ziegler, R Zengerle; Micro Electro Mechanical Systems (MEMS), 2011 IEEE 24th International Conference on
[2013] Sensor for thermal gas analysis based on micromachined silicon-microwires; K Kliche, G Kattinger, S Billat, L Shen, S Messner, R Zengerle, IEEE Sensors Journal 13 (7), 2626-2635; 2013

The invention claimed is:

1. Evaluation arrangement for a thermal gas sensor with at least one heater and at least one detector,
    wherein the evaluation arrangement is configured to control a heating power applied to the heater dependent on at least one sensor signal from at least one detector in order to bring the at least one sensor signal into a predetermined value range; and
    wherein the evaluation arrangement is configured to consider information about the heating power when deriving information about a gas concentration from the at least one sensor signal.

2. Evaluation arrangement according to claim 1, wherein the evaluation arrangement is configured to apply a periodic signal to the heater.

3. Evaluation arrangement according to claim 1,
    wherein the evaluation arrangement is configured to switch the heating power applied to the heater between two values.

4. Evaluation arrangement according to claim 1,
    wherein the evaluation arrangement is configured to control an amplitude of the heater signal such that a minimum value of the at least one sensor signal and a maximum value of the at least one sensor signal are in the predetermined value range.

5. Evaluation arrangement according to claim 1,
    wherein the evaluation arrangement is configured to set or adjust an amplitude of heating power such that an amplitude of the at least one sensor signal is in a specified amplitude range.

6. Evaluation arrangement according to claim 1, wherein the evaluation arrangement is configured to set or adjust sampling times at which the sensor signal is sampled.

7. Evaluation arrangement according to claim 6, wherein the evaluation arrangement is configured to set the sampling times such that a sampling is carried out at a point in time at which the sensor signal reaches a maximum value, and such that the sampling is carried out at a point in time at which the sensor signal reaches a minimum value.

8. Evaluation arrangement according to claim 1,
    wherein the evaluation arrangement is configured to combine a sensor signal from at least one detector with an offset signal generated by a digital-analog converter in order to acquire an input signal for the analog-digital converter,
    wherein the evaluation arrangement is configured to adjust the offset signal in order to achieve that the input signal of the analog-digital converter remains within a predetermined value range during an entire period of the sensor signal.

9. Evaluation arrangement according to claim 6, wherein the evaluation arrangement is configured to control the heating power only when the sampling times are set or adjusted in a steady state, and when the offset signal is adjusted in a steady state.

10. Evaluation arrangement according to claim 6, wherein the evaluation arrangement is configured to stop controlling the heating power while the sampling times are being set or adjusted and/or while the offset signal is being adjusted.

11. Evaluation arrangement according to claim 1,
    wherein the evaluation arrangement is configured to adjust a mean heating power or a maximum heating power as well as an amplitude of the heating power.

12. Evaluation arrangement according to claim 1, wherein the evaluation arrangement is configured to use a phase difference and/or an amplitude difference and/or an offset difference between the at least one sensor signal and a signal of the heater for deriving the information about the gas concentration.

13. Method for operating an evaluation arrangement for a thermal gas sensor with at least one heater and at least one detector,
   wherein the method comprises controlling a heating power applied to the heater dependent on at least one sensor signal from at least one detector in order to bring a sensor signal into a predetermined value range; and
   wherein the method comprises using an arrangement configured to consider information about the heating power when deriving information about a gas concentration from the at least one sensor signal.

14. Method according to claim 13, wherein a phase difference and/or an amplitude difference and/or an offset difference between the at least one sensor signal and a signal of the heater is used for deriving the information about the gas concentration.

15. A non-transitory digital storage medium having a computer program stored thereon to perform the method for operating an evaluation arrangement for a thermal gas sensor with at least one heater and at least one detector,
   wherein the method comprises controlling a heating power applied to the heater dependent on at least one sensor signal from at least one detector in order to bring a sensor signal into a predetermined value range; and
   wherein the method comprises using an arrangement configured to consider information about the heating power when deriving information about a gas concentration from the at least one sensor signal, when said computer program is run by a computer.

* * * * *